US011814617B2

(12) United States Patent
Drouillard et al.

(10) Patent No.: US 11,814,617 B2
(45) Date of Patent: Nov. 14, 2023

(54) **METHODS OF PRODUCING ENSILED PLANT MATERIALS USING *MEGASPHAERA ELSDENII***

(71) Applicants: KANSAS STATE UNIVERSITY RESEARCH FOUNDATION, Manhattan, KS (US); AXIOTA U.S., INC., Fort Collins, CO (US)

(72) Inventors: James Scott Drouillard, Manhattan, KS (US); Kevin Alan Miller, Easton, KS (US); Celine Caroline Aperce, Wamego, KS (US); Taylor Marie Horne, Manhattan, KS (US); Tara Jo Ellerman, Manhattan, KS (US); Gina Rae Herren, Wamego, KS (US)

(73) Assignees: Kansas State University Research Foundation, Manhattan, KS (US); Axiota U.S., Inc., Fort Collins, CO (US)

( * ) Notice: Subject to any disclaimer, the term of this patent is extended or adjusted under 35 U.S.C. 154(b) by 542 days.

(21) Appl. No.: 16/756,482

(22) PCT Filed: Oct. 19, 2018

(86) PCT No.: PCT/US2018/056777
§ 371 (c)(1),
(2) Date: Apr. 16, 2020

(87) PCT Pub. No.: WO2019/079764
PCT Pub. Date: Apr. 25, 2019

(65) Prior Publication Data
US 2021/0127711 A1  May 6, 2021

Related U.S. Application Data

(60) Provisional application No. 62/575,229, filed on Oct. 20, 2017.

(51) Int. Cl.
*A01N 63/20* (2020.01)
*A23K 30/18* (2016.01)
*C12R 1/01* (2006.01)
*C12N 1/20* (2006.01)

(52) U.S. Cl.
CPC ............... *C12N 1/20* (2013.01); *A01N 63/20* (2020.01); *A23K 30/18* (2016.05); *C12N 1/205* (2021.05); *C12R 2001/01* (2021.05)

(58) Field of Classification Search
CPC .......... A23K 30/18; C12N 1/20; C12N 1/205; A01N 63/20; C12R 2001/01
See application file for complete search history.

(56) References Cited

U.S. PATENT DOCUMENTS

| | | |
|---|---|---|
| 3,713,836 A | 1/1973 | Carlsson |
| 3,956,482 A | 5/1976 | Hahn et al. |
| 4,138,498 A | 2/1979 | Das |
| 4,689,226 A | 8/1987 | Nurmi et al. |
| 5,308,615 A | 5/1994 | Deloach et al. |
| 5,380,525 A | 1/1995 | Leedle et al. |
| 5,529,793 A | 6/1996 | Garner et al. |
| 5,534,271 A | 7/1996 | Ware et al. |
| 5,939,303 A | 8/1999 | Cheng et al. |
| 5,985,605 A | 11/1999 | Cheng et al. |
| 7,485,290 B2 | 2/2009 | Ushida et al. |
| 7,550,139 B2 | 6/2009 | Horn et al. |
| 8,114,396 B2 | 2/2012 | Horn et al. |
| 8,834,853 B2 | 9/2014 | Mazeaud et al. |
| 9,179,693 B2 | 11/2015 | Romero et al. |
| 9,351,516 B2 | 5/2016 | Nissen et al. |
| 9,476,084 B2 | 10/2016 | Brudnak et al. |
| 9,493,737 B2 | 11/2016 | Georgieva et al. |
| 9,546,352 B2 | 1/2017 | Mazeaud et al. |
| 9,554,583 B2 | 1/2017 | Hollard et al. |
| 9,554,590 B2 | 1/2017 | Quintens et al. |
| 10,093,894 B2 | 10/2018 | Yde et al. |
| 10,329,526 B2 | 6/2019 | Salmons et al. |
| 10,370,636 B2 | 8/2019 | Van Hee |
| 10,576,113 B2 | 3/2020 | Madhavamenon et al. |
| 10,834,942 B2 | 11/2020 | Davis et al. |
| 10,856,560 B2 | 12/2020 | Simpson et al. |
| 10,864,457 B2 | 12/2020 | Madsen et al. |
| 10,954,486 B2 | 3/2021 | Georgieva et al. |
| 11,492,587 B2 | 11/2022 | Drouillard et al. |
| 2004/0120963 A1 | 6/2004 | Ushida et al. |
| 2006/0067923 A1 | 3/2006 | Ushida et al. |

(Continued)

FOREIGN PATENT DOCUMENTS

| | | |
|---|---|---|
| AU | 2165688 B | 3/1989 |
| AU | 2018344097 B1 | 4/2020 |

(Continued)

OTHER PUBLICATIONS

Beard, W.L., et al., "Technical Note: A 2-Stage Cecal Cannulation Technique in Standing Horses," *Journal of Animal Science* 89(8):2425-2429, American Society of Animal Science, United States (2011).
International Search Report and Written Opinion for International Application No. PCT/US2018/016321, Commissioner of Patents, Alexandria, Virginia, dated Jun. 6, 2018, 17 pages, United States.
Teather, R.M., "Maintenance of Laboratory Strains of Obligately Anaerobic Rumen Bacteria," *Applied and Environmental Microbiology* 44(2): 499-501, American Society for Microbiology, United States (1982).
Yanke, L.J., et al., "Phytase Activity of Anaerobic Ruminal Bacteria," *Microbiology* 144 (Pt 6): 1565-1573, Minister of Public Works and Government Services Canada, Canada (1998).

(Continued)

*Primary Examiner* — Ruth A Davis
(74) *Attorney, Agent, or Firm* — Sterne, Kessler, Goldstein & Fox P.L.L.C.

(57) ABSTRACT

The present invention relates to methods of producing ensiled plant materials using the anaerobic bacterium *Megasphaera elsdenii* and ensiled plant materials thereof.

20 Claims, 28 Drawing Sheets

(56) References Cited

U.S. PATENT DOCUMENTS

| | | | |
|---|---|---|---|
| 2006/0188550 A1 | 8/2006 | Winn | |
| 2006/0257372 A1 | 11/2006 | Horn et al. | |
| 2008/0138462 A1 | 6/2008 | Chan et al. | |
| 2009/0028992 A1 | 1/2009 | Chan et al. | |
| 2009/0246177 A1* | 10/2009 | Horn | C12N 1/205 |
| | | | 435/244 |
| 2010/0136637 A1 | 6/2010 | Park et al. | |
| 2013/0022575 A1 | 1/2013 | Cassity | |
| 2013/0330308 A1* | 12/2013 | Millan | A61K 35/745 |
| | | | 424/93.46 |
| 2013/0330439 A1 | 12/2013 | Owens et al. | |
| 2014/0037582 A1 | 2/2014 | Romero et al. | |
| 2014/0065617 A1 | 3/2014 | Getman | |
| 2014/0112897 A1 | 4/2014 | Pyne et al. | |
| 2014/0234279 A1 | 8/2014 | Millan | |
| 2015/0140171 A1 | 5/2015 | Nissen et al. | |
| 2015/0218507 A1 | 8/2015 | Georgieva et al. | |
| 2015/0291994 A1 | 10/2015 | Brudnak et al. | |
| 2016/0029666 A1 | 2/2016 | Carpenter et al. | |
| 2016/0213755 A1 | 7/2016 | Romero et al. | |
| 2017/0020935 A1 | 1/2017 | Garner et al. | |
| 2017/0202242 A1 | 7/2017 | Blom et al. | |
| 2017/0224745 A1 | 8/2017 | Dart | |
| 2018/0228181 A1 | 8/2018 | Villamizar et al. | |
| 2019/0358272 A1 | 11/2019 | Laldas et al. | |
| 2019/0376023 A1 | 12/2019 | Hollard et al. | |
| 2020/0123588 A1 | 4/2020 | Mizrahi | |
| 2020/0155470 A1 | 5/2020 | Rieu et al. | |
| 2020/0224151 A1 | 7/2020 | Drouillard et al. | |
| 2020/0281225 A1 | 9/2020 | Kiarie et al. | |
| 2020/0352860 A1 | 11/2020 | Natu et al. | |

FOREIGN PATENT DOCUMENTS

| | | |
|---|---|---|
| CN | 1681522 A | 10/2005 |
| CO | 20190005965 A1 | 6/2019 |
| DE | 4024937 C1 | 4/1992 |
| EP | 0071858 A1 | 2/1983 |
| EP | 2675285 B1 | 11/2017 |
| EP | 2744888 B1 | 12/2017 |
| EP | 3287518 A1 | 2/2018 |
| EP | 3016511 B1 | 10/2019 |
| EP | 3702441 A1 | 9/2020 |
| EP | 2885395 B1 | 10/2020 |
| EP | 3007566 B1 | 12/2020 |
| IN | 235743 | 8/2009 |
| JP | 2013146273 A | 1/2013 |
| KR | 20130021764 A | 3/2013 |
| MX | 9708793 A | 2/1998 |
| RU | 2119288 C1 | 9/1998 |
| RU | 02365621 C2 | 8/2009 |
| RU | 2650870 C1 | 4/2018 |
| WO | WO-1991013146 A1 | 9/1991 |
| WO | WO-1993013666 A1 | 7/1993 |
| WO | WO-1997048812 A2 | 12/1997 |
| WO | WO-02080947 A1 | 10/2002 |
| WO | WO-2004009104 A1 | 1/2004 |
| WO | WO-2009024930 A2 | 2/2009 |
| WO | WO-2010047815 A2 | 4/2010 |
| WO | WO-2011018509 A1 | 2/2011 |
| WO | WO-2012098239 A1 | 7/2012 |
| WO | WO-2012110778 A2 | 8/2012 |
| WO | WO-2013024178 A1 | 2/2013 |
| WO | WO-2013083762 A1 | 6/2013 |
| WO | WO-2013186348 A1 | 12/2013 |
| WO | WO-2014020138 A2 | 2/2014 |
| WO | WO-2014029758 A1 | 2/2014 |
| WO | WO-2014029783 A1 | 2/2014 |
| WO | WO-2016011511 A1 | 1/2016 |
| WO | WO-2016019017 A1 | 2/2016 |
| WO | WO-2017015022 A1 | 1/2017 |
| WO | WO-2017025772 A1 | 2/2017 |
| WO | WO-2018144653 A1 | 8/2018 |
| WO | WO-2018154593 A1 | 8/2018 |
| WO | WO-2018179001 A1 | 10/2018 |
| WO | WO-2019079629 A1 | 4/2019 |
| WO | WO-2019079764 A1 | 4/2019 |
| WO | WO-2019118984 A2 | 6/2019 |
| WO | WO-2019215345 A1 | 11/2019 |
| WO | WO-2020176624 A1 | 9/2020 |
| WO | WO-2020176834 A1 | 9/2020 |
| WO | WO-2020212961 A1 | 10/2020 |
| WO | WO-2020243676 A1 | 12/2020 |
| WO | WO-2021055352 A1 | 3/2021 |
| WO | WO-2021151161 A1 | 8/2021 |

OTHER PUBLICATIONS

International Search Report and Written Opinion for International Application No. PCT/US2018/056777, Commissioner of Patents, Alexandria, Virginia, dated Dec. 13, 2018, 14 pages, United States.

Shrestha, U.T., My scientific Blog-Research and Articles, accessed at https://upendrafts.blogspot.com, 9 pages (2010).

Kailasapathy, K., "Microencapsulation of Probiotic bacteria: Technology and Potential Applications," Curr. Issues Intest. Microbiol. 3(2):39-48, Horizon Scientific Press, United States (Sep. 2002).

Leslie, S. B., et al., "Trehalose and Sucrose Protect Both Membranes and Proteins in Intact Bacteria during Drying," Applied Environmental Microbiology 61(10): 3592-3597, American Society for Microbiology, United States (Oct. 1995).

Mitropoulou, G., et al., "Immobilization Technologies in Probiotic Food Production," Journal of Nutrition and Metabolism 2013:716861, 15 pages, Hindawi Publishing Corporation, India (Oct. 2013).

Miyamoto-Shinohara, Y., et al., "Survival of freeze-dried bacteria," The Journal of General and Applied Microbiology 54(1):9-24, J-SAGE for the Microbiology Research Foundation, Japan (Feb. 2008).

Jorquera, M., et al., "Current and future biotechnological applications of bacterial phytases and phytase-producing bacteria," Microbes and Environments 23(3):182-191, Japanese Society of Microbial Ecology, Japan (2008).

Weimer, P.J., et al., "Fermentation of alfalfa wet-fractionation liquids to volatile fatty acids by Streptococcus bovis and Megasphaera elsdenii," Bioresource Technology 142:88-94, Elsevier, Netherlands (2013).

Khan, T., et al., "Antioxidants Keep the Potentially Probiotic but Highly Oxygen-Sensitive Human Gut Bacterium Faecalibacterium prausnitzii Alive at Ambient Air," PLOS ONE:e96097, 7 pages, Public Library of Science, United States (2014).

United States Department of Agriculture, "SBIR Phase II: Innovations in Manufacturing Technology for a Probiotic Containing Megasphaera Elsdenii NCIMB 41125," retrieved from <https://reeis.usda.gov/web/crisprojectpages/1003461-sbir-phase-ii-innovations-in-manufacturing-technology-for-a-probiotic-containing-megasphaera-elsdenii-ncimb-41125.html>, 7 pages, retrieved on Jun. 9, 2021 (published after Jan. 2017).

Hagg, F., et al., "The effect of a Direct Fed Microbial (Megasphaera elsdenii) on the Productivity and Health of Holstein Cows," South African Journal of Animal Science 40(2): 101-112, South African Society for Animal Science, South Africa (2012).

Leeuw, K-J., et al., "Effect of Megasphaera elsdenii NCIMB 41125 drenching on health and performance of steers fed high and low roughage diets in the feedlot," South African Journal of Animal Science 39(4):337-348, South African Society for Animal Science, South Africa (2009).

Meissner, H.H., et al., "Ruminal acidosis: A review with detailed reference to the controlling agent Megasphaera elsdenii NCIMB 41125," South African Journal of Animal Science 40(2):79-100, South African Society for Animal Science, South Africa (2010).

Rossi, F., et al., "Effect of a Saccharomyces cerevisiae culture on growth and lactate utilization by the ruminal bacterium Megaspahera elsdenii" Ann Zootech 44:403-409, Elsevier, Netherlands (1995).

Third Party Observations mailed Nov. 26, 2021, against EP3577213, in the name of Kansas State University Research Foundation and MS Biotech, Inc., European Patent Office, Germany, 25 pages.

(56) References Cited

OTHER PUBLICATIONS

Adams, G., et al., "Cryopreservation and freeze-drying protocols: the principles of freeze-drying," Extract from Methods in Molecular Biology 368:16, 1 page, Humana Press, Inc., United States (2007).
ATCC Product Sheet, "*Megasphaera elsdenii* (ATCC 25940)," 2 pages (2019).
Bergey, D., et al., "Extract from Bergey's Manual of Systematic Bacteriology vol. 3: The Firmicutes," Genus XIII. *Megasphaera*, 1086, Springer, United States (2009).
Chaucheyras, F., et al., "Effects of a strain of *Saccharomyces cerevisiae* (Levucell® SC[1]), a microbial additive for ruminants, on lactate metabolism in vitro," Can. J. Microbiol. 42:927-933, NRC Research Press, Canada (1996).
Elsden, S.R., et al., "The Production of Fatty Acids By a Gram-negative Coccus," Biochem J. 55(1): 183-189, Portland Press, United States (1953).
Elsden, S.R., et al., "Properties of a Fatty Acid Forming Organism Isolated From The Rumen of Sheep," J. Bacteriol. 72(5): 681-689, American Society for Microbiology, United States (1956).
Gutierrez, J., et al., "Bacterial Changes in the Rumen During the Onset of Feed-lot Bloat of Cattle and Characteristics of *Peptostreptococcus elsdenii* n. sp.," Appl Microbiol 7(1):16-22, American Society for Microbiology, United States (1959).
Langa, R.L.S., "Optimisation of cell growth and shelf life stability of *Megasphaera elsdenii* NCIMB 41125," University of Pretoria: 1-144, South Africa (2010).
Marounek, M., et al., "Metabolism and Some Characteristics of Ruminal Strains of *Megasphaera elsdenii*," Applied and Environmental Microbiology 55(6):1570-1573, American Society for Microbiology, United States (1989).
Material Safety Data Sheet, "Dehydrated Culture Media: reinforced Clostridial Medium (RCM)," Thermofisher Scientific, 2 pages, United States (2001).
National Collection of Industrial Food and Marine Bacteria, "NCIMB 702261," retrieved from <https://store.ncimb.com/page/strains%20record%20name%20display/23138>, retrieved on Oct. 13, 2020, 1 page.
National Collection of Industrial Food and Marine Bacteria, "NCIMB 702262," retrieved from <https://store.ncimb.com/page/strains%20record%20name%20display/23139>, retrieved on Oct. 13, 2020, 1 page.
National Collection of Industrial Food and Marine Bacteria, "NCIMB 702410," retrieved from <https://store.ncimb.com/page/strains%20record%20name%20display/23143>, retrieved on Oct. 13, 2020, 1 page.
Rossi, F., et al., "Effects of peptidic fractions from *Saccharomyces cerevisiae* culture on growth and metabolism of the ruminal bacteria *Megasphaera elsdenii*," Anim. Res 53:177-186, INRA/EDP Sciences, United States (2004).
Soto-Cruz, O., et al., "Stimulation of the *Megasphaera elsdenii*'s Butyrate Production in Continuous Culture by a Yeast Additive," Brazilian Archives of Biology and Technology 44(2):179-184, Instituto de Tecnologia do Paraná, Brazil (2001).
Suihiko, M.-L., et al., "Maintenance of the anaerobic beer spoilage bacteria *Pectinatus* and *Megaspahaera*," Food Microbiology 7:33-41, Academic Press, United States (1990).
Wikipedia, "Freeze-drying," retrieved from <https://en.wikipedia.org/w/index.php?title=freeze-drying&oldid=1057299009>, retrieved on Nov. 26, 2021, 13 pages (2021).
Zhu, D., et al., Feed Research No. 3, Scienceline Publication, United States (2007), 4 pages.
English language translation of Office Action for Chinese Application No. 201880076967.4, dated Nov. 24, 2022, 19 pages.
American Type Culture Collection, "*Megasphaera elsdenii* (Gutierrez et al.) Rogosa 25940," retrieved from <https://www.atcc.org/products/25940>, retrieved on Jan. 31, 2023, 7 pages.
American Type Culture Collection, "*Megasphaera elsdenii* (Gutierrez et al.) Rogosa 17752," retrieved from <https://www.atcc.org/products/17752>, retrieved on Jan. 31, 2023, 6 pages.
American Type Culture Collection, "*Megasphaera elsdenii* (Gutierrez et al.) Rogosa 17753," retrieved from <https://www.atcc.org/products/17753>, retrieved on Jan. 31, 2023, 7 pages.
National Collection of Industrial Food and Marine Bacteria, "NCIMB 702264," retrieved from <https://store.ncimb.com/page/Strains%20record%20name%20display/92846>, retrieved on Jan. 31, 2023, 1 page.
National Collection of Industrial Food and Marine Bacteria, "NCIMB 702331," retrieved from <https://store.ncimb.com/page/Strains%20record%20name%20display/92847>, retrieved on Jan. 31, 2023, 1 page.
National Collection of Industrial Food and Marine Bacteria, "NCIMB 702409," retrieved from <https://store.ncimb.com/page/Strains%20record%20name%20display/92848>, retrieved on Jan. 31, 2023, 1 page.
Co-pending Application, U.S. Appl. No. 18/045,280, inventors Drouillard, J.S., et al., filed Oct. 10, 2022 (Not Published).

\* cited by examiner

| VFA | Day 0 | | Day 14 | | Day 120 | | | |
|---|---|---|---|---|---|---|---|---|
| | Control | Megasphaera | Control | Megasphaera | Control | Megasphaera | SEM | P value |
| Acetate | 44.68 | 45.25 | 68.98 | 68.60 | 166.19 | 149.70 | 10.61 | 0 |
| Propionate | 0.00 | 0.00 | 0.00 | 0.00 | 1.04 | 1.18 | 0.32 | 0 |
| Isobutyrate | 2.36 | 2.42 | 1.12 | 1.27 | 2.92 | 4.84 | 0.82 | 0 |
| Butyrate | 0.00 | 0.00 | 0.00 | 0.00 | 0.00 | 0.52 | 0.18 | - |
| Isovalerate | 0.21 | 0.34 | 0.710 | 0.78 | 1.4 | 1.7 | 0.39 | 0 |
| Valerate | 0.00 | 0.00 | 0.00 | 0.00 | 0.92 | 1.37 | 0.26 | 0 |
| Isocaproate | 0.00 | 0.00 | 0.00 | 0.00 | 1.62 | 1.63 | 0.12 | 0 |
| Caproate | 0.00 | 0.00 | 0.00 | 0.00 | 1.26 | 1.02 | 0.16 | 0 |
| Heptanoate | 0.00 | 0.00 | 0.00 | 0.00 | 0.28 | 0.36 | 0.02 | 0 |
| Total VFA | 47.25 | 48.02 | 70.81 | 70.64 | 175.65 | 162.35 | 11.42 | 0 |

FIG. 4

| VFA | Day 0 | | Day 14 | | | |
|---|---|---|---|---|---|---|
| | Control | Megasphaera | Control | Megasphaera | SEM | P-value |
| Acetate | 69.97 | 68.60 | 46.75 | 29.74 | 5.40 | D |
| Propionate | 0.00 | 0.00 | 16.40 | 11.29 | 2.81 | D |
| Isobutyrate | 1.13 | 1.27 | 4.98 | 3.52 | 0.61 | D |
| Butyrate | 0.00 | 0.00 | 7.57 | 9.34 | 1.26 | D |
| Isovalerate | 0.71 | 0.78 | 1.10 | 1.42 | 0.09 | D |
| Valerate | 0.00 | 0.00 | 0.40 | 0.23 | 0.10 | D |
| Isocaproate | 0.00 | 0.00 | 0.00 | 0.00 | - | - |
| Caproate | 0.00 | 0.00 | 0.65 | 0.54 | 0.19 | D |
| Heptanoate | 0.00 | 0.00 | 0.00 | 0.00 | - | - |
| Total VFA | 70.81 | 70.64 | 78.09 | 56.09 | 6.65 | - |

FIG. 8

| VFA | Day 0 | | Day 14 | | | |
|---|---|---|---|---|---|---|
| | Control | Megasphaera | Control | Megasphaera | SEM | P-value |
| Acetate | 101.07 | 76.87 | 166.19 | 149.70 | 17.68 | D |
| Propionate | 2.42 | 0.83 | 1.05 | 1.18 | 0.57 | - |
| Isobutyrate | 7.95 | 3.07 | 2.92 | 4.84 | 1.28 | - |
| Butyrate | 1.51 | 0.25 | 0.00 | 0.52 | 0.35 | - |
| Isovalerate | 1.08 | 0.51 | 1.41 | 1.71 | 0.57 | - |
| Valerate | 0.00 | 0.00 | 0.92 | 1.38 | 0.32 | D |
| Isocaproate | 2.10 | 1.02 | 1.62 | 1.63 | 0.30 | - |
| Caproate | 1.86 | 0.89 | 1.26 | 1.03 | 0.29 | T |
| Heptanoate | 0.47 | 0.04 | 0.29 | 0.37 | 0.05 | - |
| Total VFA | 118.47 | 83.73 | 175.65 | 162.36 | 18.41 | D |

FIG. 13

METHODS OF PRODUCING ENSILED PLANT MATERIALS USING *MEGASPHAERA ELSDENII*

CROSS REFERENCE TO RELATED APPLICATIONS

This application is a national phase entry of International Application No. PCT/US2018/056777, filed Oct. 19, 2018, which claims the priority benefit of U.S. Provisional Application No. 62/575,229, filed Oct. 20, 2017, each of which is hereby incorporated by reference herein in its entirety.

BACKGROUND OF THE DISCLOSURE

Field of Invention

The present invention relates to methods of producing ensiled plant materials using the anaerobic bacterium *Megasphaera elsdenii*. The present invention also relates to ensiled plant materials produced by the methods.

Background

Ensiling is a fermentative process used to preserve plant materials (e.g., forages and/or grains) consumed by animals such as livestock. The preserved plant material produced by the ensiling process is referred to as an ensiled plant material. Examples of ensiled plant materials include, but are not limited to, an ensiled forage, also known as a silage, an ensiled grain, also known as a fermented grain, and combinations of ensiled forages and grains.

In general, a plant material is collected and sealed in a silo, which is any container that can maintain an anaerobic environment. Initially, entrapped atmospheric oxygen in the silo is reduced by respiratory activity of the plant material and aerobic microorganisms. Fermentation begins when conditions in the silo become anaerobic. This can be aided by methods including compacting the plant materials and preventing entry of air into the silo.

Growth of undesirable microorganisms during the ensiling process such as clostridia, enterobacteria, and yeasts can be inhibited by lactic acid fermentation associated with lactic acid bacteria present on the plant materials. Under favorable ensiling conditions, lactic acid bacteria will acidify the plant materials and prevent competitive growth by the undesirable microorganisms. However, if the pH is not successfully controlled during the ensiling process, undesirable microorganisms can proliferate and degrade amino acids, resulting in an ensiled plant material with lower nutritional value. Additionally, further degradation of the ensiled plant material can occur following exposure to air when the silo is opened.

Thus, there is a need for improved methods of producing ensiled plant materials.

BRIEF SUMMARY OF THE DISCLOSURE

The present disclosure is directed to a method of producing an ensiled plant material with improved aerobic stability, comprising: (a) applying an effective amount of *M. elsdenii* cells to a plant material, and (b) ensiling the plant material to produce an ensiled plant material, wherein the ensiled plant material comprises improved aerobic stability as compared to a control ensiled plant material produced in the absence of the *M. elsdenii* cells.

In certain embodiments, the improved aerobic stability comprises a decreased pH.

The present disclosure is directed to a method of producing an increased amount of an ensiled plant material, comprising: (a) applying an effective amount of *M. elsdenii* cells to a plant material, and (b) ensiling the plant material to produce an ensiled plant material, wherein the amount of the ensiled plant material produced is increased as compared to the amount of a control ensiled plant material produced in the absence of the *M. elsdenii* cells.

The present disclosure is directed to a method of producing an ensiled plant material, comprising: (a) applying *M. elsdenii* cells to a plant material, wherein the cells are selected from the group consisting of: ATCC® 25940, ATCC® 17752, ATCC® 17753, NCIMB 702261, NCIMB 702262, NCIMB 702264, NCIMB 702331, NCIMB 702409, NCIMB 702410, NCIMB 41125, NCIMB 41787, NCIMB 41788, NRRL 18624, NIAH 1102, and combinations thereof, and (b) ensiling the plant material to produce an ensiled plant material.

In certain embodiments, any of the methods further comprises applying an additive to the plant material.

In certain embodiments, the applying is before harvesting of the plant material, after harvesting of the plant material, at the time of ensiling, or combinations thereof.

In certain embodiments, the additive is selected from the group consisting of: another microorganism, an enzyme, a fermentable substrate, an acid, a preservative, a nutrient, and combinations thereof.

In certain embodiments, the *M. elsdenii* cells are selected from the group consisting of: ATCC® 25940, ATCC® 17752, ATCC® 17753, NCIMB 702261, NCIMB 702262, NCIMB 702264, NCIMB 702331, NCIMB 702409, NCIMB 702410, NCIMB 41125, NCIMB 41787, NCIMB 41788, NRRL 18624, NIAH 1102, and combinations thereof.

In certain embodiments, the *M. elsdenii* cells are *M. elsdenii* NCIMB 41125 cells.

In certain embodiments, the plant material is selected from the group consisting of: a forage, crop, grass, legume, grain, fruit, vegetable, or combinations thereof.

In certain embodiments, the plant material is corn, alfalfa, wheat, rye, barley, oats, triticale, millet, clover, sorghum, or combinations thereof.

In certain embodiments, any of the methods further comprises applying the *M. elsdenii* cells in a liquid.

In certain embodiments, any of the methods further comprises mixing freeze-dried *M. elsdenii* cells with a liquid prior to applying the cells.

In certain embodiments, any of the methods further comprises applying the *M. elsdenii* cells as freeze-dried cells.

In certain embodiments, a dry carrier comprises the freeze-dried cells.

In certain embodiments, any of the methods further comprises applying at least about $10^6$ to about $10^{14}$ CFU of *M. elsdenii* cells per ton of plant material.

The present disclosure is directed to an ensiled plant material produced by any of the methods.

BRIEF DESCRIPTION OF THE DRAWINGS/FIGURES

FIG. 1 shows the temperature (° C.) of plant material measured hourly during 120 days of ensiling. The "Megasphaera" and "Control" groups in FIGS. 1-14 were, respectively, plant material from fresh corn that was treated with $2 \times 10^8$ CFU/ml *Megasphaera elsdenii* cells (*Megasphaera*

*elsdenii* strain NCIMB 41125, MSBiotec®, Wamego, Kansas) at a rate of 50 milliliters per ton of plant material ("Megasphaera") and plant material from fresh corn that was not treated ("Control").

FIG. 2 shows the cumulative weight loss (%) in the "Megasphaera" and "Control" groups by days 7, 14, 21, 28, 39, 90, and 120 of ensiling as determined by weighing silos containing the plant materials on those days and comparing to their respective starting weights on day 0 of ensiling. Effect of Treatment, $P<0.01$; Effect of Day, $P>0.10$; Treatment by Day Interaction, $P>0.10$; Standard Error of the Mean=3.16.

FIG. 3 shows the mean pH of samples taken from the "Megasphaera" and "Control" groups. Samples were taken from the silos on three opening days (i.e., days on which the silos were opened), including day 0 ("D0"), day 14 ("D14"), and day 120 ("D120") of ensiling. No Effect of Treatment, $P>0.6$; Standard Error of the Mean=0.02.

FIG. 4 shows mean volatile fatty acid (VFA) concentrations (millimolar) in samples taken from the "Megasphaera" and "Control" groups as described in FIG. 3. "SEM" is the Standard Error of the Mean. "D"=Opening Day Effect, with $P<0.05$.

FIG. 5 shows the temperature (° C.) measured over 14 days of exposure to ambient air in "Megasphaera" and "Control" samples collected on opening day 14 as described in FIG. 3. The temperature of "Megasphaera" was greater than "Control" at 72-110 hours, $P<0.05$. Treatment by Time Interaction, $P<0.01$; Effect of Time, $P<0.01$; Effect of Treatment, $P<0.01$; Standard Error of the Mean=0.023.

FIG. 6 shows the mean pH of "Megasphaera" and "Control" samples measured on day 0 ("D0") and day 14 ("D14") of exposure to ambient air after collection on opening day 14 as described in FIG. 3. Treatment by Day Interaction, $P<0.05$; Effect of Time, $P<0.01$; Effect of Treatment, $P<0.05$; Treatments denoted with an asterisk ("*") are different from one another on day 14, $P<0.05$; Standard Error of the Mean=0.07.

FIG. 7 shows mean millimolar ("mM") concentration of total volatile fatty acids in "Megasphaera" and "Control" samples measured on day 0 ("D0") and day 14 ("D14") of exposure to ambient air after collection on opening day 14 as described in FIG. 3. FIG. 7 also shows the mean concentration of volatile fatty acids in a pre-ensiling sample. Treatment by Opening Day Interaction, $P>0.5$; Effect of Inoculant, $P>0.1$; Effect of Opening Day, $P<0.6$; Standard Error of the Mean=6.65.

FIG. 8 shows mean millimolar concentrations of volatile fatty acids ("VFA") in "Megasphaera" and "Control" samples measured on day 0 ("D0") and day 14 ("D14") of exposure to ambient air after collection on opening day 14 as described in FIG. 3. "D"=Opening Day Effect, with $P<0.05$.

FIG. 9 shows average weight in pounds ("lb") at day 0, day 7, and day 14 of exposure to ambient air for each "Megasphaera" and "Control" sample collected on opening day 14 as described in FIG. 3. Treatment by Day Interaction, $P>0.9$; Effect of Day, $P>0.1$; Effect of Treatment, $P>0.6$; Standard Error of the Mean=0.16.

FIG. 10 shows the temperature (° C.) measured over 14 days of exposure to ambient air in "Megasphaera" and "Control" samples collected on opening day 120 as described in FIG. 3. The temperature of "Megasphaera" was greater than "Control" at 259-294 hours, $P<0.10$. Treatment by Time Interaction, $P>0.10$; Effect of Time, $P<0.01$; Effect of Treatment, $P<0.01$; Standard Error of the Mean=1.23.

FIG. 11 shows the mean pH of "Megasphaera" and "Control" samples measured on day 0 ("D0") and day 14 ("D14") of exposure to ambient air after collection on opening day 120 as described in FIG. 3. Treatment by Day Interaction, $P>0.1$; Effect of Time, $P>0.1$; Effect of Treatment, $P>0.1$; Standard Error of the Mean=0.23.

FIG. 12 shows mean millimolar ("mM") concentration of total volatile fatty acids in "Megasphaera" and "Control" samples measured on day 0 ("D0") and day 14 ("D14") of exposure to ambient air after collection on opening day 120 as described in FIG. 3. FIG. 12 also shows the mean concentration of volatile fatty acids in a pre-ensiling sample. Treatment by Oxygen Exposure Interaction, $P>0.5$; Effect of Inoculant, $P>0.15$; Effect of Day of Oxygen Exposure, $P<0.01$; Standard Error of the Mean=18.4.

FIG. 13 shows mean millimolar concentrations of volatile fatty acids ("VFA") in "Megasphaera" and "Control" samples measured on day 0 ("D0") and day 14 ("D14") of exposure to ambient air after collection on opening day 120 as described in FIG. 3. "D"=Day of Oxygen Exposure Effect; "I"=Interaction Effect; "T"=Treatment Effect; Letters indicate $P<0.05$.

FIG. 14 shows average weight in pounds ("lb") at day 0, day 7, and day 14 of exposure to ambient air for each "Megasphaera" and "Control" sample collected on opening day 120 as described in FIG. 3. Treatment by Day Interaction, $P>0.90$; Effect of Day, $P>0.6$; Effect of Treatment, $P<0.01$; Standard Error of the Mean=0.10.

Figure 18:
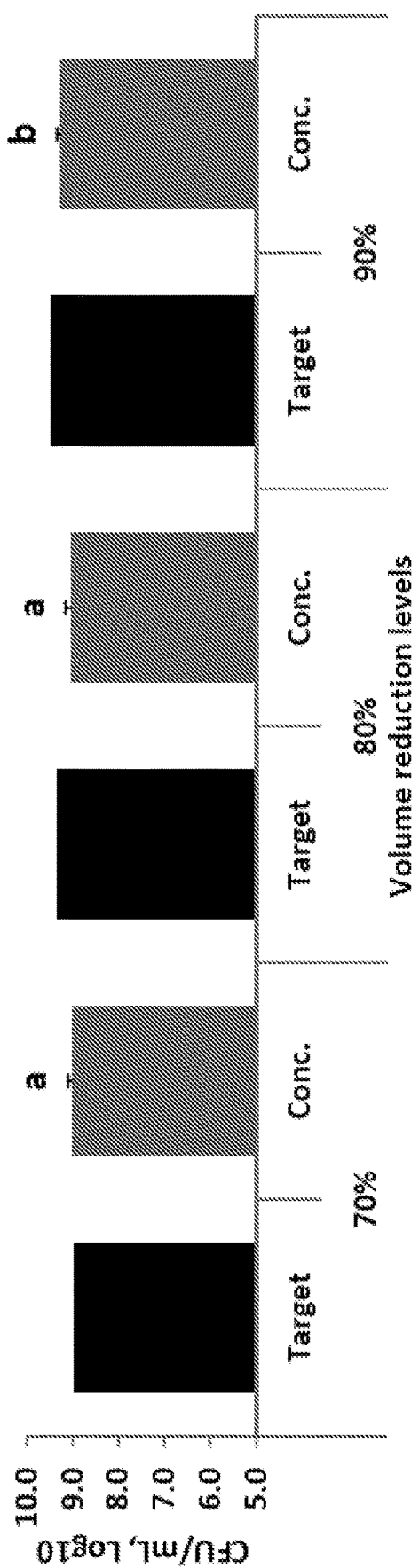

FIG. 18 shows yield of *M. elsdenii* cells in CFU/mL of retentate on the y-axis in Log 10 scale after processing through the TFF system. The x-axis indicates a 70%, 80%, or 90% volume reduction by the system. "Target" refers to the theoretical recovery of *M. elsdenii* cells after TFF processing. "Conc." refers to the actual recovery of *M. elsdenii* cells in the retentate, which is the volume of concentrated cells remaining after the noted volume reductions.

Figure 19:
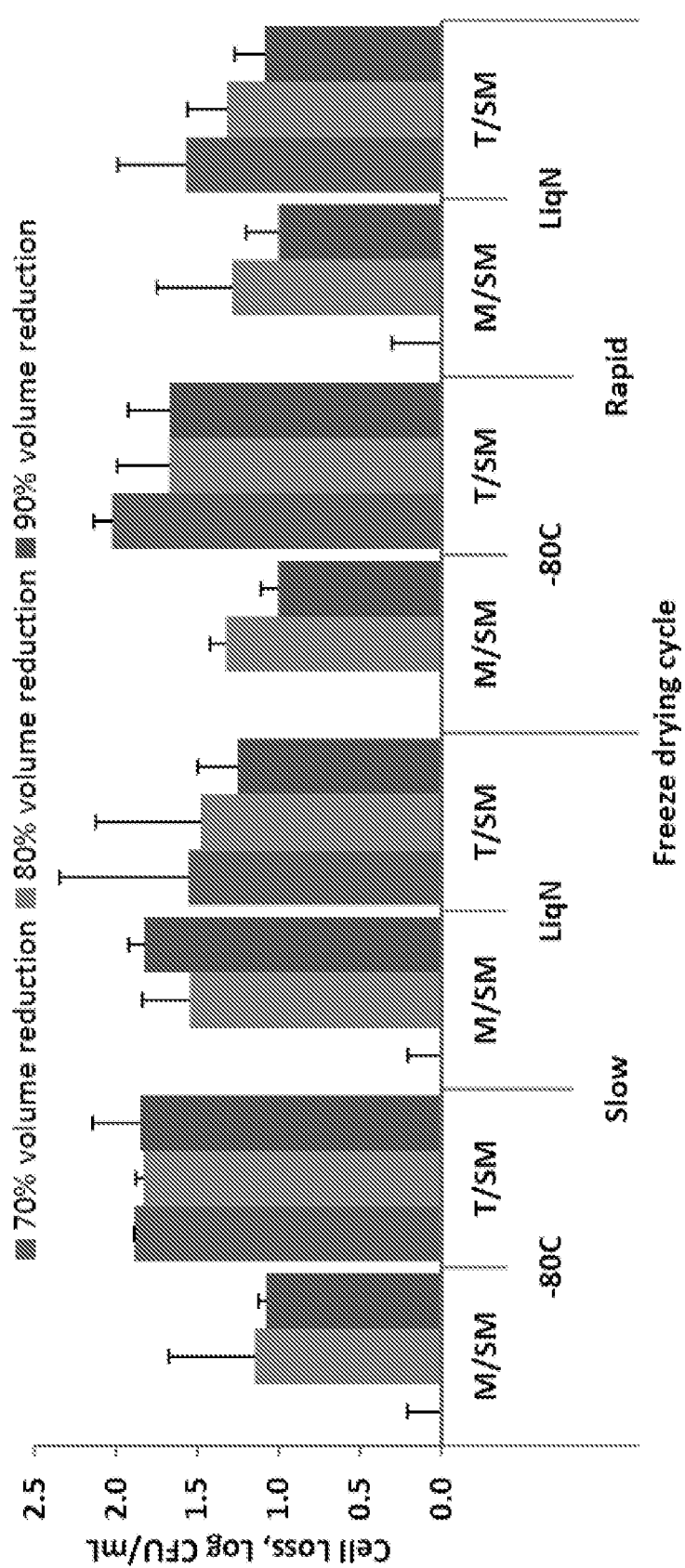

FIG. 19 shows cell loss following freezing of cells at −80° C. or in liquid nitrogen (LiqN) and freeze-drying of cells using a slow (38 hours at 135 mTorr) or rapid (18.5 hours at 250 mTorr) cycle. The cells were from retentates after 70%, 80%, or 90% volume reduction with TFF of cultures having either 8% maltodextrin/15% skim milk (M/SM) or 8% trehalose/15% skim (T/SM) as cryoprotectants.

Figure 20:
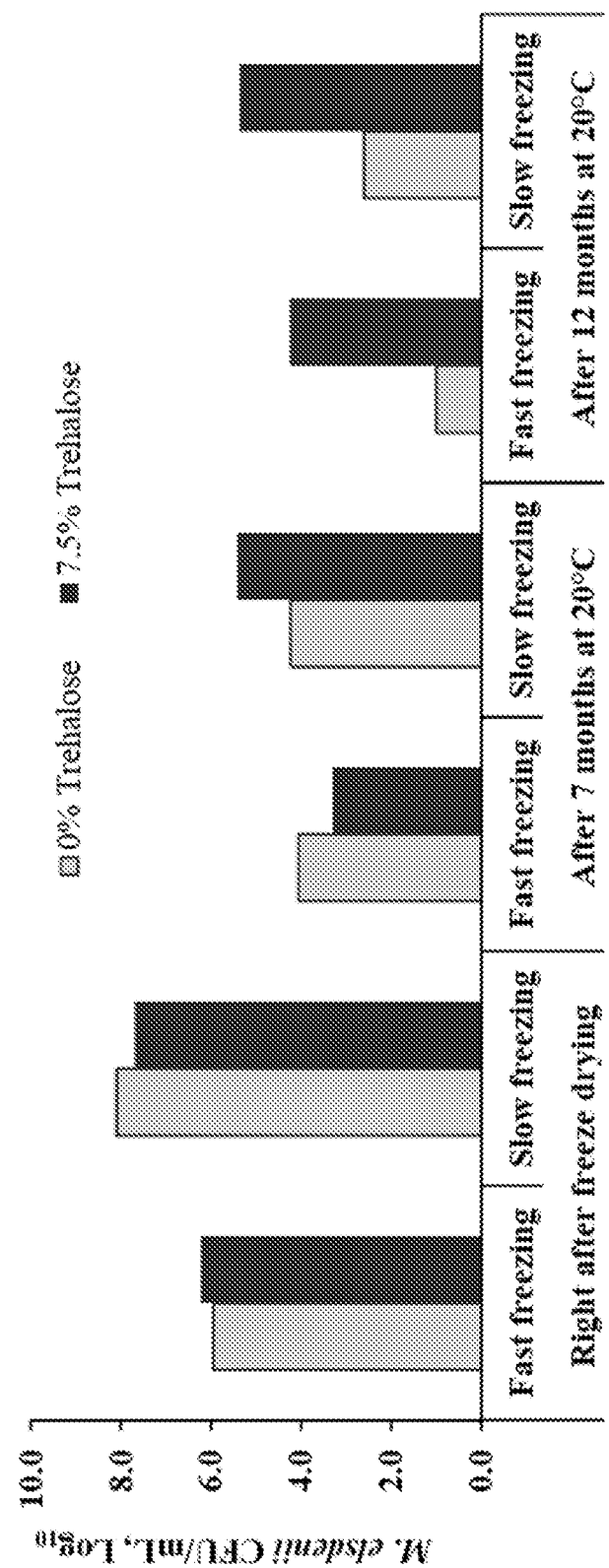

FIG. 20 shows yield of *M. elsdenii* NCIMB 41125 cells after an initial fast (liquid nitrogen) or slow (−20° C.) freezing followed by freeze-drying (in the presence of 15% maltodextrin and 0% or 7.5% trehalose).

Figure 21:
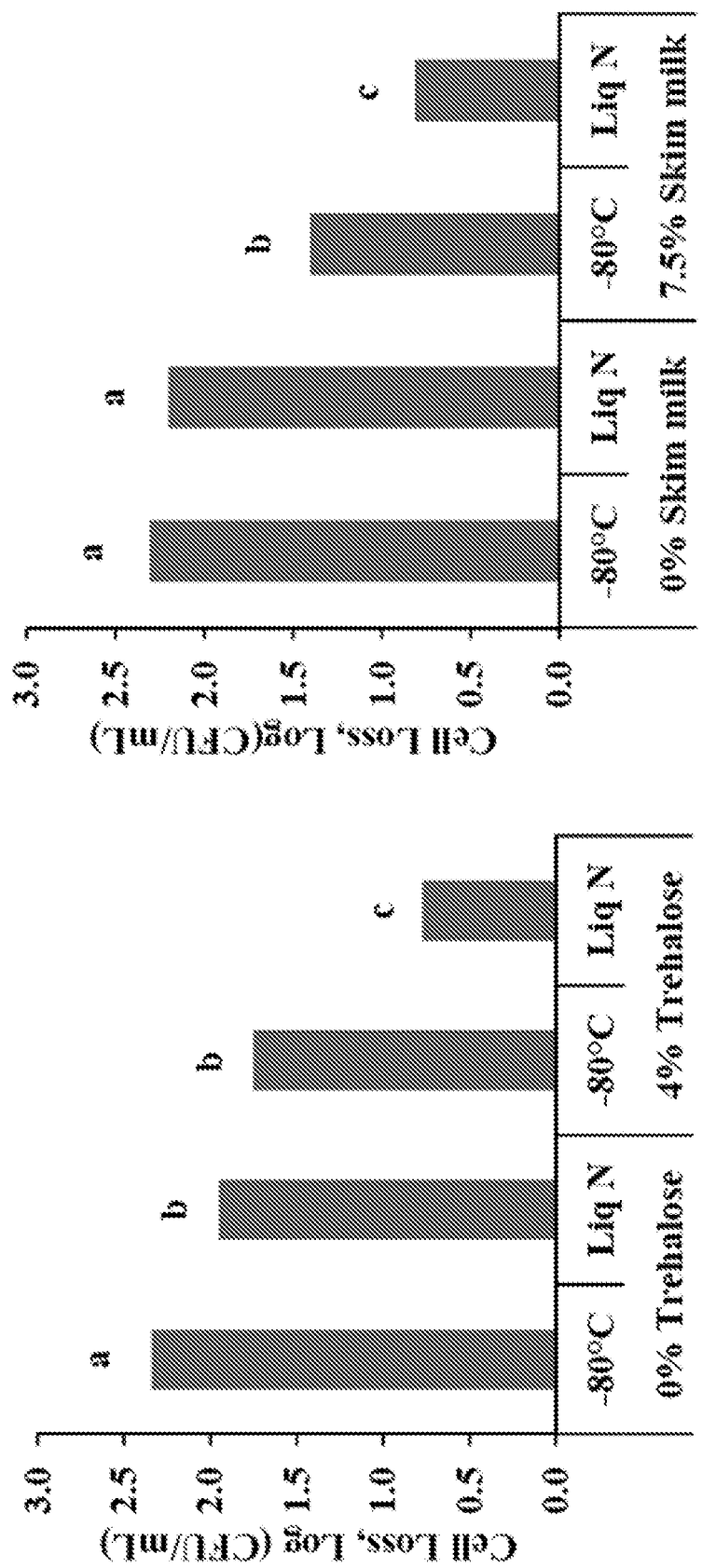

FIG. 21 shows cell loss observed in *M. elsdenii* NCIMB 41125 cells frozen with or without 4% trehalose or 7.5% skim milk at either −80° C. or in liquid nitrogen (LiqN).

Figure 22:
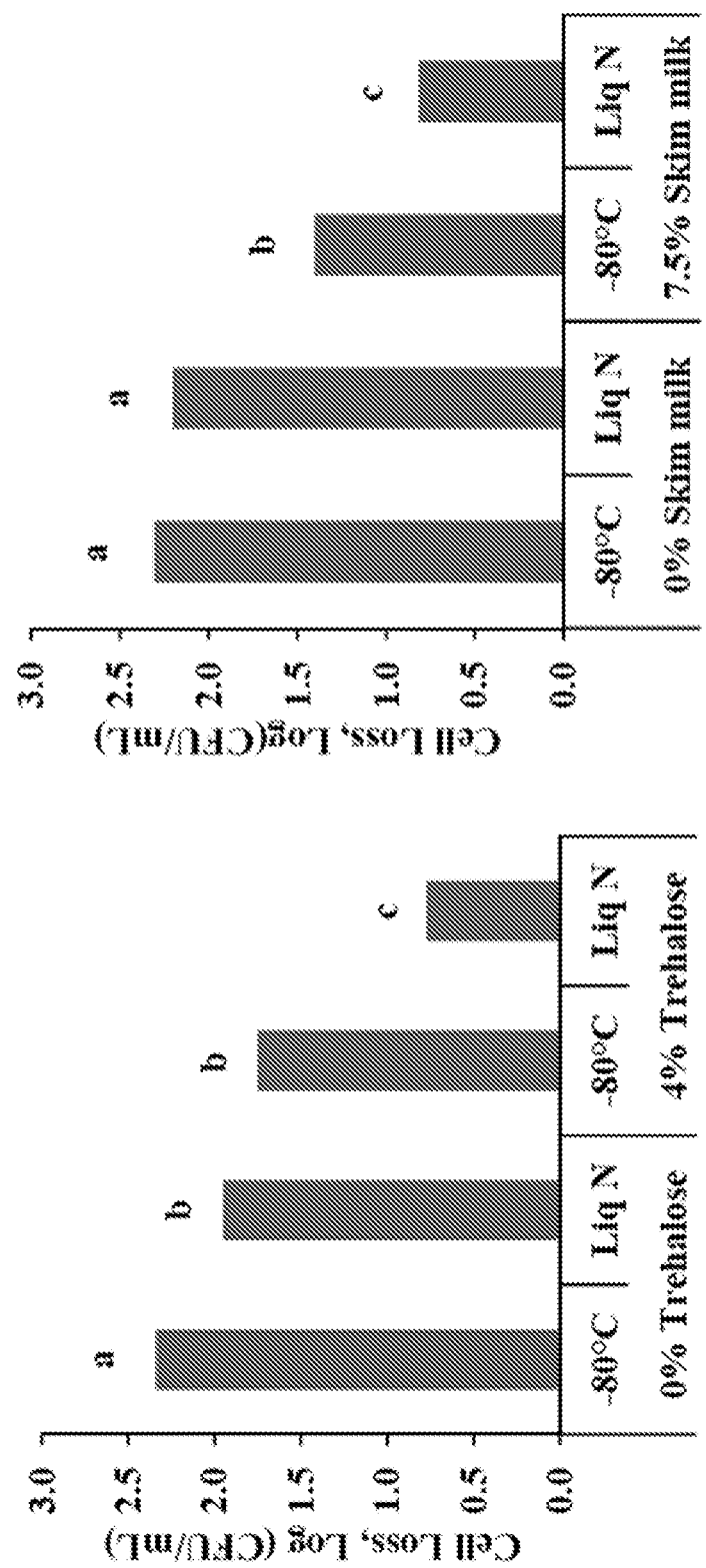

FIG. 22 shows cell loss observed on freeze-dried samples obtained from 90% volume reduction retentate, mixed with 8% trehalose/15% skim milk (T/SM) or 8% maltodextrin/15% skim milk (M/SM), frozen at −80° C. or in liquid nitrogen (LiqN), and freeze-dried using the rapid cycle and stored at room temperature or 4° C. under anaerobic conditions for up to 24 weeks.

Figure 23:
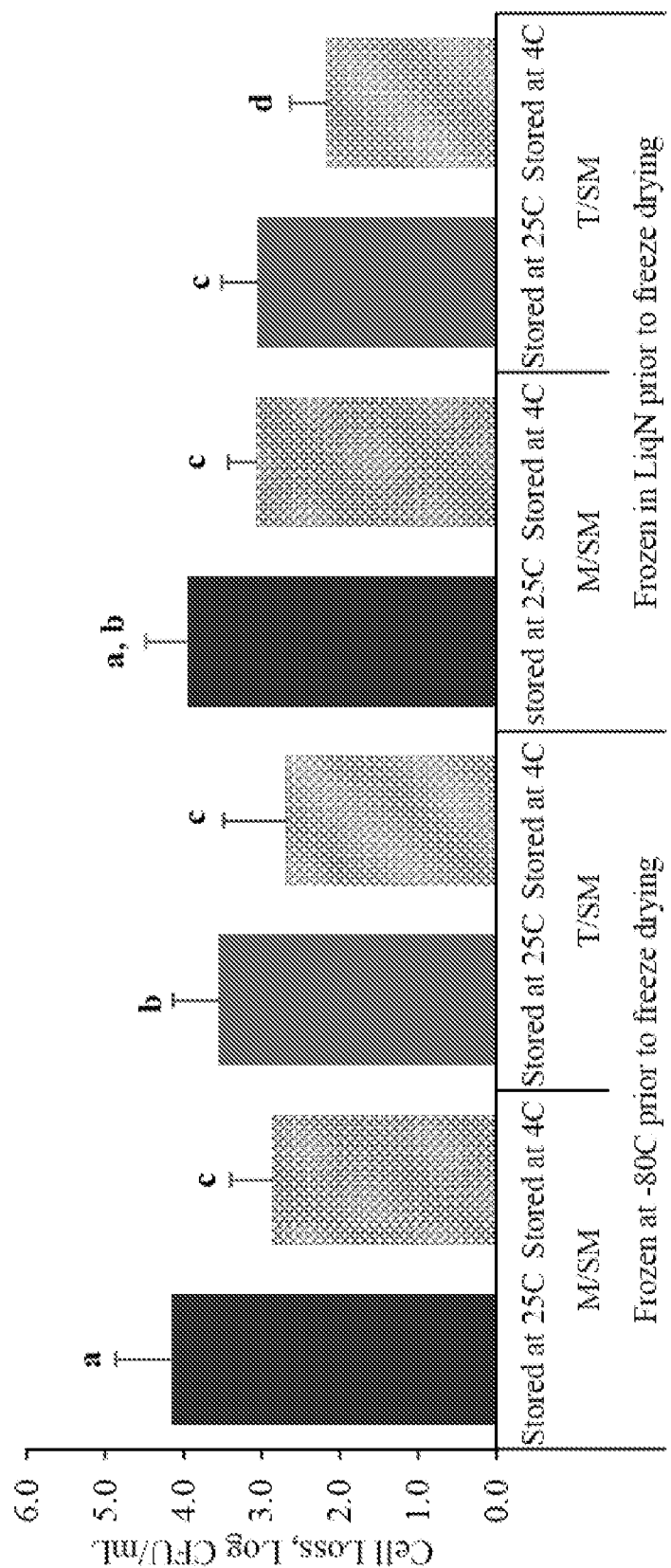

FIG. 23 shows cell loss observed on freeze-dried samples obtained from 90% volume reduction retentate, mixed with 8% trehalose/15% skim milk (T/SM) or 8% maltodextrin/15% skim milk (M/SM), frozen at −80° C. or in liquid nitrogen (LiqN), and freeze-dried using the rapid cycle and stored at room temperature or 4° C. under anaerobic conditions for 24 weeks. Bars without a common superscript are statistically different, P<0.02.

Figure 24:
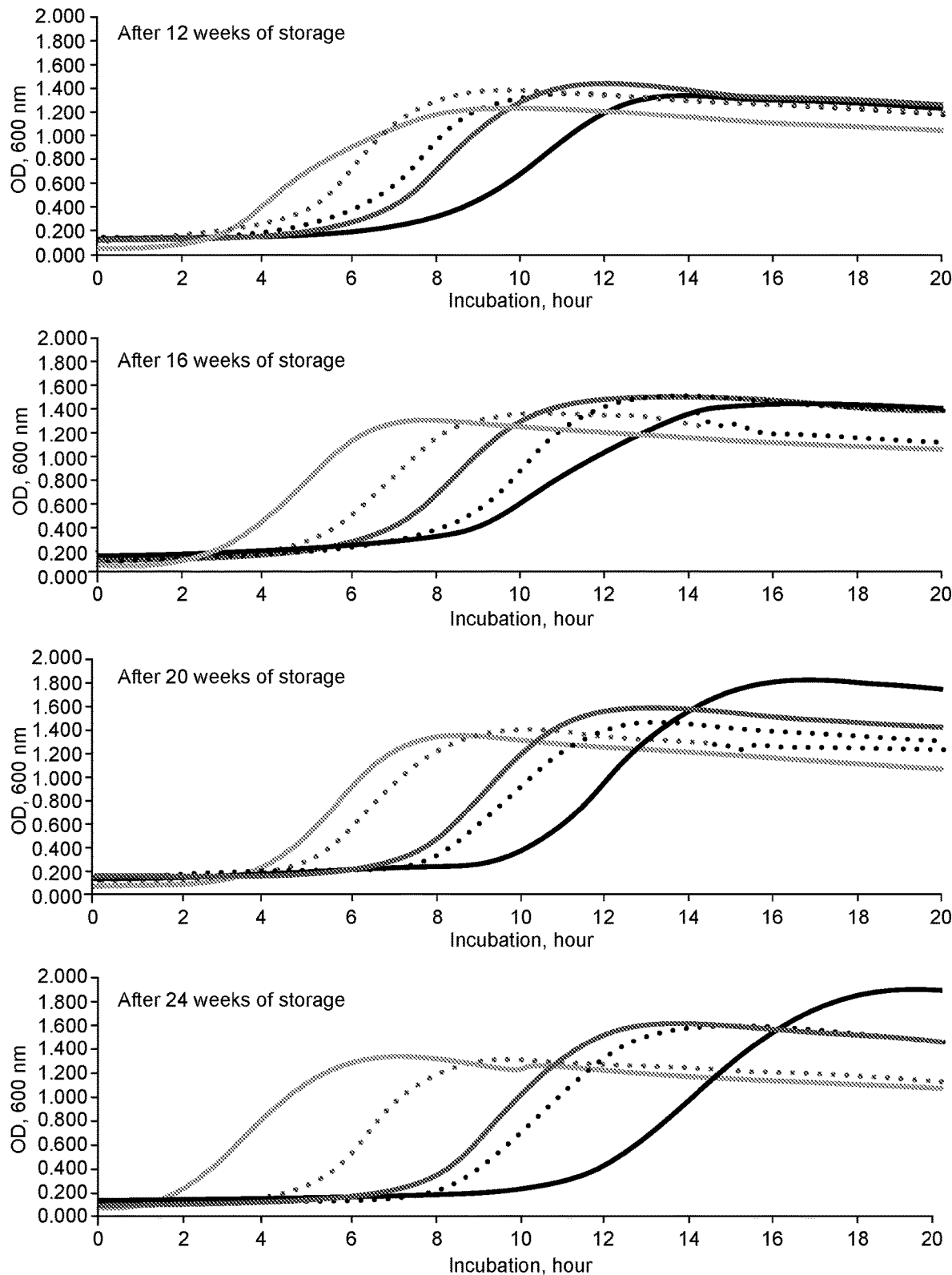

FIG. 24 shows growth curves performed on non-freeze-dried or rehydrated freeze-dried product obtained from 90% volume reduction retentate, mixed with 8% trehalose/15% skim milk (T/SM) or 8% maltodextrin/15% skim milk (M/SM), frozen in liquid nitrogen (LiqN), and freeze-dried using the rapid cycle after 12, 16, 20 or 24 weeks of storage under anaerobic conditions at 4 or 25° C. Optical density (OD) is shown at 600 nanometers (nm) as measured from 0 hours to 20 hours. Yellow lines=non-freeze-dried, Red lines=T/SM, Blue lines=M/SM, Dotted lines=stored at 4° C., and Full lines=stored at 25° C.

Figure 25:
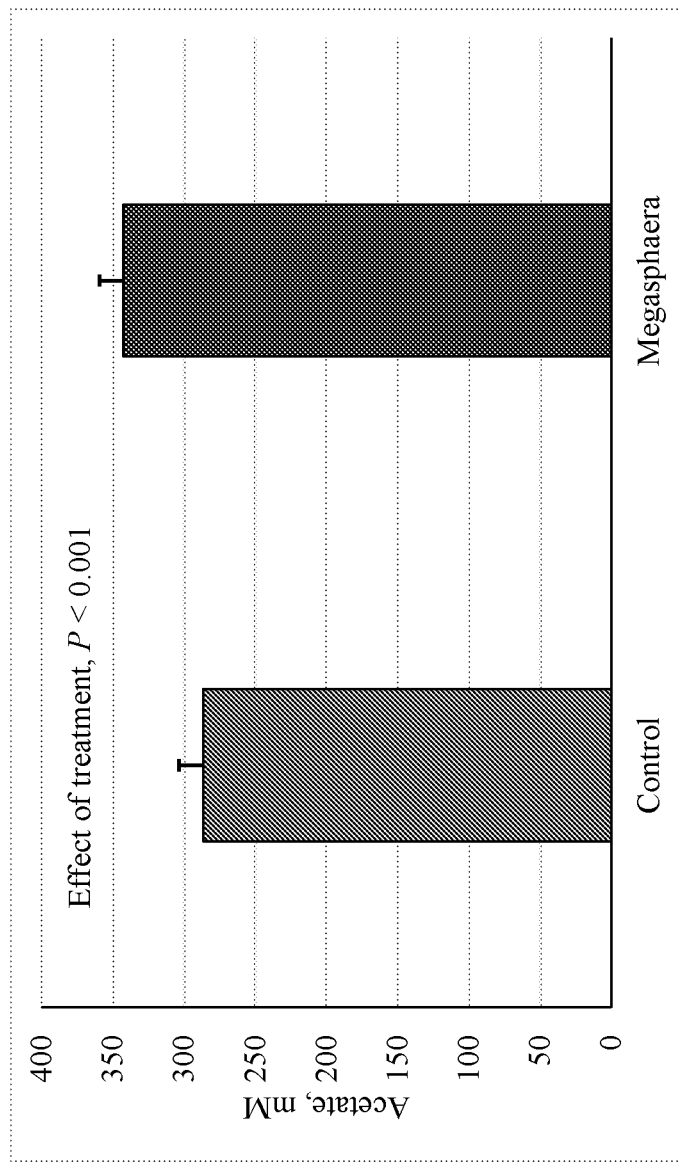

FIG. 25 shows the mean millimolar concentrations of acetate in a liquid extract of corn silage with no treatment (control/untreated) and *Megasphaera elsdenii*-treated corn silage after 120 days of ensiling.

Figure 26:
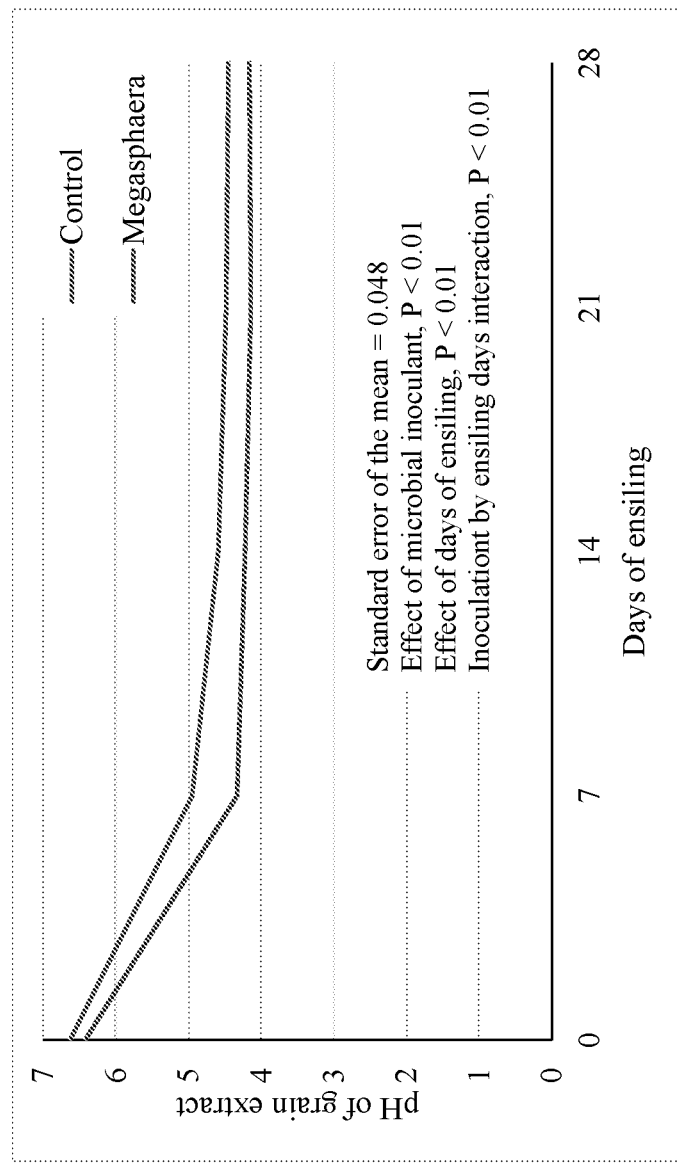

FIG. 26 shows the effect of treating reconstituted high-moisture corn with or without *Megasphaera elsdenii* on pH level during the ensiling process.

Figure 27:
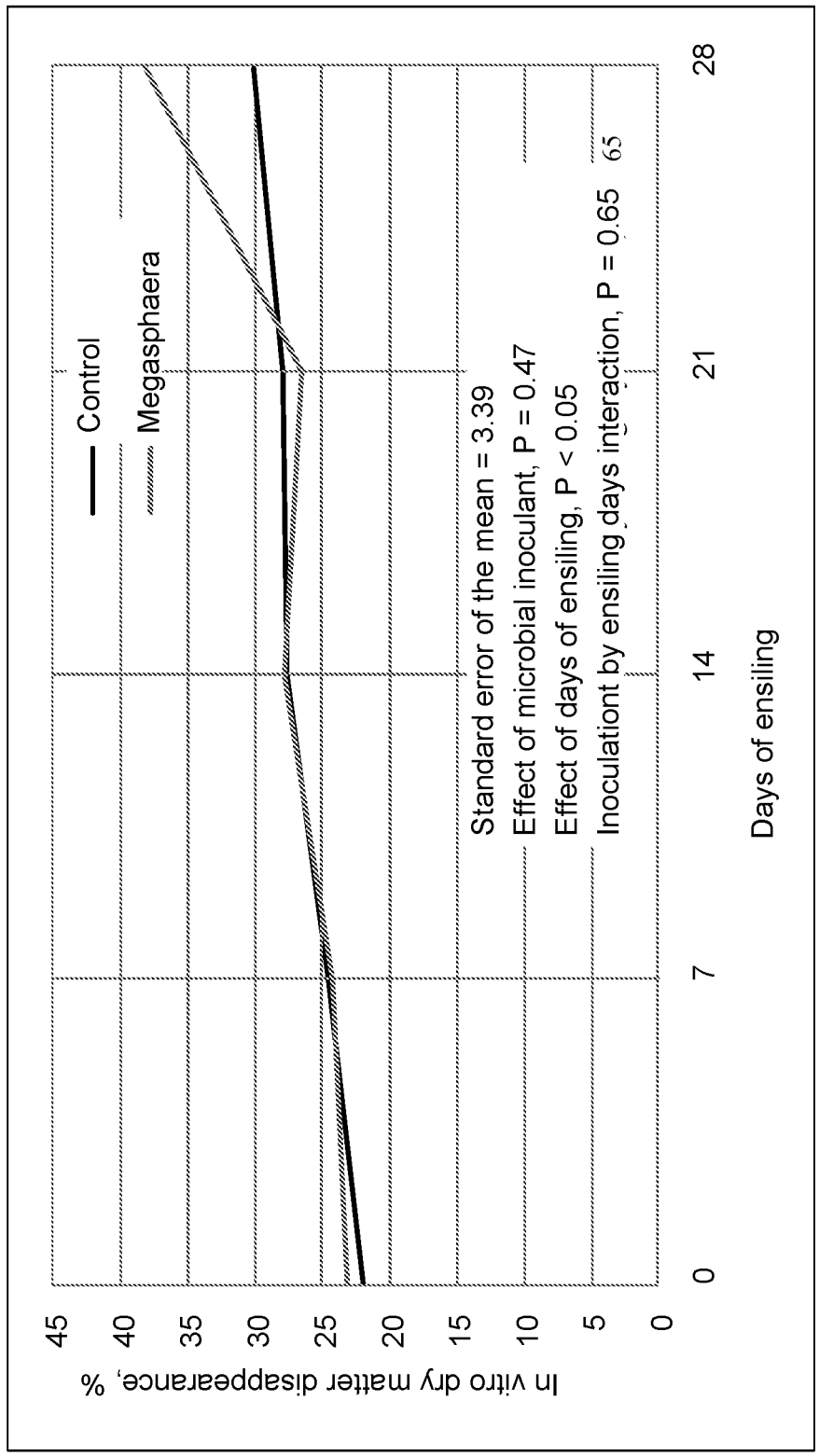

FIG. 27 shows the effect of dry matter content from in vitro cultures of mixed ruminal microbes containing reconstituted high-moisture corn with or without *Megasphaera elsdenii* treatment.

Figure 28:
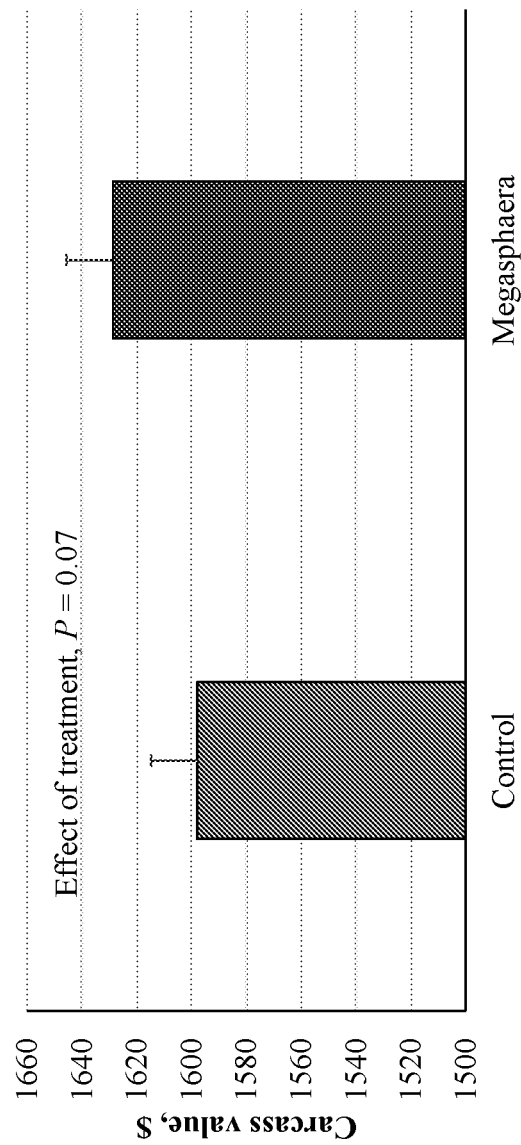

FIG. 28 shows the effect of carcass value when feeding cattle silage treated with *Megasphaera elsdenii* compared to untreated silage during the backgrounding phase (prior to finishing). Value of each carcass was calculated using a standardized grid that was constructed by averaging weekly USDA pricing data for premiums and discounts reported for the 10-year period between January 2008 to January 2018.

DETAILED DESCRIPTION OF THE INVENTION

The present invention relates to methods of using *Megasphaera elsdenii* cells to produce ensiled plant materials. The present invention also relates to the ensiled plant materials produced by the methods.

All publications, patents, and other references mentioned herein are incorporated by reference in their entireties for all purposes as if each individual publication or patent application were specifically and individually indicated to be incorporated by reference. In addition, citation or identification of any reference in this application shall not be construed as an admission that such reference is available as prior art to the present invention.

Terminology

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular.

To the extent that section headings are used, they should not be construed as necessarily limiting.

As used herein and in the appended claims, the singular forms "a," "an," and "the" include plural references unless the context clearly dictates otherwise. For example, the term "a compound" or "at least one compound" may include a plurality of compounds, including mixtures thereof. The terms "a", "an," "the," "one or more," and "at least one," for example, can be used interchangeably herein.

As used herein, the term "about," when used to modify an amount related to the invention, refers to variation in the numerical quantity that can occur, for example, through routine testing and handling; through inadvertent error in such testing and handling; through differences in the manufacture, source, or purity of ingredients employed in the invention; and the like. Whether or not modified by the term "about", the claims include equivalents of the recited quantities. In some embodiments, the term "about" means plus or minus 10% of the reported numerical value.

Throughout this application, various embodiments of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range, such as from 1 to 6 should be considered to have specifically disclosed subranges such as from 1 to 2, from 1 to 3, from 1 to 4, from 1 to 5, from 2 to 3, from 2 to 4, from 2 to 5, from 2 to 6, from 3 to 4, from 3 to 5, from 3 to 6, etc., as well as individual numbers within that range, for example, 1, 2, 3, 4, 5, and 6. This applies regardless of the breadth of the range.

The terms "comprises," "comprising," "includes," "including," "having," and their conjugates are interchangeable and mean "including but not limited to." It is understood that wherever aspects are described herein with the language "comprising," otherwise analogous aspects described in terms of "consisting of" and/or "consisting essentially of" are also provided.

The term "consisting of" means "including and limited to."

The term "consisting essentially of" means the specified material of a composition, or the specified steps of a method, and those additional materials or steps that do not materially affect the basic characteristics of the material or method.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "plant material" as used herein, means any plant material that can be used as an animal food and that can be ensiled, including, but not limited to, a forage, crop, grass, legume, grain, fruit, vegetable, or combinations thereof. Reference to a "plant material" or a particular type of plant material disclosed herein (e.g., a forage, crop, grass, legume, grain, cereal grain, fruit, vegetable, or combinations thereof) includes processed plant material (including, but not limited to, cut, chopped, shredded, or mown plant material, or combinations thereof), as well as parts of a plant material, including, but not limited to, stems, stalks, leaves, skins, husks, cobs, ears, grains, crop residues, or combinations thereof.

The terms "culture," "to culture," and "culturing," as used herein, means to incubate cells under in vitro conditions that allow for cell growth or division or to maintain cells in a living state. The term "a culture" can also be used herein to refer to cells incubated under in vitro conditions (e.g., cells incubated in a liquid growth media). The terms "growth media" and "culture media" as used herein refer to a solid (e.g., agar), semi-solid (e.g., agar), or liquid (e.g., broth) composition that contains components to support the growth of cells.

The term "additive" as used herein refers to one or more ingredients, products, or substances (e.g., cells), used alone or together (e.g., to improve the quality of an ensiled plant material, to improve an animal's performance and health, and/or to enhance digestibility of an ensiled plant material).

The terms "harvest" and "harvesting" as used herein with respect to cells refer to collecting cells from a culture, e.g., collecting cells in growth media from the culture, collecting cells by removing an amount of the growth media from the cells (e.g., by concentrating the cells in a liquid culture or separating the cells from the growth media), or halting the culturing of the cells. The terms include collecting or removing a volume of liquid comprising the cells from a liquid culture, including a volume in which the cells have been concentrated. The terms "harvest," "harvesting," and "collecting" as used herein with respect to a plant material refer to collection of plant materials by any manual or mechanical means.

The term "isolated" as used herein does not necessarily reflect the extent to which an isolate has been purified, but indicates isolation or separation from a native form or native environment. An isolate can include, but is not limited to, an isolated microorganism, an isolated biomass, or an isolated culture.

The term "effective amount" as used herein refers to an amount that achieves a desired result.

As used herein, "excipient" refers to a component, or mixture of components, that is used to give desirable characteristics to an ensiled plant material as disclosed herein. An excipient of the present invention can be described as a "pharmaceutically acceptable" excipient, meaning that the excipient is a compound, material, composition, salt, and/or dosage form which is, within the scope of sound medical judgment, suitable for contact with tissues of animals (i.e., humans and non-human animals) without excessive toxicity, irritation, allergic response, or other problematic complications over the desired duration of contact commensurate with a reasonable benefit/risk ratio.

As used herein, the term "yield" refers to the amount of living, or viable, cells, including the amount in a particular volume (e.g., colony-forming units per milliliter ("CFU/mL")) or in a particular weight (e.g., CFU per gram ("CFU/g")).

As used herein, the term "viable" refers to a living organism or organisms (e.g., a microbial cell that is alive or microbial cells that are alive). "Viability" refers to the ability to live, especially under certain conditions.

As used herein, "purify," "purified," and "purification" mean to make substantially pure or clear from unwanted components, material defilement, admixture or imperfection.

The terms "invention" and "disclosure" can be used interchangeably when describing or used, for example, in the phrases "the present invention" or "the present disclosure."

It is appreciated that certain features of the invention, which are, for clarity, described in the context of separate embodiments, can also be provided in combination in a single embodiment. Conversely, various features of the invention, which are, for brevity, described in the context of a single embodiment, can also be provided separately or in any suitable subcombination or as suitable in any other described embodiment of the invention. Certain features described in the context of various embodiments are not to be considered essential features of those embodiments, unless the embodiment is inoperative without those elements.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

Methods of Producing Ensiled Plant Materials

In one aspect, the present invention is directed to a method of producing an ensiled plant material with improved aerobic stability, comprising: (a) applying an effective amount of *M. elsdenii* cells to a plant material, and (b) ensiling the plant material to produce an ensiled plant material, wherein the ensiled plant material comprises improved aerobic stability as compared to a control ensiled plant material produced in the absence of the *M. elsdenii* cells. In some embodiments, the improved aerobic stability comprises a decreased pH, a decreased weight loss, or both.

In another aspect, the present invention is directed to a method of producing an increased amount of an ensiled plant material, comprising: (a) applying an effective amount of *M. elsdenii* cells to a plant material, and (b) ensiling the plant material to produce an ensiled plant material, wherein the amount of the ensiled plant material produced is increased as compared to the amount of a control ensiled plant material produced in the absence of the *M. elsdenii* cells. The amount of the ensiled plant material can be determined, for example, by weighing the ensiled plant material, or weighing a container that contains the ensiled plant material and subtracting the weight of the container.

In another aspect, the present invention is directed to a method of producing an ensiled plant material comprising: (a) applying *M. elsdenii* cells to a plant material, wherein the cells are selected from the group consisting of: ATCC® 25940, ATCC® 17752, ATCC® 17753, NCIMB 702261, NCIMB 702262, NCIMB 702264, NCIMB 702331, NCIMB 702409, NCIMB 702410, NCIMB 41125, NCIMB 41787, NCIMB 41788, NRRL 18624, NIAH 1102, and combinations thereof, and (b) ensiling the plant material to produce an ensiled plant material.

The plant material in the methods of the present invention includes any plant material that can be ensiled for the production of an ensiled plant material.

In some embodiments, the plant material in the methods of the present invention is any plant material consumed by a ruminant. In some embodiments, the ruminant can be, but is not limited to, cattle, buffalo, sheep, goats, deer, reindeer, moose, giraffe, yaks, and elk. In some embodiments, the ruminant is selected from the group consisting of: cattle, buffalo, sheep, goats, deer, and reindeer. In some embodiments, the plant material in the methods of the present invention is any plant material consumed by a camelid. In some embodiments, the camelid can be, but is not limited to, alapacas, llamas, guanaco, vicuñas, and camels.

In some embodiments, the plant material is selected from the group consisting of: a forage, crop, grass, legume, grain, fruit, vegetable, or combinations thereof. In some embodiments, the plant material is corn (i.e., maize), alfalfa, wheat, rye, barley, oats, triticale, millet, clover, sorghum, or combinations thereof. In some embodiments, the plant material is a crop residue such as, but not limited to, sorghum, corn stover, or soybean stover. In some embodiments, the plant material is a weed. In some embodiments, the plant material is a mixture of a grass and a legume, including one or more grasses and one or more legumes.

Grasses include, but are not limited to: *Agrostis* spp.—bentgrasses (e.g., *Agrostis capillaris*—common bentgrass and *Agrostis stolonifera*—creeping bentgrass); *Andropogon hallii*—sand bluestem; *Arrhenatherum elatius*—false oatgrass; *Bothriochloa bladhii*—Australian bluestem; *Bothriochloa pertusa*—hurricane grass; *Brachiaria decumbens*—Surinam grass; *Brachiaria humidicola*—koronivia grass; *Bromus* spp.—bromegrasses; *Cenchrus ciliaris*—buffelgrass; *Chloris gayana*—Rhodes grass; *Cynodon dactylon*—bermudagrass; *Dactylis glomerata*—orchard grass; *Echinochloa pyramidalis*—antelope grass; *Entolasia imbricata*—bungoma grass; *Festuca* spp.—fescues (e.g., *Festuca arundinacea*—tall fescue, *Festuca pratensis*—meadow fescue, and *Festuca rubra*—red fescue); *Heteropogon contortus*—black spear grass; *Hymenachne amplexicaulis*—West Indian marsh grass; *Hyparrhenia rufa*—jaragua; *Leersia hexandra*—southern cutgrass; *Lolium* spp.—ryegrasses (e.g., *Lolium multiflorum*—Italian ryegrass and *Lolium perenne*—perennial ryegrass); *Megathyrsus maximus*—Guinea grass; *Melinis minutiflora*—molasses grass; *Paspalum dilatatum*—dallisgrass; *Phalaris arundinacea*—reed canarygrass; *Phleum pratense*—timothy; *Poa* spp.—bluegrasses, meadow-grasses (e.g., *Poa arachnifera*—Texas bluegrass, *Poa pratensis*—Kentucky bluegrass, and *Poa trivialis*—rough bluegrass); *Setaria sphacelata*—African bristlegrass; *Themeda triandra*—kangaroo grass; and *Thinopyrum* intermedium—intermediate wheatgrass.

Legumes include, but are not limited to, herbaceous legumes and tree legumes. Herbaceous legumes include, but are not limited to: *Arachis pintoi*—pinto peanut; *Chamaecrista rotundifolia*—roundleaf sensitive pea; *Clitoria ternatea*—butterfly-pea; *Lotus corniculatus*—bird's-foot trefoil; *Macroptilium atropurpureum*—purple bush-bean; *Macroptilium bracteatum*—burgundy bean; *Medicago* spp.—medics (e.g., *Medicago sativa*—alfalfa, lucerne, and *Medicago truncatula*—barrel medic); *Melilotus* spp.—sweetclovers; *Neonotonia wightii*—perennial soybean; *Onobrychis viciifolia*—common sainfoin; *Stylosanthes* spp.—stylo (e.g., *Stylosanthes humilis*—Townsville stylo); *Stylosanthes scabra*—shrubby stylo; *Trifolium* spp.—clovers (e.g., *Trifolium hybridum*—alsike clover, *Trifolium incarnatum*—crimson clover, *Trifolium pratense*—red clover, *Trifolium repens*—white clover); and *Vicia* spp.—vetches (e.g., *Vicia articulata*—oneflower vetch, *Vicia ervilia*—bitter vetch, *Vicia narbonensis*—narbon vetch, *Vicia sativa*—common vetch, tare, *Vicia villosa*—hairy vetch); and *Vigna parkeri*—creeping vigna). Tree legumes include, but are not limited to: *Acacia aneura*—mulga; *Albizia* spp.—silk trees; *Albizia canescens*—Belmont siris; *Albizia lebbeck*—lebbeck; *Enterolobium cyclocarpum*—earpodtree; and *Leucaena leucocephala*—leadtree.

In some embodiments, the plant material in the methods of the present invention is a plant material comprising a moisture content of about 30% to about 90%, about 35% to about 85%, about 40% to about 80%, about 40% to about 75%, about 40% to about 70%, about 40% to about 65%, about 40% to about 60%, about 45% to about 80%, about 45% to about 75%, about 45% to about 70%, about 45% to about 65%, about 50% to about 80%, about 50% to about 75%, about 50% to about 70%, about 50% to about 65%, or about 50% to about 60%.

Plant material can be harvested or collected at any suitable time, for example, when the moisture is at a suitable level. If the moisture level is too high, the plant material can be, for example, allowed to wilt until the moisture is at a suitable level.

In some embodiments, a previously dehydrated plant material (e.g., a dried grain) can be rehydrated for use in the ensiling according to any of the methods of the present invention.

The ensiling in any of the methods of the present invention can be according to any standard or known method of ensiling a plant material. The plant material in the methods of the present invention is ensiled in a sealed container, also referred to herein as a "silo," to allow anaerobic fermentation of the plant material.

In some embodiments, the methods of the present invention further comprise applying an additive to the plant material.

In some embodiments, the applying in any of the methods of the present invention (i.e., the applying of *Megasphaera elsdenii* cells, the applying of an additive, or both) is before harvesting of the plant material, after harvesting of the plant material, at the time of ensiling, or combinations thereof. When both *Megasphaera elsdenii* cells and additives are applied, they can be applied together, or separately at the same or different times.

The additive in the methods of the present invention can be any additive used in an ensiling process or applied to ensiled plant material.

In some embodiments, the additive in the methods of the present invention is selected from the group consisting of: a microorganism, enzyme, fermentable substrate, acid, preservative, nutrient, and combinations thereof.

In some embodiments, the additive in the methods of the present invention is a fermentable carbohydrate, including, but not limited to, a sugar source such as, but not limited to, Molasses, sucrose, glucose, dextrose, whey, cereal grains, rice bran, wheat bran, citrus pulp, pineapple pulp, or beet pulp.

In some embodiments, the additive in the methods of the present invention is an enzyme such as, but not limited to, a cellulase, hemicellulase, amylase, pectinase, protease, or xylanase.

In some embodiments, the additive in the methods of the present invention is a microorganism that stimulates fermentation such as, but not limited to, a lactic acid bacteria. In some embodiments, the microorganism is a *Lactobacillus, Pediococcus, Enterococcus, Propionibacterium, Lactococcus, Streptococcus, Leuconostoc*, or *Selenomonas*. In some embodiments, the microorganism is *Lactobacillus plantarum, Lactobacillus acidophilus, Lactobacillus buchneri, Lactobacillus casei, Lactobacillus cornyiformis, Lactobacillus curvatus, Lactobacillus salivarus, Lactobacillus brevis, Lactobacillus fermentum, Lactobacillus viridescens, Pediococcus acidilactici, Pediococcus pentocaceus, Pediococcus cerevisiae, Enterococcus faecium, Enterococcus faecalis, Propionibacterium jensenii, Propionibacterium acidipropionici, *Propionibacterium freudenreichii, Propionibacterium globosum, Propionibacterium shermanii, Lactococcus lactis, Streptococcus bovis, Leuconostoc mesenteroides*, or *Selenomonas ruminantium*.

In some embodiments, the additive in the methods of the present invention is an inhibitor of fermentation, including, but not limited to, acids and organic salts such as, but not limited to, mineral acids (e.g., hydrochloric acid), formic acid, acetic acid, caproic acid, sorbic acid, benzoic acid, sulfuric acid, lactic acid, acrylic acid, calcium formate, propionic acid, or proprionates, or other chemical inhibitors such as, but not limited to, formaldehyde, paraformaldehyde, sodium nitrite, sodium metabisulphite sulfur dioxide, sodium hydroxide, sodium sulfate, sodium chloride, urea, or ammonia.

In some embodiments, the additive in the methods of the present invention is an aerobic spoilage inhibitor, such as, but not limited to, propionic acid, proprionates, acetic acid, caproic acid, or ammonia.

In some embodiments, the additive in the methods of the present invention is a nutrient or nutrient source, such as, but not limited to, urea, ammonia, limestone, or other mineral.

In some embodiments, the additive in the methods of the present invention is an absorbent, such as, but not limited to, a grain, straw, bentonite, sugar beet pulp, or polyacrylamide.

In some embodiments, an effective amount of *Megasphaera elsdenii* in the methods of the present invention is at least about $10^6$, at least about $10^7$, at least about $10^8$, at least about $10^9$, at least about $10^{10}$, about $10^6$ to about $10^{14}$, about $10^6$ to about $10^{13}$, about $10^6$ to about $10^{12}$, about $10^6$ to about $10^{11}$, about $10^7$ to about $10^{14}$, about $10^7$ to about $10^{13}$, about $10^7$ to about $10^{12}$, about $10^7$ to about $10^{11}$, about $10^8$ to about $10^{11}$, about $10^9$ to about $10^{11}$, about $10^{10}$ to about $10^{11}$, about $10^{10}$ to about $10^{12}$, about $10^{10}$ to about $10^{13}$, or about $10^{10}$ to about $10^{14}$ colony forming units (CFU) per ton of plant material.

In some embodiments, the *M. elsdenii* cells the methods of the present invention are selected from the group consisting of: ATCC® 25940, ATCC® 17752, ATCC® 17753, NCIMB 702261, NCIMB 702262, NCIMB 702264, NCIMB 702331, NCIMB 702409, NCIMB 702410, NCIMB 41125, NCIMB 41787, NCIMB 41788, NRRL 18624, NIAH 1102, and combinations thereof.

In some embodiments, the *M. elsdenii* cells in the methods of the present invention are *M. elsdenii* NCIMB 41125 cells.

In some embodiments, the methods of the present invention comprise applying the *M. elsdenii* cells in a liquid.

In some embodiments, the methods of the present invention comprise applying the *M. elsdenii* cells as freeze-dried cells. In some embodiments, a dry carrier comprises the freeze-dried cells. In some embodiments, a dry carrier includes, but is not limited to, calcium carbonate, dried milk, or sucrose.

In some embodiments, the methods of the present invention further comprise mixing freeze-dried *M. elsdenii* cells with a liquid prior to applying the cells.

In some embodiments, the methods of the present invention comprise applying an additive in a liquid. When both the *M. elsdenii* cells and additive are applied in a liquid, they can be applied in separate liquids, can be applied in separate liquids at separate times or at the same time, or can be applied as a mixture in the same liquid.

In some embodiments, the methods of the present invention comprise applying an additive in a dry form, such as, but not limited to, a powder, granules, or freeze-dried forms. When in dry form, the additive can be mixed with a dry carrier. When both the *M. elsdenii* cells and additive are applied in a dry form, they can be in separate dry forms, can be applied in separate dry forms at separate times or at the same time, or can be applied as a mixture of dry forms, including mixtures of dry forms in a dry carrier.

In another aspect, the present invention is directed to an ensiled plant material produced by any of the methods of the present invention.

*Megasphaera elsdenii*

*Megasphaera elsdenii* cells from any strain or any combination of strains can be used in the invention described herein.

A *M. elsdenii* strain or strains can be selected from a stock culture collection (e.g., American Type Culture Collection ("ATCC®"), National Collection of Industrial, Food and Marine Bacteria ("NCIMB"), National Collection of Type Cultures ("NCTC"), American Research Service ("ARC") culture collection (i.e., "NRRL"), National Institute of Animal Health (NIAH) culture collection), or can be a strain that has been isolated from a natural source (e.g., from the gastrointestinal tract of a ruminant).

Examples of *M. elsdenii* strains that can be selected from a culture collection include, but are not limited to, the strains listed by deposit numbers in Table 1. Alternative designations of the deposit numbers are also indicated.

TABLE 1

Examples of *M. elsdenii* Strains and Source of Each Strain.

| Deposit Number | Alternative Designations | Source of Strain |
|---|---|---|
| ATCC ® 25940 | NCIMB 8927; BE2-2083 | Rumen of Sheep |
| ATCC ® 17752 | B159; NCIMB 702409; NCDO2409 | N/A |
| ATCC ® 17753 | T81; NCIMB 702410; NCDO2410 | N/A |
| NCIMB 702261 | A17-2; A12-2; NCDO2261 | Human Adult Faeces |
| NCIMB 702262 | S17-3; NCDO2262 | Juvenile Swine Faeces |
| NCIMB 702264 | LC1 | N/A |
| NCIMB 702331 | LC1; NCDO2263; NCDO2264; NCDO2331; | N/A |
| NCIMB 41125 | | Rumen of Dairy Cow |
| NCIMB 41787 | | Rumen of Dairy Cow |
| NCIMB 41788 | | Rumen of Dairy Cow |
| NRRL 18624 | | Rumen of Bovine |
| NIAH 1102 | | N/A |

In some embodiments, the *M. elsdenii* cells are from a strain having a deposit number selected from the group consisting of: ATCC® 25940, ATCC® 17752, ATCC® 17753, NCIMB 702261, NCIMB 702262, NCIMB 702264, NCIMB 702331, NCIMB 702409, NCIMB 702410, NCIMB 41125, NCIMB 41787, NCIMB 41788, NRRL 18624, NIAH 1102, and combinations thereof, including any of the alternative designations in Table 1.

In some embodiments, the *M. elsdenii* cells are from a strain isolated from a ruminant (e.g., a cow). See, e.g., U.S. Pat. No. 7,550,139.

In some embodiments, the *M. elsdenii* cells are from a strain isolated from a non-ruminant (e.g., a human).

In some embodiments, the *M. elsdenii* cells are from a strain selected for lactate utilization (e.g., a strain that utilizes lactate in the presence of sugars), resistance to ionophore antibiotics, relatively high growth rate, capability to produce predominantly acetate, capability to proliferate at pH values below 5.0 and as low as 4.5, production of volatile fatty acids (VFAs), phytase activity, and combinations thereof. See, e.g., U.S. Pat. No. 7,550,139.

In some embodiments, a strain selected for lactate utilization utilizes lactate as a preferred carbon source in the presence of a soluble carbohydrate (e.g., glucose and/or maltose). Lactate utilization can be determined, for example, based on growth in a medium containing lactate and lacking soluble carbohydrates as compared to the same medium supplemented with soluble carbohydrates.

In some embodiments, the *M. elsdenii* cells are from a strain with a high growth rate as compared to other strains. The growth rates of different strains can be determined, for example, by culturing the cells in a liquid medium and monitoring the increase in optical density over time.

In some embodiments, the *M. elsdenii* cells are from a strain capable of producing VFAs, which can be determined, for example, by gas chromatography. In some embodiments, the VFA is a 6-carbon fatty acid.

In some embodiments, the *M. elsdenii* cells are from *Megasphaera elsdenii* strain NCIMB 41125. This strain of *Megasphaera elsdenii* has a high specific growth rate (0.94 generations/hour), is capable of growth in a pH range of 4.5 to 6.5 or more, uses D- and L-Lactate as its preferred substrate, but also has the ability to utilize glucose and other carbohydrates, and tolerates ionophores.

In some embodiments, the *M. elsdenii* cells are from *Megasphaera elsdenii* strain NCIMB 41787. In some embodiments, the *M. elsdenii* cells are from *Megasphaera elsdenii* strain NCIMB 41788.

In some embodiments, the *M. elsdenii* cells are from *Megasphaera elsdenii* strain ATCC® 25940.

In some embodiments, the *M. elsdenii* cells are derived from a strain selected from a stock culture collection or isolated from a natural source. Cells that are "derived" from a strain can be a natural or artificial derivative such as, for example, a sub isolate, a mutant, variant, or recombinant strain.

In some embodiments, the *M. elsdenii* cells are a commercial preparation such as a Lactipro® product (e.g., Lactipro Advance®, MSBiotec®, Wamego, Kansas).

Preparing a Culture Comprising *Megasphaera elsdenii* Cells

*M. elsdenii* cells for use herein can be grown in a liquid culture and used directly as a liquid culture. Alternatively, the cells can be isolated from a liquid or solid culture and either resuspended in a suitable liquid or freeze-dried prior to use.

*M. elsdenii* is an anaerobic bacterium that must be cultured under strict anaerobic conditions in order to obtain maximum yield and viability.

In some embodiments, a culture comprises *M. elsdenii* cells and a growth media.

In some embodiments, the culture comprises one or more strains of *M. elsdenii* cells. In some embodiments, the culture comprises a single strain of *M. elsdenii* cells. In some embodiments, the culture consists of one or more strains of *M. elsdenii* cells (i.e., the cells in the culture consist of *M. elsdenii* cells, e.g., one or more strains of *M. elsdenii* cells). In some embodiments, the culture consists of a single strain of *M. elsdenii* cells.

In some embodiments, the methods of the present invention can also include growing, harvesting, and/or freeze-drying *M. elsdenii* cells for use in the methods.

Various fermentation parameters for inoculating, growing, and harvesting *M. elsdenii* cells can be used, including continuous fermentation (i.e., continuous culture) or batch fermentation (i.e., batch culture). See, for example, U.S. Pat. No. 7,550,139.

Growth media for *M. elsdenii* cells can be a solid, semi-solid, or liquid. A medium can contain nutrients that provide essential elements and specific factors that enable growth. A variety of microbiological media and variations are well known in the art. Media can be added to a culture at any time, including the start of the culture, during the culture, or intermittently/continuously.

Examples of growth media include, but are not limited to: (1) semi-defined media, which contains peptone, 3 g/L; yeast, 3 g/L; vitamin solution, 2 mL/L; mineral solution, 25 mL/L; indigo carmine (0.5%), 1 g/L; 12.5% L-cysteine, 2 g/L; 12.5% sodium sulfide, 2 g/L; and supplemented with either Na-lactate (semi-defined lactate, SDL), glucose (semi-defined glucose, SDG), or maltose(semi-defined maltose, SDM); (2) Modified Reinforced Clostridial Agar/Broth Medium (pre-reduced), which contains peptone, 10 g/L; beef extract, 10 g/L; yeast extract, 3 g/L; dextrose 5 g/L; NaCl, 5 g/L; soluble starch, 1 g/L; L-cysteine HCl, 0.5 g/L; sodium acetate, 3 g/L; and resazurin (0.025%), 4 mL/L; (3) Trypticase soy agar/broth with defibrinated sheep blood; (4) semi-defined rumen fluid free medium, which contains Na-lactate (70%), 10 g/l; Peptone, 2 g/l; $KH_2PO_4$ 1 g/l; $(NH_4)_2SO_4$ 3 g/l; $MgSO_4$ $7H_2O$ 0.2 g/l; $CaCl_2.2H_2O$ 0.06 g/l; Vitamins (Pyridoxolhydrochloride, 4 mg/l; Pyridoxamine, 4 mg/l; Riboflavin, 4 mg/l; Thiaminiumchloride, 4 mg/l; Nicotinamide, 4 mg/l; Ca-D-pantothenate, 4 mg/l; 4-Aminobenzoic acid, 0.2 mg/l, Biotin, 0.2 mg/l, Folic acid, 0.1 mg/l and Cyanocobalamin, 0.02 mg/l); $Na_2S.9H_2O$, 0.25 g/l; Cysteine, 0.25 g/l; Antifoam, 0.07 ml/l and Monensin, 10 mg/l; and which is prepared by adding the Na-lactate and mineral solution to a reservoir bottle and autoclaving for 60 minutes; dissolving the peptone in 300 ml distilled H2O and autoclaving separately; filter sterilizing the vitamin solution and two reducing agents beforehand; following autoclaving, gassing the reservoir bottle with anaerobic gas overnight; adding the other constituents separately after cooling; and adjusting the pH to the desired value with 5N HCl; and (5) incubated rumen fluid lactate ("IRFL") medium, which contains 400 ml incubated clarified rumen fluid from lucerne-fed sheep, 371 ml distilled water, 2 g peptone, 15 g agar, 100 ml 10% (w/v) sodium-D, L-lactate solution, 100 ml 0.04% (w/v) bromocresol purple solution, and 25 ml mineral solution containing 40 g/l $KH_2PO_4$; 120 g/l $(NH_4)_2SO_4$; 8 g/l $MgSO_4.7H_2O$ and 2.4 g/l $CaCl_2.2H_2O$, where lactic acid (90% w/v) is used to adjust the pH to 5.5 before autoclaving at 121° C. for 25 minutes, then cooling in a 50° C. water bath while being gassed with an anaerobic gas mixture, followed by adding two milliliters of each of $Na_2S.9H_2O$ (12.5% w/v) and cysteine.$HCl.H_2O$ (12.5% w/v).

In some embodiments, the culture comprises a growth media comprising at least two carbon sources. In some embodiments, the at least two carbon sources are selected from the group consisting of: casein, starch (e.g., gelatinized starch and/or soluble starch), lactate (i.e., lactic acid), dextrose, fructose, fructan, glucose, sucrose, lactose, maltose, acetate, glycerol, mannitol, saccharose, xylose, molasses, fucose, glucosamine, dextran, a fat, an oil, glycerol, sodium acetate, arabinose, soy protein, soluble protein, raffinose, and combinations there.

In some embodiments, the at least two carbon sources consist of about 1-99% of a first carbon source (e.g., any carbon source described herein) and about 1-99% of a second carbon source (e.g., any carbon source described herein that is different from the first carbon source), wherein 100% of the at least two carbon sources consist of the first carbon source and the second carbon source. In some embodiments, the at least two carbon sources consist of about 50-60% of the first carbon source and about 40-50% of the second carbon source, about 50-70% of the first carbon source and about 30-50% of the second carbon source, about 50-80% of the first carbon source and about 20-50% of the second carbon source, or about 50-90% of the first carbon source and about 10-50% of the second carbon source. In other embodiments, the at least two carbon sources consist of about 65-75% of the first carbon source and about 25-35% of the second carbon source. In some embodiments, the first carbon source is lactate.

In some embodiments, the *M. elsdenii* cells are grown at about 39° C. to about 40° C., at about 35° C., at about 36° C., at about 37° C., at about 38° C., at about 39° C., or at about 40° C.

In some embodiments, the *M. elsdenii* cells are cooled to about 18° C. to about 25° C. for storage.

In some embodiments, the pH of the culture comprising the *M. elsdenii* cells (e.g., during the culturing and/or at the time of harvesting) is between about 4.5 to about 7.0, between about 4.5 to about 6.5, between about 4.5 to about 6.0, between about 4.5 to about 5.5, between about 4.5 to about 5.0, between about 4.6 to about 6.9, between about 4.7 to about 6.8, between about 4.8 to about 6.7, between about 4.9 to about 6.6, between about 5.0 to about 7.0, between about 5.0 to about 6.5, between about 5.0 to about 6.0, between about 5.0 to about 5.5, between about 5.1 to about 6.9, between about 5.2 to about 6.8, between about 5.3 to about 6.7, between about 5.4 to about 6.6, between about 5.5 to about 7.0, between about 5.5 to about 6.5, between about 5.1 to about 6.4, between about 5.2 to about 6.3, between about 5.3 to about 6.2, between about 5.4 to about 6.1, between about 5.5 to about 6.0, between about 5.0 to about 6.1, between about 5.0 to about 6.2, between about 5.0 to about 6.3, between about 5.0 to about 6.4, between about 5.1 to about 6.5, between about 5.2 to about 6.5, between about 5.3 to about 6.5, or between about 5.4 to about 6.5.

To culture *M. elsdenii* cells, fermenters of different sizes and designs that maintain anaerobic conditions can be used. A fermenter can be capable, for example, of fermenting culture volumes sufficient for commercial production of *M. elsdenii* cells.

In some embodiments, a culture comprising *M. elsdenii* cells also comprises another microorganism (i.e., a microbial cell that is not a *M. elsdenii* cell). In some embodiments, a culture comprises *M. elsdenii* cells and another microorganism that is an obligate anaerobe. In some embodiments, the culture comprises *M. elsdenii* cells and another microorganism selected from the group consisting of: *Lactobacillus, Pediococcus, Enterococcus, Propionibacterium, Lactococcus, Streptococcus, Leuconostoc,* or *Selenomonas*.

Freeze-Dried *Megasphaera elsdenii* Cells

In some embodiments, the *Megasphaera elsdenii* cells for use in the methods and ensiled plant materials of the present invention are freeze-dried cells.

Freeze-dried *M. elsdenii* cells can be produced by a method comprising: preparing a culture comprising *M. elsdenii* cells and a growth media; harvesting the cells; freezing the cells; and freeze-drying the cells, wherein freeze-dried *M. elsdenii* cells are produced. In some embodiments, the method is performed in the order of preparing the culture, then harvesting the cells (i.e., harvesting the cultured cells), then freezing the cells (i.e., freezing the harvested cells), and then freeze-drying the cells (i.e., freeze-drying the frozen cells).

In some embodiments, the method is performed under anaerobic conditions. In some embodiments, the method comprises preparing the culture, harvesting the cells, freezing the cells, freeze-drying the cells, or combinations thereof under anaerobic conditions.

The method can comprise any of the methods of preparing a culture as described herein. A culture of the method also can comprise any of the properties of a culture described herein.

In some embodiments, the cells in the culture comprise *M. elsdenii* cells. In some embodiments, the cells in the culture consist of *M. elsdenii* cells.

In some embodiments, the growth media comprises at least two carbon sources selected from the group consisting of: casein, lactate (i.e., lactic acid), dextrose, fructose, fructan, glucose, sucrose, lactose, maltose, acetate, glycerol, mannitol, saccharose, xylose, molasses, fucose, glucosamine, dextran, a fat, an oil, glycerol, sodium acetate, arabinose, soy protein, soluble protein, raffinose, and combinations thereof.

In some embodiments, the method comprises harvesting the cells within 12 hours after the culture has ended its exponential growth phase. The culture can be cooled to room temperature to stop growth at the time of harvesting.

In some embodiments, the culture comprises a liquid, and the method comprises harvesting the *M. elsdenii* cells (e.g., concentrated *M. elsdenii* cells) with a percentage of the liquid. In some embodiments, the method comprises harvesting the cells with about 1% to about 40%, about 1% to about 35%, about 1% to about 30%, about 1% to about 25%, about 1% to about 20%, about 1% to about 15%, about 1% to about 10%, about 1% to about 5%, about 10%, about 9%, about 8%, about 7%, about 6%, about 5%, about 4%, about 3%, about 2%, or about 1% of the liquid. In some embodiments, the method comprises harvesting the cells with less that about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1% of the liquid.

In some embodiments, the culture comprises a liquid, and the method comprises harvesting the *M. elsdenii* cells (e.g., concentrated *M. elsdenii* cells) by removing a percentage of the liquid. In some embodiments, harvesting the cells comprises removing about 50% to about 100% of the liquid, about 55% to about 100%, about 60% to about 100%, about 65% to about 100%, about 70% to about 100%, about 75% to about 100%, about 80% to about 100%, about 85% to about 100%, about 90% to about 100%, or about 95% to about 100% of the liquid. In some embodiments, harvesting the cells comprises removing at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% of the liquid.

In some embodiments, the method comprises harvesting the *M. elsdenii* cells by concentrating the cells. In some embodiments, harvesting the cells comprises concentrating the cells by at least one technique selected from the group consisting of: centrifugation, filtration, dialysis, reverse osmosis, and combinations thereof. In some embodiments, the filtration comprises clay filtration. In some embodiments, the filtration comprises tangential flow filtration, also known as cross-flow filtration.

In some embodiments, the pH of the culture comprising the *M. elsdenii* cells at the time of harvesting is between about 4.5 to about 7.0, between about 4.5 to about 6.5, between about 4.5 to about 6.0, between about 4.5 to about 5.5, between about 4.5 to about 5.0, between about 4.6 to about 6.9, between about 4.7 to about 6.8, between about 4.8 to about 6.7, between about 4.9 to about 6.6, between about 5.0 to about 7.0, between about 5.0 to about 6.5, between about 5.0 to about 6.0, between about 5.0 to about 5.5, between about 5.1 to about 6.9, between about 5.2 to about 6.8, between about 5.3 to about 6.7, between about 5.4 to about 6.6, between about 5.5 to about 7.0, between about 5.5 to about 6.5, between about 5.1 to about 6.4, between about 5.2 to about 6.3, between about 5.3 to about 6.2, between about 5.4 to about 6.1, between about 5.5 to about 6.0, between about 5.0 to about 6.1, between about 5.0 to about 6.2, between about 5.0 to about 6.3, between about 5.0 to about 6.4, between about 5.1 to about 6.5, between about 5.2 to about 6.5, between about 5.3 to about 6.5, or between about 5.4 to about 6.5.

In some embodiments, the method comprises inoculating growth media in a fermenter with an inoculum comprising *M. elsdenii* cells to prepare a culture, and incubating the culture at a temperature of about 39° C. until the pH of the culture is about 6.0. In some embodiments, the inoculum comprising *M. elsdenii* cells is a flask culture of *M. elsdenii* cells or a portion thereof. In some embodiments, the method comprises inoculating growth media in a fermenter an inoculum to media ratio of 1/50 to 1/4,000. In some embodiments, the inoculum to media ration is 1/100.

In some embodiments, the culture further comprises at least one cryoprotectant. In some embodiments, the at least one cryoprotectant is selected from the group consisting of: fructose, glucose, sucrose, milk powder, infant formula, skim milk, trehalose, maltodextrin, betaine, and combinations thereof. In some embodiments, the at least one cryoprotectant is present in an amount of about 1% to about 50% (w/v) of the culture, about 1% to about 40% (w/v) of the culture, about 1% to about 30% (w/v) of the culture, about 1% to about 20% (w/v) of the culture, about 1% to about 10% (w/v) of the culture, about 1% to about 5% (w/v) of the culture, about 10% to about 20% (w/v) of the culture, about 15% to about 25% (w/v) of the culture, about 20% to about 30% (w/v) of the culture, about 30% to about 40% (w/v) of the culture, about 40% to about 50% (w/v) of the culture, about 60% to about 70% (w/v) of the culture, about 70% to about 80% (w/v) of the culture. In some embodiments, the cryoprotectant is added by adding powdered cryoprotectant directly to the concentrated *M. elsdenii* cells. In some embodiments, the cryoprotectant is added by adding a solution of cryoprotectant directly to the concentrated *M. elsdenii* cells at a ratio of 1/1, at a ratio of 1/5, or at a ratio of 1/10.

In some embodiments, freezing the cells comprises placing the cells in a freezer or contacting the cells with dry ice, liquid nitrogen, or a combination thereof. Freezing the cells includes freezing the cells while they are inside a container. Contacting the cells includes contacting a container comprising the cells with a medium for freezing the cells. A medium for freezing the cells includes, but is not limited to, a freezer, an acetone-dry ice bath, liquid nitrogen, or a combination thereof.

In some embodiments, the method comprises freezing the cells at a temperature of about −20° C. to about −210° C. In some embodiments, the method comprises freezing the cells at a temperature of about −20° C. to about −80° C. In some embodiments, the method comprises freezing the cells at a temperature of about −80° C. to about −210° C. In some embodiments, the method comprises freezing the cells at a temperature of about −20° C. to about −196° C. In some embodiments, the method comprises freezing the cells at a temperature of about −80° C. to about −196° C. In some embodiments, the method comprises freezing the cells at a temperature of about −20° C. In some embodiments, the method comprises freezing the cells at a temperature of about −80° C. In some embodiments, the method comprises freezing the cells at a temperature of about −196° C. In some embodiments, the method comprises freezing the cells by contacting the cells with liquid nitrogen.

In some embodiments, the method comprises freezing the cells under anaerobic conditions.

In some embodiments, the freezing produces frozen pellets comprising the cells. For example, the freezing can be achieved using a flash freezer.

In some embodiments, the diameter of the frozen pellets is about 0.001 to about 1.0 inches, about 0.01 to about 1.0 inches, about 0.1 to about 1.0 inches, about 0.2 to about 1.0 inches, about 0.3 to about 1.0 inches, about 0.4 to about 1.0 inches, about 0.5 to about 1.0 inches, about 0.6 to about 1.0 inches, about 0.7 to about 1.0 inches, about 0.8 to about 1.0 inches, about 0.9 to about 1.0 inches, about 0.001 to about 0.9 inches, about 0.01 to about 0.9 inches, about 0.1 to about 0.9 inches, about 0.2 to about 0.9 inches, about 0.3 to about 0.9 inches, about 0.4 to about 0.9 inches, about 0.5 to about 0.9 inches, about 0.6 to about 0.9 inches, about 0.7 to about 0.9 inches, about 0.8 to about 0.9 inches, about 0.001 to about 0.8 inches, about 0.01 to about 0.8 inches, about 0.1 to about 0.8 inches, about 0.2 to about 0.8 inches, about 0.3 to about 0.8 inches, about 0.4 to about 0.8 inches, about 0.5 to about 0.8 inches, about 0.6 to about 0.8 inches, about 0.7 to about 0.8 inches, about 0.001 to about 0.7 inches, about 0.01 to about 0.7 inches, about 0.1 to about 0.7 inches, about 0.2 to about 0.7 inches, about 0.3 to about 0.7 inches, about 0.4 to about 0.7 inches, about 0.5 to about 0.7 inches, about 0.6 to about 0.7 inches, about 0.001 to about 0.6 inches, about 0.01 to about 0.6 inches, about 0.1 to about 0.6 inches, about 0.2 to about 0.6 inches, about 0.3 to about 0.6 inches, about 0.4 to about 0.6 inches, about 0.5 to about 0.6 inches, about 0.001 to about 0.5 inches, about 0.01 to about 0.5 inches, about 0.05 to about 0.5 inches, about 0.1 to about 0.5 inches, about 0.15 to about 0.5 inches, about 0.2 to about 0.5 inches, about 0.3 to about 0.5 inches, or about 0.4 to about 0.5 inches.

The frozen *M. elsdenii* cells can be stored frozen (e.g., below 0° C.) before freeze-drying or can be immediately freeze-dried. In some embodiments, the frozen *M. elsdenii* cells are stored at a temperature below about 0° C., below about −10° C., below about −20° C., below about −50° C., below about −80° C., or below about −196° C. In some embodiments, the frozen *M. elsdenii* cells are stored at a temperature of about −20° C., about −30° C., about −40° C., about −50° C., about −60° C., about −70° C., about −80° C., about −90° C., about −100° C., about −150° C., about −196° C., or about −210° C.

In some embodiments, the frozen *M. elsdenii* cells are lyophilized. In some embodiments, the frozen *M. elsdenii* cells are freeze-dried. Freeze-drying involves, for example, the removal of liquid from frozen cells.

In some embodiments, freeze-drying the *M. elsdenii* cells comprises placing the frozen cells into a freeze-drier. In some embodiments, the freeze-drying comprises subjecting the frozen cells to reduced pressure, and gradually warming the cells to room temperature.

In some embodiments, the method comprises freeze-drying the cells under anaerobic conditions.

In some embodiments, the freeze-dried *M. elsdenii* is produced on a commercial scale.

In some embodiments, the lyophilization of *M. elsdenii* cells occurs at a pressure between about 50 mTorr to about 2,000 mTorr, between about 100 mTorr to about 1,950 mTorr, between about 150 mTorr to about 1,900 mTorr, between about 200 mTorr to about 1,850 mTorr, between about 250 mTorr to about 1,800 mTorr, between about 300 mTorr to about 1,750 mTorr, between about 350 mTorr to about 1,700 mTorr, between about 400 mTorr to about 1,650 mTorr, between about 450 mTorr to about 1,600 mTorr, between about 500 mTorr to about 1,550 mTorr, between about 550 mTorr to about 1,500 mTorr, between about 600 mTorr to about 1,500 mTorr, between about 650 mTorr to about 1,450 mTorr, between about 700 mTorr to about 1,400 mTorr, between about 750 mTorr to about 1,350 mTorr, between about 800 mTorr to about 1,300 mTorr, between about 850 mTorr to about 1,250 mTorr, between about 900 mTorr to about 1,200 mTorr, between about 950 mTorr to about 1,150 mTorr, or between about 1,000 mTorr to about 1,100 mTorr. In some embodiments, the pressure during the lyophilization process is 135 mTorr. In some embodiments, the pressure during the lyophilization process is 250 mTorr.

In some embodiments, the time to complete the lyophilization process is between about 5 hours and 15 days, between about 6 hours and 15 days, between about 7 hours and 15 days, between about 8 hours and 15 days, between about 9 hours and 15 days, between about 10 hours and 15 days, between about 11 hours and 15 days, between about 12 hours and 15 days, between about 18 hours and 15 days, between about 24 hours and 15 days, between about 36 hours and 14 days, between about 48 hours and 13 days, between about 3 days and 12 days, between about 4 days and 11 days, between about 5 days and 10 days, between about 6 days and 9 days, between about 7 days and 8 days. In some embodiments, the time to complete the lyophilization process is about 18.5 hours. In some embodiments, the time to complete the lyophilization process is about 38.5 hours.

In some embodiments, about $1 \times 10^3$ to $1 \times 10^{12}$ CFU/g of freeze-dried *M. elsdenii* cells are produced by a method disclosed herein. In some embodiments, about $1 \times 10^3$ to $1 \times 10^{12}$ CFU/g of *M. elsdenii* cells are viable after freeze-drying.

Freeze-dried *Megasphaera elsdenii* cells also can be produced by a method comprising: (a) preparing a culture under anaerobic conditions comprising *M. elsdenii* cells and a growth media comprising at least two carbon sources selected from the group consisting of: casein, lactate (i.e., lactic acid), dextrose, fructose, fructan, glucose, sucrose, lactose, maltose, acetate, glycerol, mannitol, saccharose, xylose, molasses, fucose, glucosamine, dextran, a fat, an oil, glycerol, sodium acetate, arabinose, soy protein, soluble protein, raffinose, and combinations thereof, (b) harvesting the cells under anaerobic conditions, (c) freezing the cells, and (d) freeze-drying the cells, wherein about $1 \times 10^3$ to about $1 \times 10^{12}$ CFU/g of freeze-dried *M. elsdenii* cells are produced.

Freeze-dried *Megasphaera elsdenii* cells also can be produced by a method comprising: (a) preparing a culture comprising *M. elsdenii* cells and a growth media, (b) harvesting the cells under anaerobic conditions within 12 hours after the culture has ended its exponential growth phase, (c) freezing the cells, (d) freeze-drying the cells, and optionally (e) encapsulating the freeze-dried cells, wherein freeze-dried *M. elsdenii* cells or encapsulated freeze-dried *M. elsdenii* cells are produced.

Freeze-dried *Megasphaera elsdenii* cells also can be produced by a method comprising: (a) preparing a culture comprising *M. elsdenii* cells and a growth media, (b) harvesting the cells, (c) freezing the cells at a temperature of about −80° C. to about −210° C. within 5 hours of harvesting, (d) freeze-drying the cells, and optionally (e) encapsulating the freeze-dried cells, wherein freeze-dried *M. elsdenii* cells are produced or encapsulated freeze-dried *M. elsdenii* cells are produced.

In some embodiments, the present invention is directed to an encapsulated freeze-dried composition comprising *M. elsdenii* cells, wherein the freeze-dried powder is encapsulated with (a) an oil, including but not limited to, vegetable oil, palm oil, palmitic acid, stearic acid, oleic acid, linoleic acid, and linolenic acid (b) food-grade polymer, including by not limited to, alginate, chitosan, carboxymethyl cellulose, xanthan gum, starch, carrageenan, galatin, and pectin (c), milk proteins, including but not limited to, casein and whey protein, and (d) plant protein from soy, pulses, and cereals, including but not limited to, Zein. In some embodiments, the amount of freeze-dried *M. elsdenii* cells or encapsulated freeze-dried *M. elsdenii* cells produced by a method disclosed herein and/or the amount of *M. elsdenii* cells or the encapsulated freeze-dried *M. elsdenii* cells that are viable after freeze-drying is about $1 \times 10^3$ CFU/g to about $1 \times 10^{12}$ CFU/g about $1 \times 10^3$ CFU/g to about $1 \times 10^{11}$ CFU/g, about $1 \times 10^3$ CFU/g to about $1 \times 10^{10}$ CFU/g, about $1 \times 10^3$ CFU/g to about $1 \times 10^9$ CFU/g, about $1 \times 10^3$ CFU/g to about $1 \times 10^8$ CFU/g, about $1 \times 10^3$ CFU/g to about $1 \times 10^7$ CFU/g, about $1 \times 10^3$ CFU/g to about $1 \times 10^6$ CFU/g, about $1 \times 10^3$ CFU/g to about $1 \times 10^5$ CFU/g, about $1 \times 10^4$ CFU/g to about $1 \times 10^{12}$ CFU/g, about $1 \times 10^5$ CFU/g to about $1 \times 10^{12}$ CFU/g, about $1 \times 10^6$ CFU/g to about $1 \times 10^{12}$ CFU/g, about $1 \times 10^7$ CFU/g to about $1 \times 10^{12}$ CFU/g, about $1 \times 10^8$ CFU/g to about $1 \times 10^{12}$ CFU/g, about $1 \times 10^9$ CFU/g to about $1 \times 10^{12}$ CFU/g, about $1 \times 10^{10}$ CFU/g to about $1 \times 10^{12}$ CFU/g, about $1 \times 10^3$ CFU/g to about $1 \times 10^5$ CFU/g, about $1 \times 10^4$ CFU/g to about $1 \times 10^6$ CFU/g, about $1 \times 10^5$ CFU/g to about $1 \times 10^7$ CFU/g, about $1 \times 10^6$ CFU/g to about $1 \times 10^8$ CFU/g, about $1 \times 10^7$ CFU/g to about $1 \times 10^9$ CFU/g, about $1 \times 10^8$ CFU/g to about $1 \times 10^{10}$ CFU/g, about $1 \times 10^9$ CFU/g to about $1 \times 10^{11}$ CFU/g, or about $1 \times 10^{10}$ CFU/g to about $1 \times 10^{12}$ CFU/g.

In some embodiments, the freeze-dried *M. elsdenii* cells or the encapsulated freeze-dried *M. elsdenii* cells are viable for about 14 days to about 24 months at about −80° C., about −20° C., about 4° C., about 25° C., or combinations thereof. In some embodiments, the freeze-dried *M. elsdenii* cells or the encapsulated freeze-dried *M. elsdenii* cells are viable for at least about 14 days, at least about 1 month, at least about 6 months, at least about 8 months, at least about 10 months, at least about 12 months, at least about 15 months, at least about 18 months, or at least about 24 months at about −80° C., about −20° C., about 4° C., about 25° C., or combinations thereof.

In some embodiments, about $1 \times 10^3$ CFU/g to about $1 \times 10^{12}$ CFU/g about $1 \times 10^3$ CFU/g to about $1 \times 10^{11}$ CFU/g, about $1 \times 10^3$ CFU/mL to about $1 \times 10^{10}$ CFU/g, about $1 \times 10^3$ CFU/g to about $1 \times 10^9$ CFU/g, about $1 \times 10^3$ CFU/g to about $1 \times 10^8$ CFU/g, about $1 \times 10^3$ CFU/g to about $1 \times 10^7$ CFU/g, about $1 \times 10^3$ CFU/g to about $1 \times 10^6$ CFU/g, about $1 \times 10^3$ CFU/g to about $1 \times 10^5$ CFU/g, about $1 \times 10^4$ CFU/g to about $1 \times 10^{12}$ CFU/g, about $1 \times 10^5$ CFU/g to about $1 \times 10^{12}$ CFU/g, about $1 \times 10^6$ CFU/g to about $1 \times 10^{12}$ CFU/g, about $1 \times 10^7$ CFU/g to about $1 \times 10^{12}$ CFU/g, about $1 \times 10^8$ CFU/g to about $1 \times 10^{12}$ CFU/g, about $1 \times 10^9$ CFU/g to about $1 \times 10^{12}$ CFU/g, about $1 \times 10^{10}$ CFU/g to about $1 \times 10^{12}$ CFU/g, about $1 \times 10^3$ CFU/g to about $1 \times 10^5$ CFU/g, about $1 \times 10^4$ CFU/g to about $1 \times 10^6$ CFU/g, about $1 \times 10^5$ CFU/g to about $1 \times 10^7$ CFU/g, about $1 \times 10^6$ CFU/g to about $1 \times 10^8$ CFU/g, about $1 \times 10^7$ CFU/g to about $1 \times 10^9$ CFU/g, about $1 \times 10^8$ CFU/g to about $1 \times 10^{10}$ CFU/g, about $1 \times 10^9$ CFU/g to about $1 \times 10^{11}$ CFU/g, or about $1 \times 10^{10}$ CFU/g to about $1 \times 10^{12}$ CFU/g of freeze-dried *M. elsdenii* cells or the encapsulated freeze-dried *M. elsdenii* cells are viable after storage at a temperature of about −80° C., about −20° C., about 4° C., or combinations thereof for at least about 14 days, at least about 1 month, at least about 6 months, at least about 8 months, at least about 10 months, at least about 12 months, at least about 15 months, at least about 18 months, or at least about 24 months.

In some embodiments, about $1 \times 10^3$ CFU/g to about $1 \times 10^{12}$ CFU/g about $1 \times 10^3$ CFU/g to about $1 \times 10^{11}$ CFU/g, about $1 \times 10^3$ CFU/g to about $1 \times 10^{10}$ CFU/g, about $1 \times 10^3$ CFU/g to about $1 \times 10^9$ CFU/g, about $1 \times 10^3$ CFU/g to about $1 \times 10^8$ CFU/g, about $1 \times 10^3$ CFU/g to about $1 \times 10^7$ CFU/g, about $1 \times 10^3$ CFU/g to about $1 \times 10^6$ CFU/g, about $1 \times 10^3$ CFU/g to about $1 \times 10^5$ CFU/g, about $1 \times 10^4$ CFU/g to about $1 \times 10^{12}$ CFU/g, about $1 \times 10^5$ CFU/g to about $1 \times 10^{12}$ CFU/g, about $1 \times 10^6$ CFU/g to about $1 \times 10^{12}$ CFU/g, about $1 \times 10^7$ CFU/g to about $1 \times 10^{12}$ CFU/g, about $1 \times 10^8$ CFU/g to about $1 \times 10^{12}$ CFU/g, about $1 \times 10^9$ CFU/g to about $1 \times 10^{12}$ CFU/g, about $1 \times 10^{10}$ CFU/g to about $1 \times 10^{12}$ CFU/g, about $1 \times 10^3$ CFU/g to about $1 \times 10^5$ CFU/g, about $1 \times 10^4$ CFU/g to about $1 \times 10^6$ CFU/g, about $1 \times 10^5$ CFU/g to about $1 \times 10^7$ CFU/g, about $1 \times 10^6$ CFU/g to about $1 \times 10^8$ CFU/g, about $1 \times 10^7$ CFU/g to about $1 \times 10^9$ CFU/g, about $1 \times 10^8$ CFU/g to about $1 \times 10^{10}$ CFU/g, about $1 \times 10^9$ CFU/g to about $1 \times 10^{11}$ CFU/g, or about $1 \times 10^{10}$ CFU/g to about $1 \times 10^{12}$ CFU/g of freeze-dried *M. elsdenii* cells or the encapsulated freeze-dried *M. elsdenii* cells are viable after storage at a temperature of about 25° C. for at least about 14 days, at least about 1 month, at least about 6 months, at least about 8 months, at least about 10 months, at least about 12 months, at least about 15 months, at least about 18 months, or at least about 24 months.

EXAMPLES

Reference is now made to the following examples, which together with the above descriptions illustrate some embodiments of the invention in a non-limiting fashion.

Example 1

Evaluation of *Megasphaera elsdenii* NCIMB 41125 in Production of Ensiled Plant Material A. Treatment of Plant Material and Ensiling Plant material from fresh corn was treated with either $2 \times 10^8$ CFU/mL *Megasphaera elsdenii* cells (i.e., *Megasphaera elsdenii* strain NCIMB 41125, MSBiotec®, Wamego, Kansas) applied at a rate of 50 mL per ton of plant material via spray gun or was untreated (control).

Approximately 100 pounds (lb) of plant material treated with *Megasphaera elsdenii* cells or untreated plant material were packed into separate 15 gallon barrels (i.e., silos) and sealed. Four replicates were prepared for each treatment. Ensiling occurred for 120 days under standard conditions.

Figure 1:
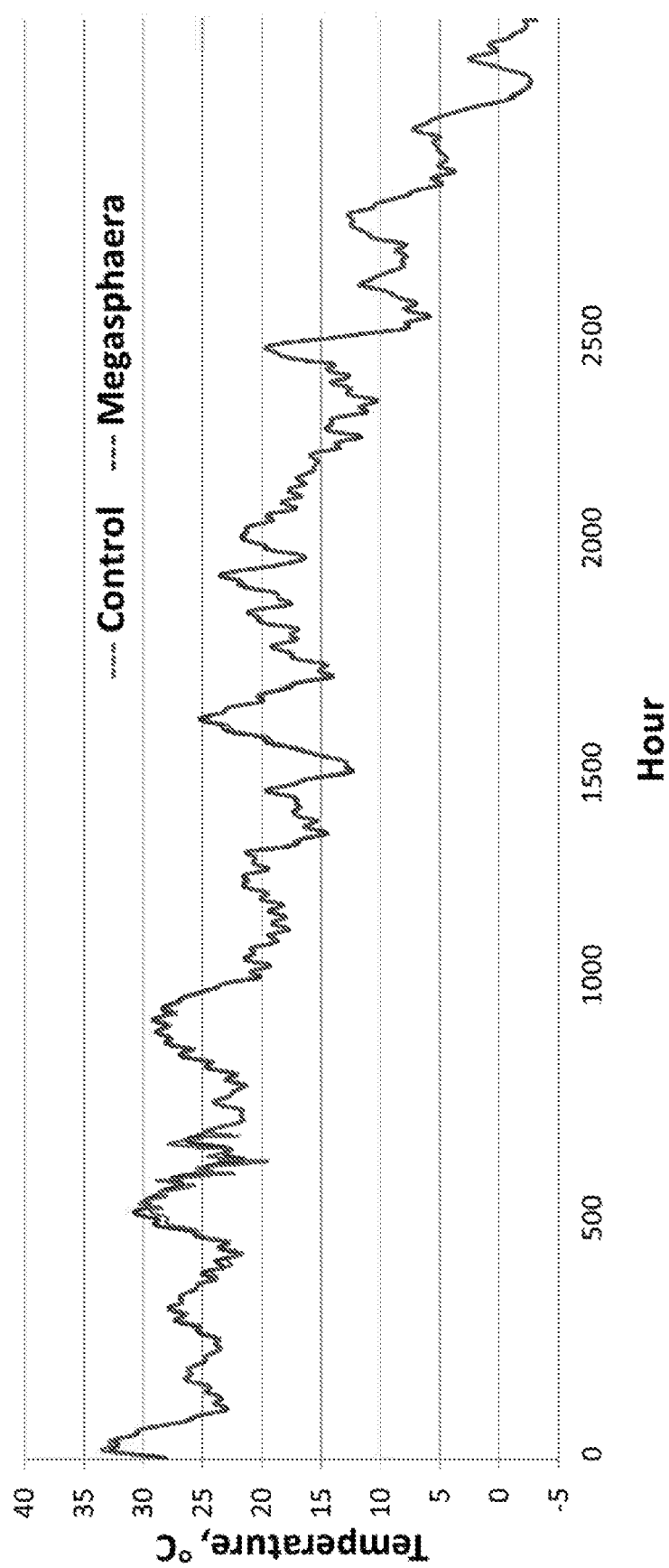

Each silo contained a temperature probe connected to a data logger. Temperature readings (° C.) were collected hourly over the 120 days of ensiling, with the data shown in FIG. 1 for the treatment with *Megasphaera elsdenii* cells ("Megasphaera") or control ("Control").

Figure 2:
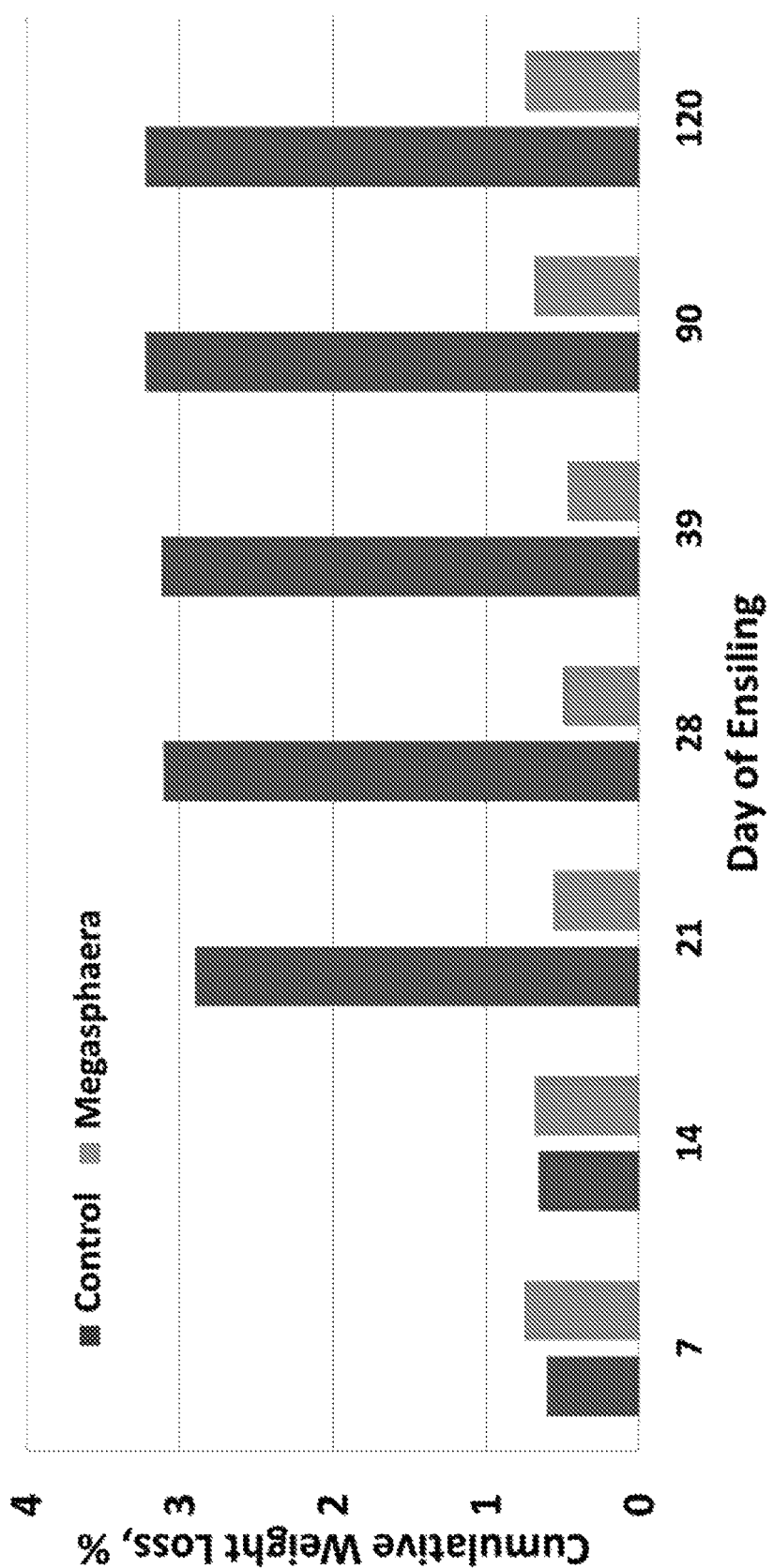

Silos were weighed on days 7, 14, 21, 28, 39, 90, and 120 to determine the percentage of cumulative weight loss (e.g., respiration losses) over the ensiling period as compared to the starting weight on day 0. See FIG. 2; Effect of Treatment, P<0.01; Effect of Day, P>0.10; Treatment by Day Interaction, P>0.10; Standard Error of the Mean=3.16.

Additional tests were conducted on three opening days (i.e., days on which the silos were opened), including day 0, day 14, and day 120 of ensiling.

B. pH and VFA Tests

Figure 3:
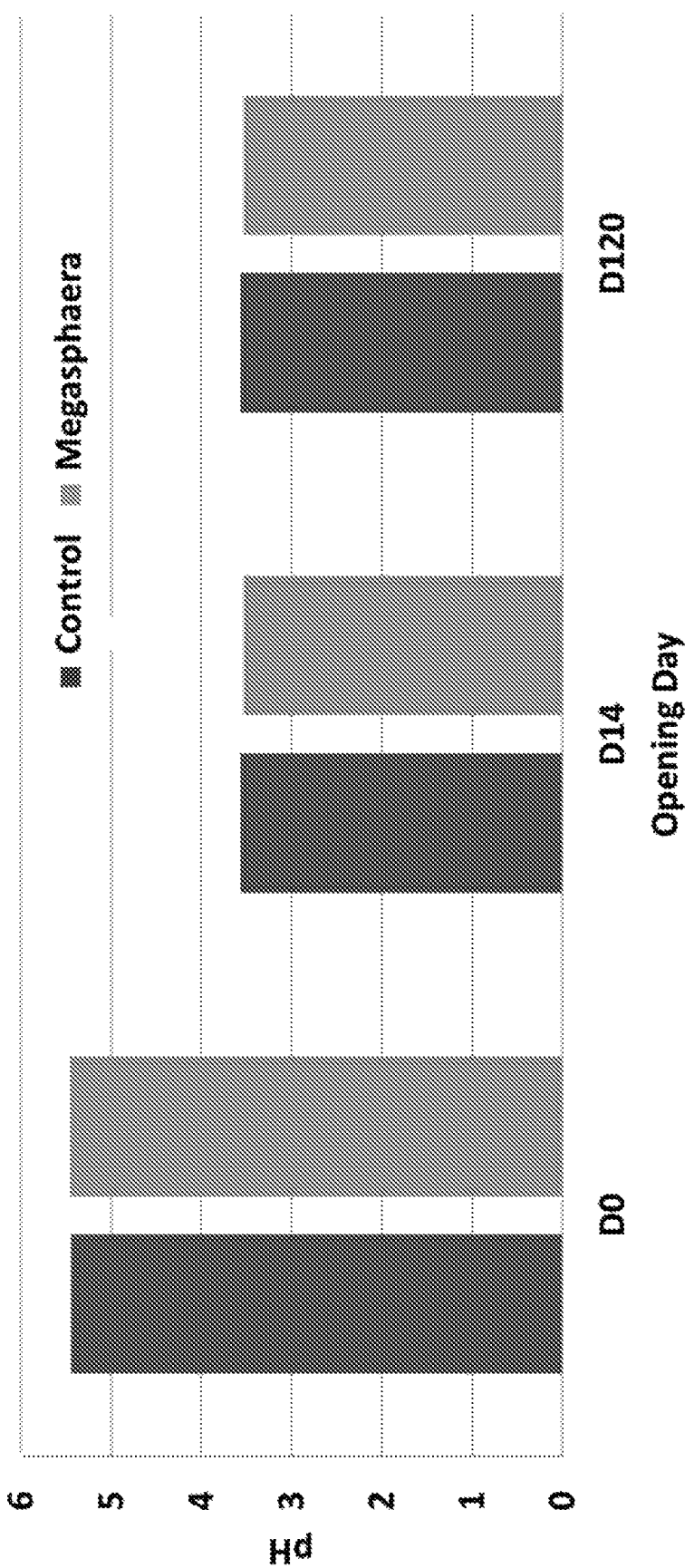

Samples were collected from each treatment silo on opening days 0, 14, and 120. The pH and volatile fatty acid (VFA) millimolar concentrations in the samples were measured. Mean values for pH are shown in FIG. 3; No Effect of Treatment, P>0.6; Standard Error of the Mean=0.02. Mean values for VFA concentrations are shown in FIG. 4; "SEM" is the Standard Error of the Mean. "D"=Opening Day Effect, with P<0.05.

C. Aerobic Stability Tests

On each opening days 14 and 120, approximately 10 lb of ensiled plant material were transferred from each treatment silo to respective 18 L containers. The sample in each 18 L container was exposed to ambient air for 14 days.

Figure 5:
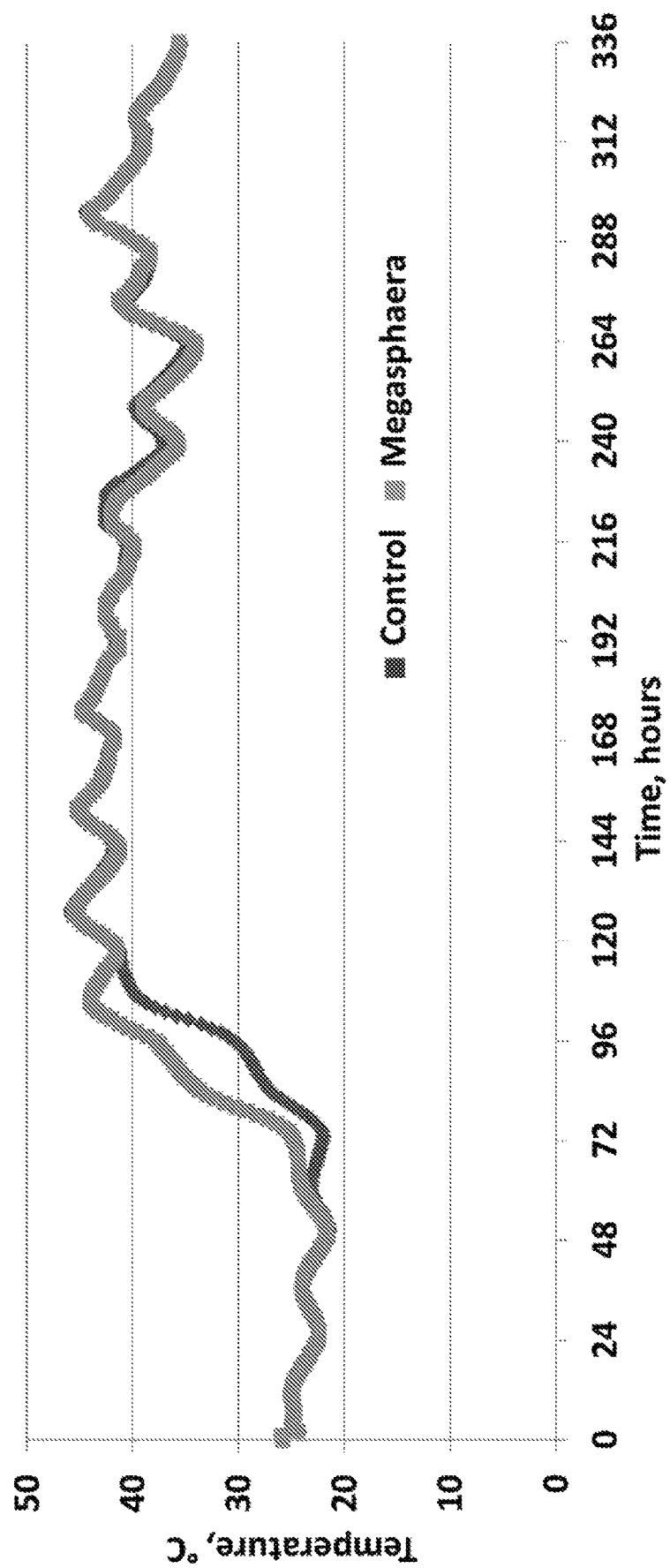
Figure 10:
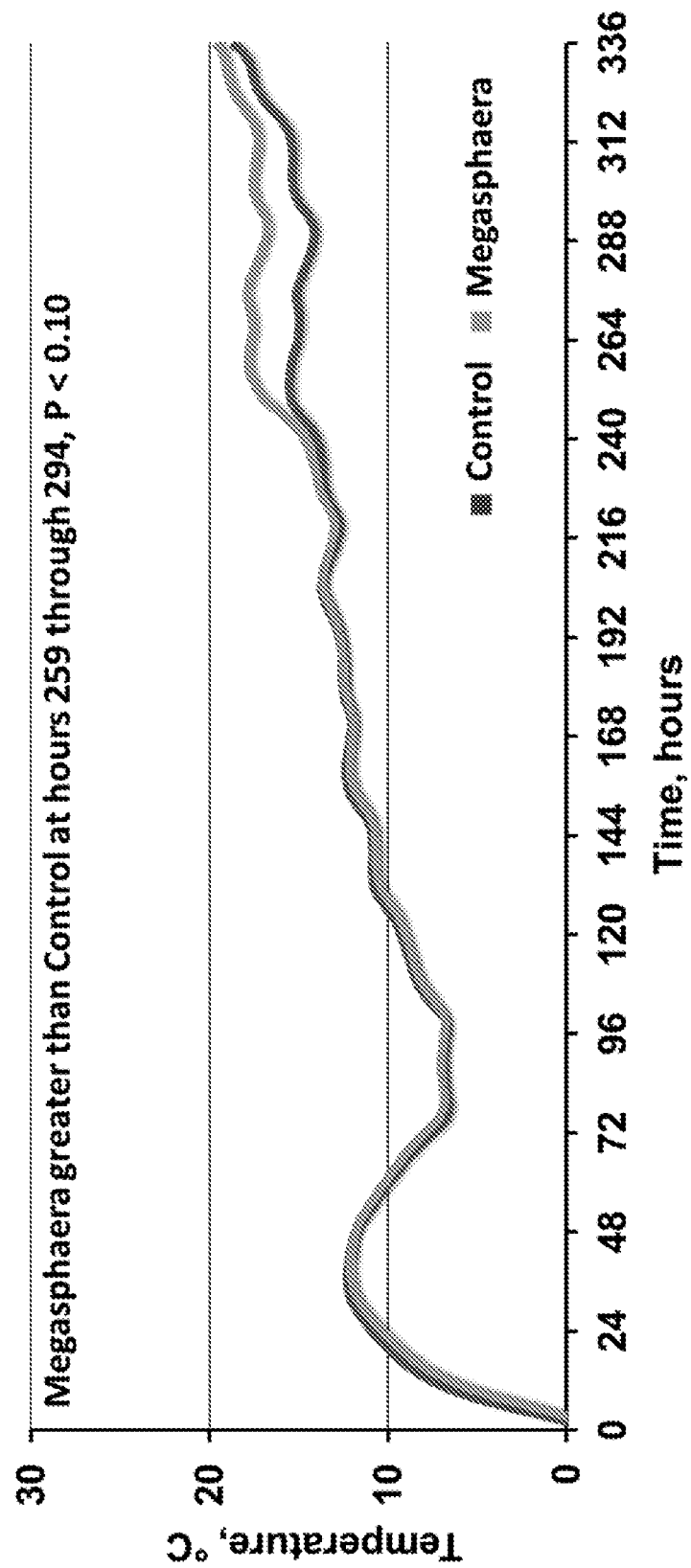

FIG. 5 and FIG. 10 show the mean temperature (° C.) measured over the 14 day exposure to ambient air for each treatment on opening day 14 (FIG. 5; Treatment by Time Interaction, P<0.01; Effect of Time, P<0.01; Effect of Treatment, P<0.01; Standard Error of the Mean=0.023) and opening day 120 (FIG. 10; Treatment by Time Interaction, P>0.10; Effect of Time, P<0.01; Effect of Treatment, P<0.01; Standard Error of the Mean=1.23).

Figure 6:
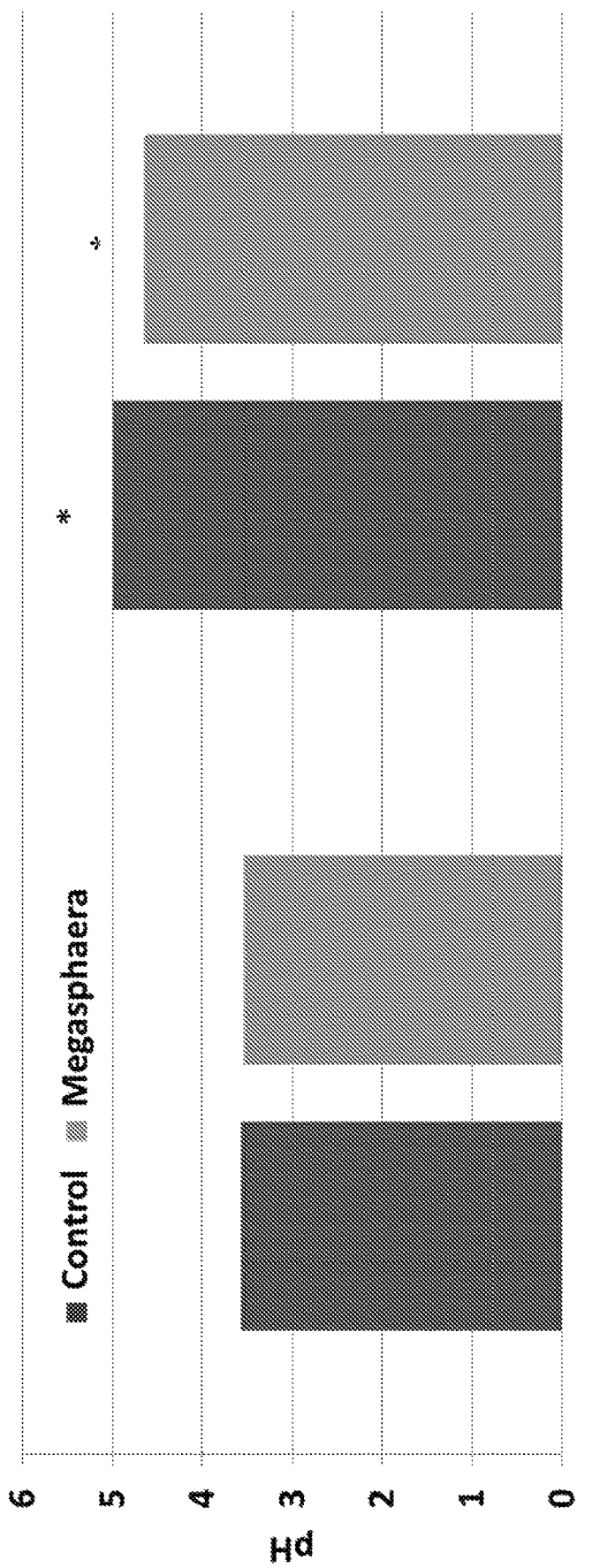
Figure 11:
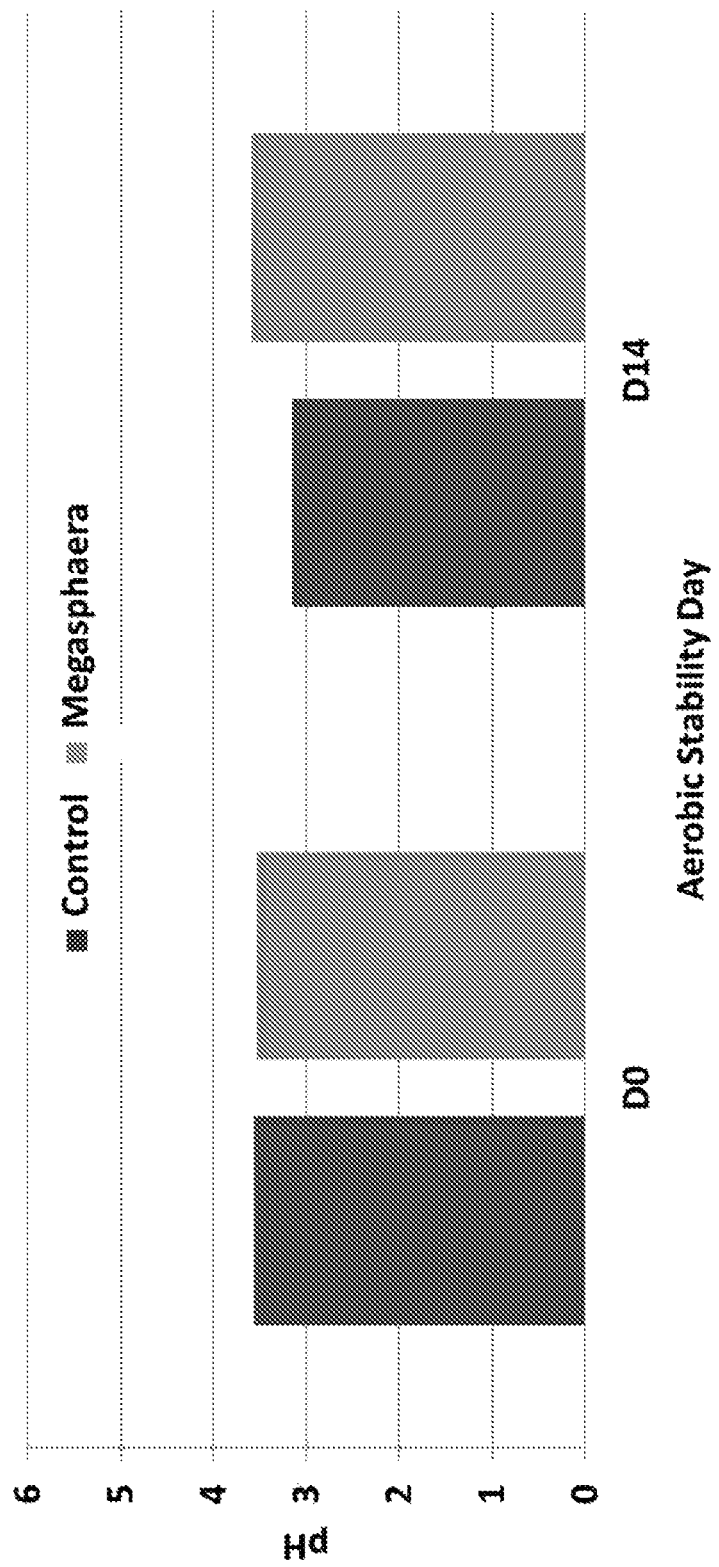

FIG. 6 and FIG. 11 show the mean pH measurements at day 0 ("D0") and day 14 ("D14") of exposure to ambient air for each treatment on opening day 14 (FIG. 6; Treatment by Day Interaction, P<0.05; Effect of Time, P<0.01; Effect of Treatment, P<0.05; Treatments denoted with an asterisk ("*") are different from one another on day 14, P<0.05; Standard Error of the Mean=0.07) and opening day 120 (FIG. 11; Treatment by Day Interaction, P>0.1; Effect of Time, P>0.1; Effect of Treatment, P>0.1; Standard Error of the Mean=0.23).

Figure 7:
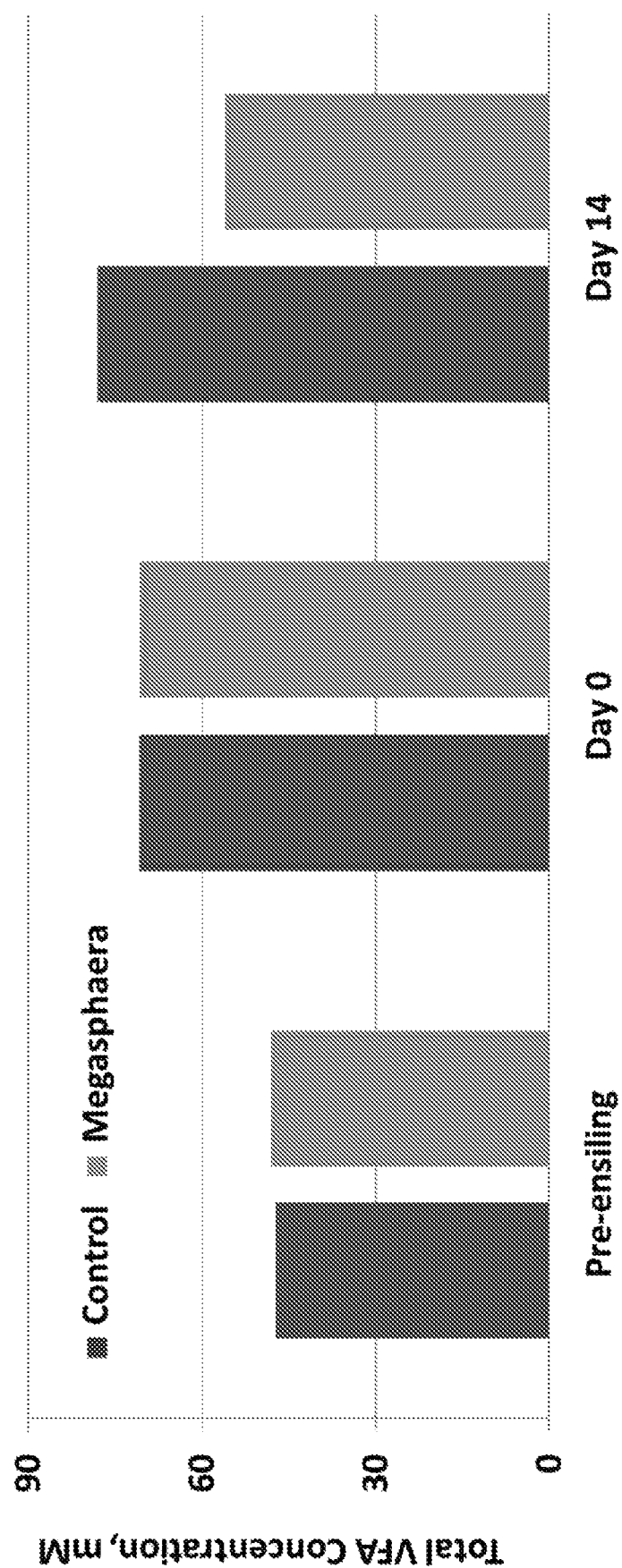
Figure 12:
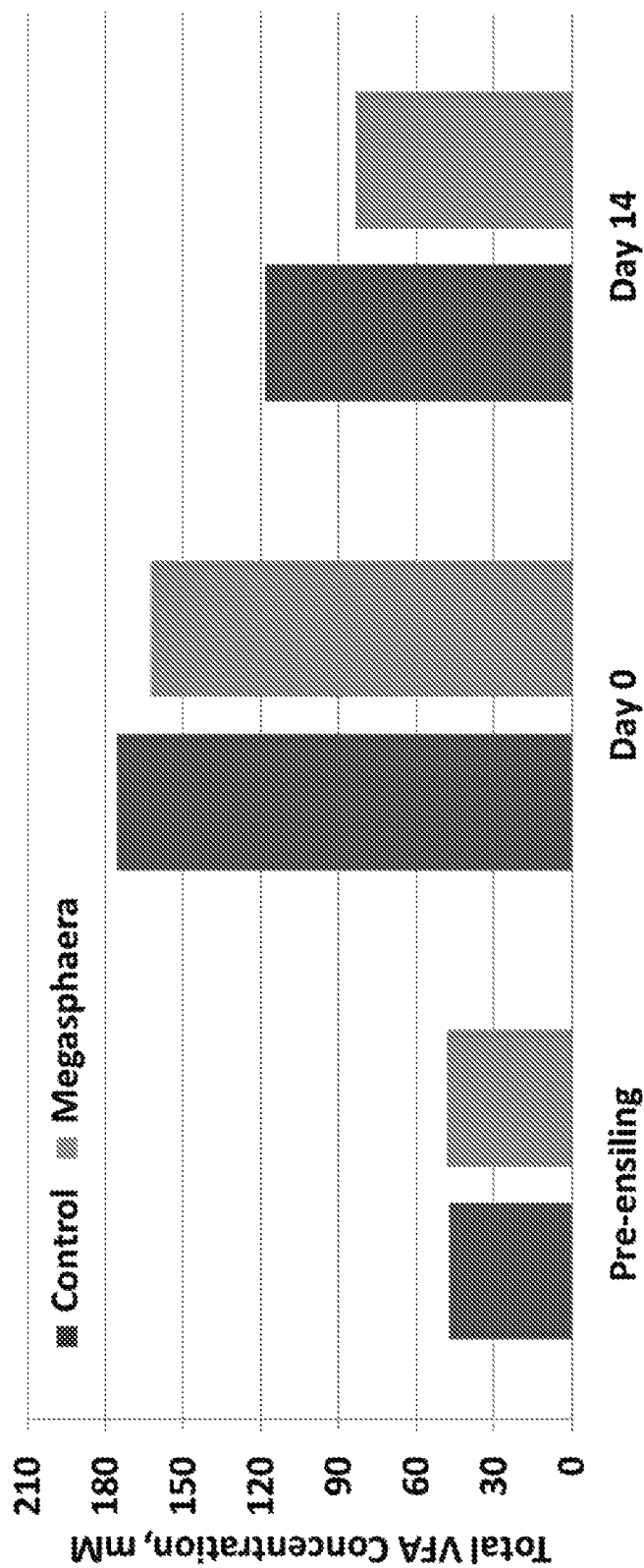

FIGS. 7-8 and FIGS. 12-13 show mean VFA concentrations (millimolar (mM)) measured at day 0 and day 14 of exposure to ambient air for each sample collected on opening day 14 (FIGS. 7-8) and opening day 120 (FIGS. 12-13). FIG. 7 and FIG. 12 show total VFA concentrations, including for a pre-ensiling sample. For FIG. 7, Treatment by Opening Day Interaction, P>0.5; Effect of Inoculant, P>0.1; Effect of Opening Day, P<0.6; Standard Error of the Mean=6.65. For FIG. 8, "D"=Opening Day Effect, with P<0.05. For FIG. 12, Treatment by Oxygen Exposure Interaction, P>0.5; Effect of Inoculant, P>0.15; Effect of Day of Oxygen Exposure, P<0.01; Standard Error of the Mean=18.4. For FIG. 13, "D"=Day of Oxygen Exposure Effect; "I"=Interaction Effect; "T"=Treatment Effect; Letters indicate P<0.05.

Figure 9:
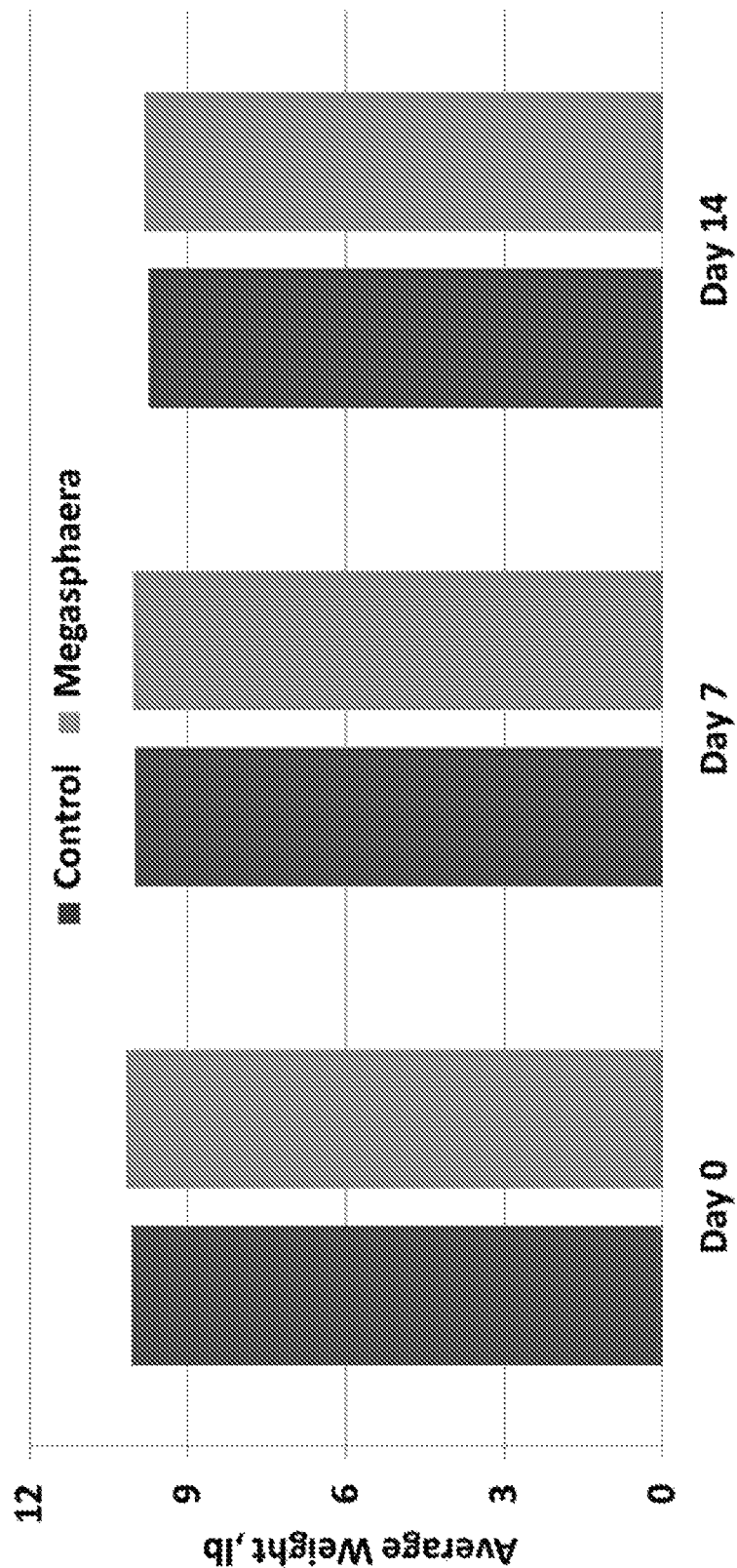
Figure 14:
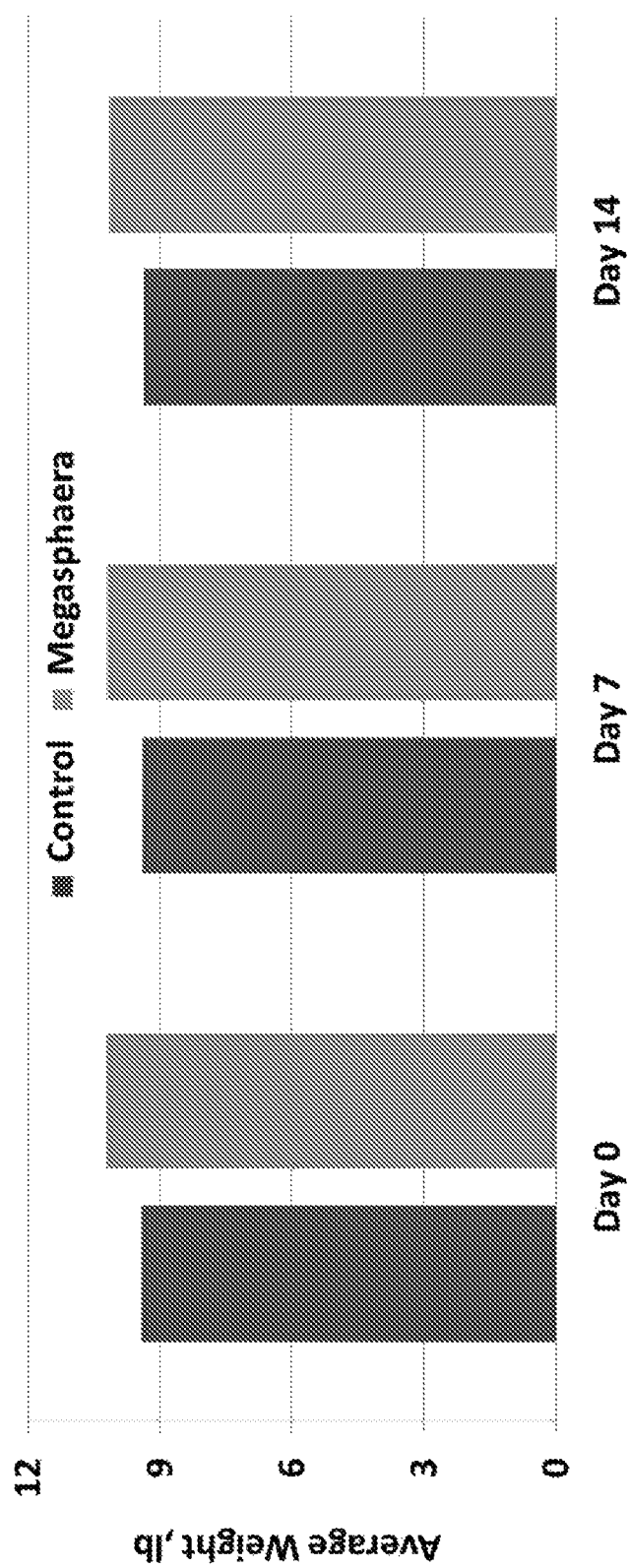

FIG. 9 and FIG. 14 show average weight (lb) at day 0, day 7, and day 14 of exposure to ambient air for each treatment on opening day 14 (FIG. 9, Treatment by Day Interaction, P>0.9; Effect of Day, P>0.1; Effect of Treatment, P>0.6; Standard Error of the Mean=0.16) and opening day 120 (FIG. 14, Treatment by Day Interaction, P>0.90; Effect of Day, P>0.6; Effect of Treatment, P<0.01; Standard Error of the Mean=0.10).

D. Summary

As compared to a control, treatment of plant material with *M. elsdenii* cells prior to ensiling resulted in, for example, less weight loss during ensiling (i.e., during anaerobic fermentation) as well as a decreased pH and less weight loss following exposure to ambient air (i.e., increased aerobic stability). See, e.g., FIGS. 2, 6, and 9, respectively.

Example 2

Effect of Temperature on Yield of Liquid Cultures of *M. elsdenii*

Figure 15:
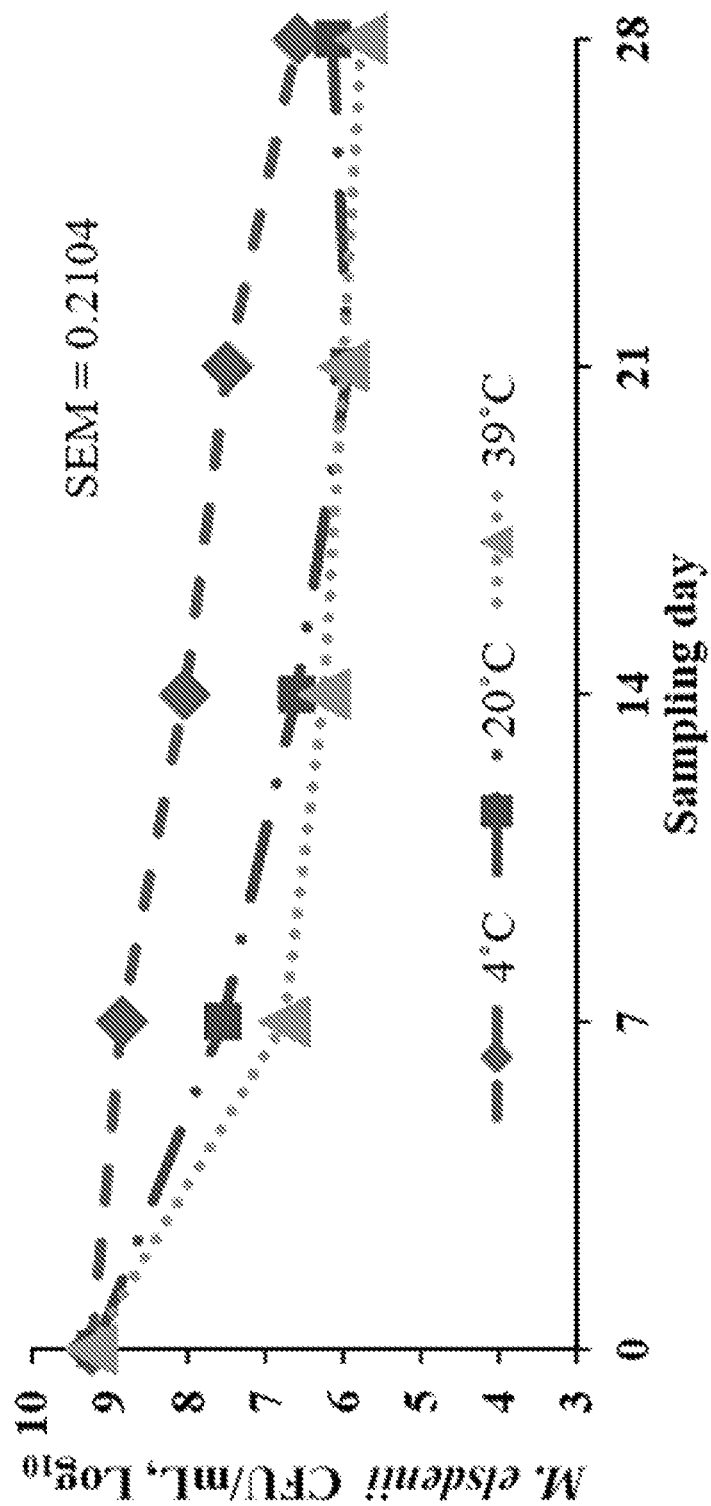
FIG. 15 shows the effect of storage temperature on viability of liquid cultures of *Megasphaera elsdenii* NCIMB 41125 over a 28-day period in terms of yield of *M. elsdenii* cells in colony forming units per milliliter ("CFU/mL") in logarithmic ("Log 10") scale.

Storage temperatures of 4° C., 20° C., and 39° C., were tested to assess viability of cells in liquid cultures of *M. elsdenii* NCIMB 41125 after 0, 7, 14, 21, and 28 days. Results revealed that storing the product at 4° C. significantly (P<0.001) improved viability of the culture compared to storage at 20° C. or 39° C., regardless of sampling day. After 28 days, product stored at 4° C. had $3.98 \times 10^6$ colony forming units per milliliter (CFU/mL) compared to $1.26 \times 10^6$ and $6.3 \times 10^5$ CFU/mL for product stored at 20° C. or 39° C., respectively (P<0.01; FIG. 15). Thus, the results show that a decreased storage temperature improves viability of liquid cultures of *M. elsdenii* NCIMB 41125.

Figure 16:
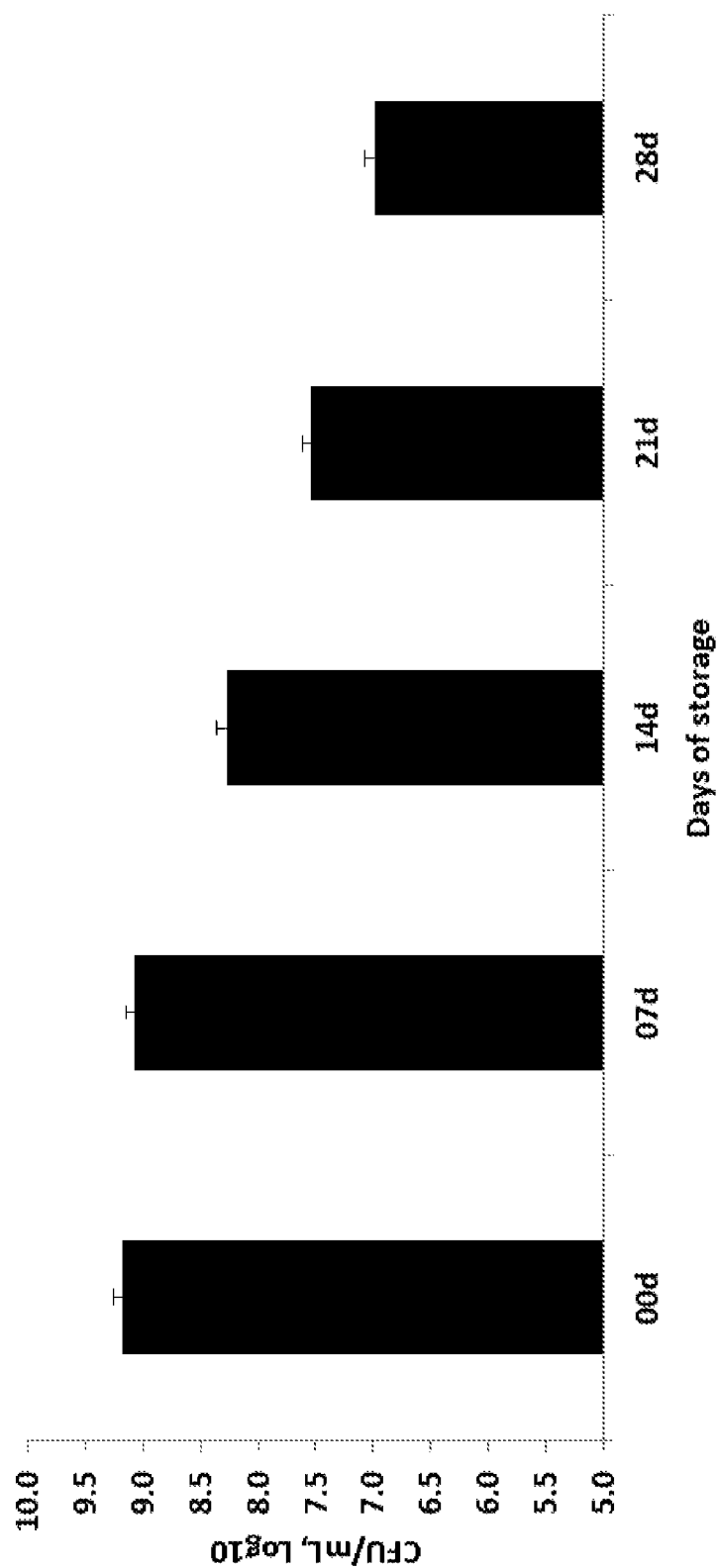
FIG. 16 shows the viability of liquid cultures of *M. elsdenii* NCIMB 41125 after 0, 7, 14, 21, and 28 days of storage at room temperature in terms of yield of *M. elsdenii* cells in CFU/mL in Log 10 scale.

Additional data from a separate study shows that *Megasphaera elsdenii* NCIMB 41125 yield in a liquid culture decreases after 0, 7, 14, 21, and 28 days of storage at room temperature (FIG. 16).

Example 3

Use of Tangential Flow Filtration for Concentrating Cultures of *M. elsdenii*

Tangential flow filtration (TFF) was investigated as a method for concentrating large volumes of culture at high throughput.

Figure 17:
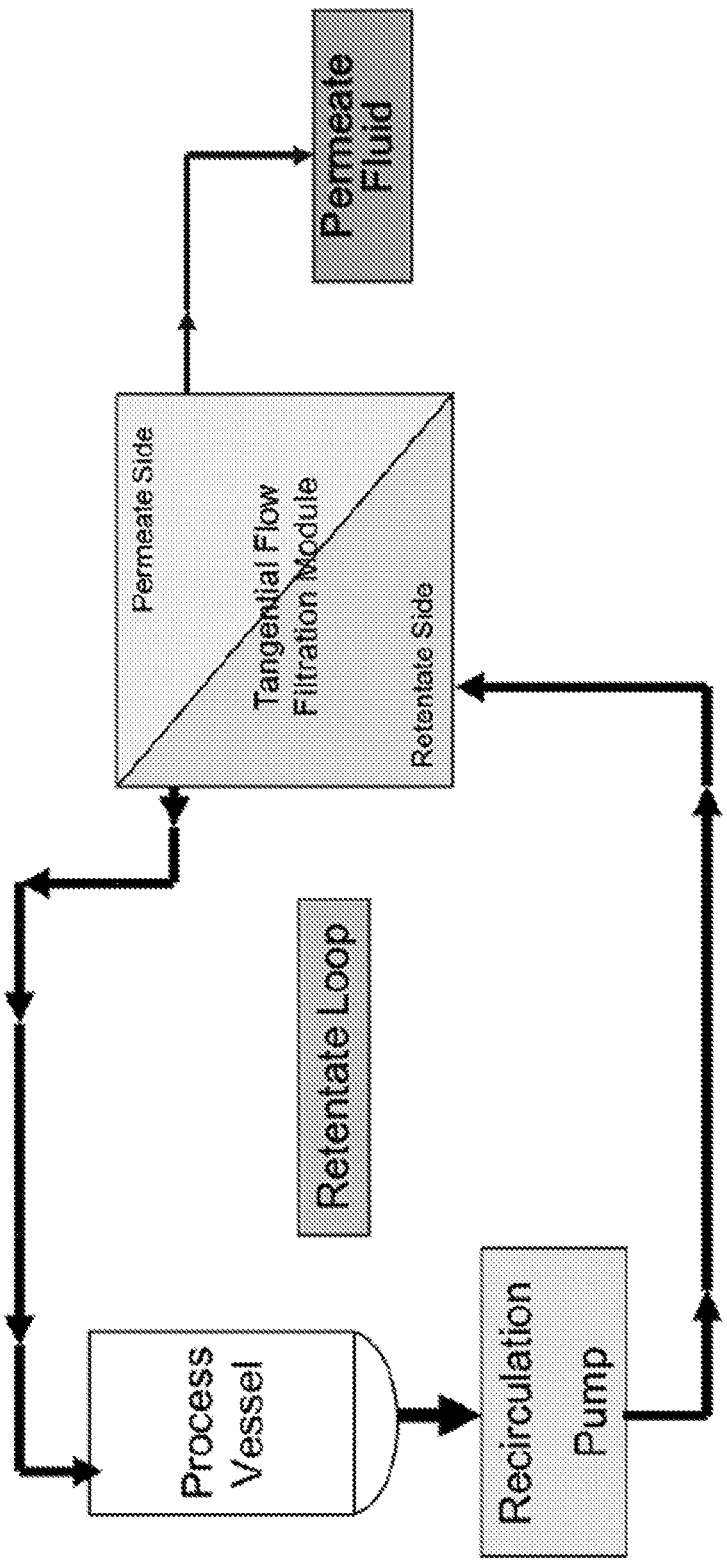
FIG. 17 shows a schematic of a tangential flow filtration ("TFF") system.

A pilot scale TFF system (see FIG. 17) was integrated into the production line for *M. elsdenii* and tested on 500-Liter (L) production runs to assess the pilot scale system at the volume reduction levels of 70%, 80%, and 90%. A TFF Module with one RC 100 kDa membrane (0.875 mm channel height) was used. Three production runs were performed for each reduction level for a total of nine runs. Samples were collected for each run and were analyzed for pH, optical density (OD), presence or absence of aerobic contaminants, osmolarity, volatile fatty acids profile, *M. elsdenii* concentration, and growth characteristics. The samples were collected from the nine *M. elsdenii* cultures ("Non-Freeze-Dried") before the start of filtration, from the permeate ("Permeate"), which is the volume removed by the system, and from the retentate ("Retentate"), which is the concentrated *M. elsdenii* culture volume comprising the cells that remains after the volume reductions.

Permeate samples collected at the beginning, middle, and end of the concentration process had consistent OD readings across volume reduction levels, all below 0.045 (data not shown). The amount of *M. elsdenii* recovered in the permeate increased over the course of the concentration process (P=0.0006), but was still negligible (less than $3 \times 10^4$ CFU/mL) in comparison to the amount of cells collected in the retentate (<0.002%). Volume reduction levels did not have an effect on *M. elsdenii* concentration recovered in permeate (P>0.9; Table 2).

TABLE 2

Average *M. elsdenii* yield in samples collected during the nine production runs performed to evaluate the pilot scale TFF system at 70%, 80%, and 90% volume reductions

| Samples | CFU/mL, Log10 | | | Standard Error | Trt effect, P-value |
|---|---|---|---|---|---|
| | 70% | 80% | 90% | | |
| Permeate | 1.19 | 1.07 | 1.12 | 0.40 | 0.958 |
| Retentate | 8.99 | 9.04 | 9.25 | 0.03 | <0.0001 |

*M. elsdenii* yield in the retentate was not different in bags collected at the beginning, middle, or end of each bagging process (P=0.6088; data not shown). Retentate yield was affected by volume reduction levels (P<0.0001; Table 2 and FIG. 18). The 90% volume reduction retentate had higher yield than the 70% and the 80% volume reduction retentate (P<0.0001). But, the 70% and the 80% retentate were not different from one another (P>0.09).

The filtration process did not affect the capacity of *M. elsdenii* cells to grow when inoculated back into SDL-20 media (Table 3). Slopes of the exponential phase were not affected by the volume reduction level (P>0.3), but were affected by the type of sample: "Retentate" versus "Non-Freeze-Dried" (P<0.001). Lag time was affected by both volume reduction level and sample type (P<0.001). Lag time for the retentate decreased with increasing volume reduction, which was representative of higher cell concentration.

TABLE 3

Comparison of slope and lag time between initial *M. elsdenii* (pre-filtration = Non-Freeze-Dried) and retentate (post-filtration) collected during the different volume reduction TFF runs

| | Sample type | | | | | | Effects, P-values | | |
|---|---|---|---|---|---|---|---|---|---|
| | Non-Freeze Dried | | | Retentate | | | Sample type | Vol. red. | Interaction |
| | 70% | 80% | 90% | 70% | 80% | 90% | | | |
| Slope | 0.39 | 0.36 | 0.37 | 0.44 | 0.42 | 0.43 | <0.001 | 0.329 | 0.979 |
| Lag time, h | 1.42$^a$ | 1.10$^b$ | 1.07$^b$ | 0.32$^c$ | 0.29$^c$ | 0.24$^c$ | 0.001 | <0.001 | <0.001 |

Example 4

Freezing and Freeze-Drying Parameters for *M. elsdenii*

A. Freezing and freeze-drying of retentates

Retentates obtained through TFF were used to test freezing protocols, cryoprotectant inclusion, and various freeze-drying parameters.

Retentates were transferred to sterile degassed serum bottles and aseptically mixed with the different cryoprotectant formulations (w/v): no cryoprotectant (Ctrl), skim milk (SM), trehalose (T), and betaine. Retentates mixed with the appropriate cryoprotectant were sampled to determine pre-freeze-drying *M. elsdenii* concentration (i.e., viability count). Mixtures were transferred into 10 mL vials (4 mL/vials) and snap frozen in liquid nitrogen or slowly frozen at –80° C. overnight. Vials were transferred to the freeze-dryer to be lyophilized using either a slow or a rapid cycle. Once freeze-drying was complete, survival of the bacteria was determined by resuspending the lyophilized product in the anaerobic chamber with anaerobic diluent, allowing it to rehydrate for 40 minutes at room temperature, and then plating onto SDL20 agar.

Cell loss was computed by subtracting the concentration of *M. elsdenii* recovered post freeze-drying from the initial concentration of *M. elsdenii* measured in the corresponding retentate mixed with cryoprotectants or not. SAS® software was used to compute cell-loss data by analyzing the interactions between volume reduction levels (70%, 80%, or 90%), freeze-drying cycle (Slow versus Rapid), freezing method (–80° C. versus Liquid Nitrogen), cryoprotectants (None, Betaine, Trehalose, Skim Milk, Maltodextrin, Trehalose/Skim Milk (T/SM), and Maltodextrin/Skim Milk (M/SM)).

Cell loss observed in the control treatment (no cryoprotectants) regardless of other criteria were 5 Log (CFU/mL) or higher. Likewise, cell loss observed in the betaine treatment regardless of other criteria was 3.96 Log CFU/mL or higher. Acceptable cell loss limit was set at 1.6 log CFU/mL. Retentates mixed with T/SM or M/SM were all below that threshold regardless of the freeze-drying cycle or the freezing method used with the exception of T/SM frozen at –80° C. and freeze-dried using the slow or rapid cycle (FIG. 19).

B. Effects of Freeze-Drying Conditions on Storage

*Megasphaera elsdenii* NCIMB 41125 was concentrated 10× using a filtration device, and freeze-drying assays were performed testing different characteristics: fast or slow initial freezing (liquid nitrogen versus –20° C.), with or without trehalose (0%, 4%, 7.5%, and 10%), and gentle or rapid freeze-drying cycles (38 h at $2\times10^{-6}$ Torr versus 16.5 h at $135\times10^{-6}$ Torr). All freeze-dried processes tested resulted in products able to retain sufficient viability to initiate growth of the culture after rehydration, even after prolonged storage of 4 to 12 months at room temperature. Differences in bacteria viability were, nevertheless, observed depending on the freeze-drying characteristics used (FIG. 20). Slow freezing, 7.5% trehalose incorporation, and gentle freeze-drying steps maintaining final water activity above 0.04 were associated with greater survival of *Megasphaera elsdenii*.

C. Effects of Cryoprotectants on Viability of Freeze-Dried *M. elsdenii*

Centrifuged *M. elsdenii* NCIMB 41125 cell concentrates were resuspended in infant milk formula prior to lyophilization, resulting in only a 1-log decrease in cell viability when cells were subsequently rehydrated. The addition of 4% trehalose and 7.5% skim milk to *M. elsdenii* concentrate was tested before slow freezing at –80° C. or snap freezing in liquid nitrogen to determine cell loss encountered during the initial freezing process. As shown in FIG. 21, snap freezing with 4% trehalose or 7.5% skim milk yielded the greatest recovery of viable cells (0.79 log reduction in viable cell count). Product without addition of cryoprotectants, regardless of the freezing technique used, lost between 2.34 and 1.95 log CFU/mL of *Megasphaera elsdenii*.

Example 5

Effects of Storage Conditions on Yield and Stability of Freeze-Dried *M. elsdenii*

To determine the effect of freeze-drying protocols and storage conditions on *Megasphaera elsdenii* NCIMB 41125 growth characteristics and shelf life, retentate obtained from 90% volume reduction was mixed with 8% trehalose/15% skim Milk (T/SM) or 8% maltodextrin/15% skim milk (M/SM), frozen at –80° C. or in liquid nitrogen (LiqN), and freeze-dried using the rapid cycle. Retentate samples were then tested for bacterial growth characteristics and cell survival during storage at 4° C. or 25° C. in aerobic or anaerobic conditions for 0, 2, 4, 8, 12, 16, 20, and 24 weeks using growth curve analysis and spread plating technique. Briefly, stored products were sampled, serially diluted, and plated onto a SDL agar plate. In addition, growth medium (SDL) was inoculated (1:100) with the rehydrated freeze-dried products and optical density (OD, 600 nm) recorded until the cultures reach stationary phase. The experiment was repeated on 3 different days and all treatments were performed in triplicate. The rehydrated freeze-dried samples were diluted in order to perform growth curves because without diluting, the absorbance was above the limit due to the presence of skim milk. In order to facilitate growth curves comparison, the same dilution was performed on the Non-freeze-dried samples used as control.

RESULTS: Samples were freeze-dried and stored at room temperature or 4° C. under aerobic or anaerobic conditions for 6 months. Samples stored in aerobic conditions regardless of the treatment rapidly decayed with an additional cell loss in comparison to their anaerobic counterpart ranging from 0.4 to 3.2 Log after only 2 weeks of storage. Based on those results and to improve figure clarity, only cell loss observed in freeze-dried products stored anaerobically are presented in FIG. 22. During storage in anaerobic conditions, samples stored at room temperature decayed faster than they counterpart stored at 4° C., with the exception of T/SM samples frozen in liquid nitrogen. T/SM samples frozen in liquid nitrogen and stored at room temperature post freeze-drying did not statistically lose more cells than their counterpart stored at 4° C. over the 16-week storage period (P>0.1). However, differences between samples became significant between the room temperature and 4° C. storage after 20 weeks of storage (P=0.0002), with a 0.84 log difference after 20 weeks and a 0.89 log difference after 24 weeks of storage. All M/SM samples decayed faster than their T/SM counterpart. After 24 weeks of storage (FIG. 23), cell loss in T/SM samples frozen in liquid nitrogen and stored at 4° C. under anaerobic conditions was significantly lower than any of the other treatments (P<0.02). T/SM samples frozen in liquid nitrogen and stored at 4° C. under anaerobic conditions had a 2.16 log loss compared to the *M. elsdenii* concentration observed prior to freeze-drying, with 0.82 log loss resulting from the 24-week storage period. On each sampling day, a growth curve experiment was performed to compare the growth characteristic of the freeze-dried products to the non-freeze-dried product. FIG. 24 shows the growth curves performed on samples frozen in liquid nitrogen, freeze-dried with the rapid cycle (18.5 hours at 250 mTorr), and stored anaerobically at 4° C. or room temperature. Non-freeze-dried samples used for each growth curve were "fresh" (no more than 2-days of age). Freeze-dried product stored at 4° C. had shorter lag time than the freeze-dried product stored at room temperature, which is consistent with the difference in *M. elsdenii* concentration observed in these samples (Table 4). After 16 weeks of storage T/SM samples regardless of the storage temperature had shorter lag time than the M/SM samples.

TABLE 4

Lag time observed on non-freeze-dried or rehydrated freeze-dried sample obtained from 90% volume reduction retentate, mixed with 8% trehalose/15% skim Milk (T/SM) or 8% maltodextrin/15% skim milk (M/SM), frozen in liquid nitrogen (LiqN), and freeze-dried using the rapid cycle after 12, 16, 20 or 24 weeks of storage under anaerobic conditions at 4 or 25° C.

|  | Lag time (hour) after X weeks of storage | | | | | |
| --- | --- | --- | --- | --- | --- | --- |
|  | 12 | 16 | 20 | 24 | Average | Std. dev. |
| Lactipro | 2.50 | 2.75 | 3.75 | 1.75 | 2.69 | 0.72 |
| M/SM stored at 25° C. | 8.50 | 9.00 | 10.00 | 11.75 | 9.81 | 1.24 |
| T/SM stored at 25° C. | 6.50 | 6.75 | 7.25 | 8.00 | 7.13 | 0.57 |
| M/SM stored at 4° C. | 5.75 | 8.25 | 8.00 | 8.75 | 7.69 | 1.15 |
| T/SM stored at 4° C. | 4.25 | 5.25 | 5.00 | 4.75 | 4.81 | 0.37 |

Slopes for non-freeze-dried and MSM treatment stored at 25° C. for 12 weeks and MSM treatment stored at 20° C. for 16 weeks were abnormally low (Table 5). After 20 and 24 weeks of storage, exponential phase slopes of freeze-dried samples were not numerically different from the non-freeze-dried control.

TABLE 5

Slopes of exponential phase observed on non-freeze-dried or rehydrated freeze-dried sample obtained from 90% volume reduction retentate, mixed with 8% trehalose/15% skim Milk (T/SM) or 8% maltodextrin/15% skim milk (M/SM), frozen in liquid nitrogen (LiqN), and freeze-dried using the rapid cycle after 12, 16, 20 or 24 weeks of storage under anaerobic conditions at 4 or 25° C.

|  | Exponential phase slopes after X weeks of storage | | | | | |
| --- | --- | --- | --- | --- | --- | --- |
|  | 12 | 16 | 20 | 24 | Average | Std. dev. |
| Lactipro | 0.22 | 0.31 | 0.34 | 0.31 | 0.30 | 0.04 |
| M/SM stored at 25° C. | 0.24 | 0.18 | 0.33 | 0.29 | 0.26 | 0.05 |
| T/SM stored at 25° C. | 0.31 | 0.30 | 0.34 | 0.32 | 0.32 | 0.02 |
| M/SM stored at 4° C. | 0.30 | 0.33 | 0.30 | 0.30 | 0.31 | 0.01 |
| T/SM stored at 4° C. | 0.32 | 0.31 | 0.33 | 0.32 | 0.32 | 0.01 |

Example 6

Treating Fresh-Cut Forage with *M. elsdenii* Alters Organic Acid Profile of Corn Silage A. Method of Ensiling Fresh-Cut Forage and Measuring Dry Matter, pH, VFA, Lactic Acid, and Acetic Acid in Samples Whole crop corn (plant material) containing approximately 39% dry matter was harvested and treated with *Megasphaera elsdenii* or left untreated (control). The plant material was placed into four silage bags (100-125 tons/bag). The plant material was treated with either $2 \times 10^9$ CFU/mL *Megasphaera elsdenii* cells (i.e., *Megasphaera elsdenii* strain NCIMB 41125, MSBiotec®, Wamego, Kansas) applied at a rate of 50 mL per ton of plant material via the forage harvester onboard aerosol applicator, or was untreated (control). The treatment with *M. elsdenii* resulted in approximately 100 billion colony forming units (CFU) of *M. elsdenii* per ton of fresh plant material. The silage is then packed into silage bags.

After 120 days of ensiling, a forage probe (30" length) was used to extract 12 silage samples from each. Samples were taken from 12 points uniformly distributed over the length of each bag, placed into foil pouches that were then vacuum sealed and stored in a −20° C. freezer. Two sub-samples were taken from each foil bag. The first was used to determine dry matter by weighing out approximately 200 g into a foil pan and placing it into a forced-air oven at 105° C. for 24 hours. The remaining portion was compressed using an arbor press to extract liquid, and pH of the liquid extract was measured. Four mL of liquid extract were combined with 1 mL of 25% (w/v) metaphosphoric acid solution in 10 mL conical tubes and frozen to facilitate deproteinization of samples.

Extracts were then thawed, homogenized, and centrifuged at 14,000×g for 15 minutes. Clear supernatant was transferred to chromatography vials and concentrations of volatile fatty acids (VFA) were determined using an Agilent 7890 gas chromatograph equipped with a flame ionization detector and capillary column (Nukol 15 m length×0.5 mm diameter×0.5 μm film thickness) using hydrogen as the carrier gas.

A colorimetric procedure was used to analyze lactic acid concentrations in the liquid extracts. Briefly, lactic acid standards were prepared at concentrations of 0, 2.5, 5, 10, and 15 mg/dL. Deionized water was combined with acidified liquid extract to achieve a dilution of 40:1. The resulting solutions (0.5 mL) were combined with 0.5 mL of 20% $CuSO_4.5H_2O$, 4 mL deionized water, and 0.5 g of $Ca(OH)_2$. The solutions were vortexed vigorously and left to stand for approximately 30 min, then centrifuged at 1000×g for 10 min, after which 0.5 mL of supernatant was transferred to a glass tube containing 0.25 μL of 4% $CuSO_4.5H_2O$. Three mL of concentrated sulfuric acid was added to the solutions, and the solutions were homogenized using a vortex mixer, heated in a boiling water bath for 5 minutes, and then chilled to below 20° C. by submerging in an ice bath. Once the solution had cooled, 50 μL p-hydroxydiphenol were added, the tubes were vortexed, heated in a 30° C. water bath 30 min, then returned to the boiling water bath for 1.5 minutes to burn off excess alkali. Tubes were cooled in the ice bath and 30 μL of the solutions were transferred by pipette to one of the wells in a 96-well plate. Absorbance was determined at a wavelength of 560 nm using a plate reader. Values were assessed using computer software based on the regression line generated from the 5 standards.

All data was analyzed using the MIXED procedure of SAS (version 9.2). Treatment was used as fixed effect and replicate was used as random effect. Least-square means were compared using the pdiff function in SAS.

B. Results of Dry Matter, pH, VFA, Lactic Acid, and Acetic Acid Content in Samples Corn silage prepared with *Megasphaera elsdenii* contained slightly less dry matter compared to the control silage (38.8% vs. 40.3%; P<0.02) (Table 6). Additional fermentation characteristics are presented in Table 6. Silage pH was slightly lower for the *Megasphaera elsdenii*-treated silage compared to the Control (untreated) silage (3.77 vs. 3.81; P=0.01). Compared to the Control silage, product treated with *Megasphaera elsdenii* contained greater concentrations of propionate (6.1 mM vs. 10.0 mM; P=0.04), isobutyrate (3.6 mM vs. 5.1 mM; P<0.01), and total volatile fatty acids (297.6 mM vs. 359.1 mM; P<0.001), but contained less lactic acid (4.36 M vs. 4.75 M; P=0.01). The majority of volatile fatty acids present in both silages consisted of acetic acid, which was greater in the corn silage treated with *Megasphaera elsdenii* (342.6 mM vs. 286.6 mM; P<0.001; FIG. 25).

TABLE 6

Fermentation characteristics of liquid extracts from silage treated with *Megasphaera elsdenii*. Concentrations of organic acids and pH values reflect characteristics of liquid extracts after 120 days of ensiling.

| Volatile fatty acid, mM | Control | *Megasphaera* | SEM | P-value |
|---|---|---|---|---|
| Total | 297.6 | 359.1 | 17.95 | <0.001 |
| Propionate | 6.13 | 10.00 | 1.815 | 0.04 |
| Isobutyrate | 3.55 | 5.08 | 0.898 | <0.01 |
| Butyrate | 0.76 | 0.93 | 0.281 | 0.54 |
| Lactate, M | 4.75 | 4.36 | 0.14 | 0.01 |
| pH | 3.81 | 3.77 | 0.016 | 0.01 |
| Dry matter, % | 40.3 | 38.8 | 0.66 | 0.02 |

Corn silage treated with *Megasphaera elsdenii* had a lower pH and less lactic acid, but contained greater concentrations of volatile fatty acids compared to an untreated control group. Most notably, concentrations of acetic acid were greater for silages treated with *Megasphaera elsdenii*, which could improve aerobic stability of corn silage when the ensiled material is exposed to ambient air and activity of aerobic organisms increases potentially spoiling the ensiled material (feedout phase). Silages with increased concentrations of acetic acids generally are believed to improve aerobic stability of silage. Treatment of plant material with *Megasphaera elsdenii* increased acetic acid concentrations by approximately 20% compared to an untreated control (FIG. 25), indicating that this treatment will increase aerobic stability of the treated silage.

Example 7

Treating Reconstituted High Moisture Corn Grain with *M. elsdenii* Alters Fermentation Characterisitcs Compared to Untreated Control A. Method of Ensiling Reconstituted High Moisture Corn Grain and Measuring Dry Matter, pH, VFA, Lactic Acid, Acetic Acid, and Digestibility in Samples Corn grain was dry rolled to a mean geometric particle size of approximately 3,000 µm (3 mm) and then combined with water to achieve a final moisture content of 32%. Experimental treatments consisted of an untreated control (Control) and corn treated with *Megasphaera elsdenii* strain NCIMB 41125 (MS Biotec, Wamego, KS). *Megasphaera elsdenii* were prediluted in an anaerobic diluent and applied to the grain as an aerosol, providing approximately 45 million CFUs per pound of grain. The mixture was then homogenized by blending for 3 minutes with a planetary mixer (Univex M20, Salem, NH). The blended mixtures were then divided into 2-pound aliquots, which were placed into foil pouches and vacuum sealed. This process was repeated four times for each treatment. Bags within each treatment and replicate were assigned a fermentation length of 0, 7, 14, 21 or 28 days. Day 0 bags were immediately placed into a freezer for storage. The remaining bags were placed into an insulated chest and held for their respective ensiling periods of 7, 14, 21, or 28 days. After ensiling, the bags were removed from the chest and placed into a freezer.

After fermentation, the pH of the resulting products was determined by mixing 25 grams of a sample (dry matter basis) with 70 mL of distilled water. The mixtures were placed onto an orbital shaker at 100 RPM for 30 minutes, and then strained through filament paper. The permeate was collected and pH was determined using a calibrated pH meter. Four mL of permeate was then combined with 1 mL of 25% metaphosphoric acid solution, homogenized with a vortex mixer, and frozen. The samples were then thawed, homogenized with a vortex mixer, and 2 mL of the liquid fraction was transferred to centrifuge tubes and centrifuged at 14,000×g for 15 minutes. Supernatant was removed and placed into chromatography vials. The concentrations of volatile fatty acids, including acetate, propionate, isobutyrate, butyrate, isovalerate, valerate, isocaproate, caproate, and heptanoate were determined by gas chromatography using an Agilent 7890 gas chromatograph equipped with a flame ionization detector and Nukol capillary column (15 m length×0.53 mm diameter, 0.50 µm film thickness). Samples were measured in duplicate.

Colorimetric lab analyses were utilized to determine concentration of lactic acid in corn extracts. Lactic acid standards were prepared at concentrations of 0, 2.5, 5, 10, and 15 mg/dL. The filtered, acidified, and centrifuged permeate was diluted by combining 20 parts distilled water with 1 part permeate, and homogenizing with a vortex mixer. The diluted sample (0.5 mL) was mixed with 4 mL of deionized water, 0.5 g calcium hydroxide, and 0.5 mL 20% copper sulfate solution. The mixtures were centrifuged for 10 minutes at 1000×g. The resulting supernatant (0.5 mL) was mixed with 25 µL of 4% copper sulfate solution and 3 mL sulfuric acid, mixed, and immediately placed into a boiling water bath for 5 minutes. The samples were then placed into an ice bath and cooled to room temperature. Fifty (50) µL of P-hydroxydiphenyl was added to the solution, the mixtures were homogenized with a vortex mixer, and then placed into an 86° F. (30° C.) bath for 30 minutes. The samples were then placed into a boiling water bath, and after 90 seconds were removed from the bath and allowed to cool to room temperature. Two hundred (200) µL of the solution was placed into the well of a 96-well plate and absorbance was read at 560 nm using a plate reader. Samples were analyzed in quadruplicate.

The digestibility of corn treated with *Megasphaera elsdenii* was evaluated using an in vitro culture system. Ruminal fluid was collected from cannulated Jersey crossbred steers housed at the Kansas State University Beef Cattle Research Center. Ruminal fluid was strained through cheesecloth, poured into a separatory funnel, sparged with nitrogen gas, and placed into an incubator at 102° F. (39° C.) for approximately 45 minutes to allow for stratification into layers. The bottom layer was discarded and the middle layer was collected and used as microbial inoculum for the in vitro analyses. Ten (10) mL of the strained ruminal fluid were added to culture bottles containing 140 mL of McDougall's buffer and 3 grams of grain (dry basis). Contents were sparged with nitrogen, bottles were capped with ANKOM pressure sensing modules (ANKOM RF Gas Production System, Macedon, NY), placed into an orbital bed incubator at 102° F. (39° C.), and agitated continuously for 16 hours. At the end of the incubation cycle, bottles were removed from the shaker and pH was measured using a calibrated pH meter. Four (4) mL of the fluid layer was transferred to vials, mixed with 1 mL of 25% metaphosphoric acid solution, homogenized with a vortex mixer, and then placed into a freezer. The remaining contents of each bottle were emptied into a shallow aluminum pan and dried at 221° F. (105° C.) for 48 hours. Weight of the dried mass was recorded, and disappearance of dry matter was determined for each culture. Organic acid profiles were determined for each of the cultures by gas chromatography using procedures described previously for grain extracts.

B. Results of Dry Matter, pH, VFA, Lactic Acid, and Acetic Acid Content in Samples Changes in pH of grains during the 28-day ensiling period are shown in FIG. 26. Treating grain with *Megasphaera elsdenii* resulted in a more rapid pH decrease from day 0 to 7 compared to the control (untreated) grain (P<0.01), and differences in pH persisted at 14, 21, and 28 days of ensiling (effect of treatment; effect of time; and interaction between treatment and days of ensiling; P<0.01). Organic acid profiles of the grains are summarized in Table 7. Compared to the control grain, total concentrations of volatile fatty acids were greater for reconstituted grain treated with *Megasphaera elsdenii* at 7 and 14 days of ensiling (P<0.05), but were not different thereafter (P>0.50). The concentrations of acetic acid and propionic acid were similar for grains ensiled with and without *Megasphaera elsdenii* treatment (P>0.10). The concentrations of isovaleric, valeric, isocaproic, caproic, and heptanoic acids generally were greater for grain treated with *Megasphaera elsdenii* compared to the control (P<0.05), but lactic acid concentrations were similar for grains with or without *Megasphaera elsdenii* treatment (P>0.10).

TABLE 7

Organic acid concentrations of liquid extracts from reconstituted high moisture corn grain treated with *Megasphaera elsdenii* or untreated control group.

| Organic acid, mM | Days of ensiling | | | | | SEM[‡] | P-value[§] |
|---|---|---|---|---|---|---|---|
| | 0 | 7 | 14 | 21 | 28 | | |
| Total volatile fatty acids | | | | | | | |
| Control | 14.2 | 34.3 | 40.9 | 55.3 | 60.0 | 10.2 | M, D |
| Megasphaera | 18.2 | 59.0 | 59.4 | 59.0 | 56.7 | | |
| Acetic acid | | | | | | | |
| Control | 8.3 | 28.1 | 34.6 | 43.5 | 48.6 | 7.5 | D |
| Megasphaera | 11.9 | 42.1 | 41.9 | 42.3 | 43.7 | | |
| Propionic acid | | | | | | | |
| Control | 0.6 | 0.6 | 0.0 | 2.6 | 2.1 | 1.0 | — |
| Megasphaera | 0.5 | 0.0 | 1.3 | 0.0 | 1.6 | | |
| Butyric acid | | | | | | | |
| Control | 0.0 | 0.0 | 0.0 | 0.4 | 1.4 | 0.3 | D |
| Megasphaera | 0.0 | 0.0 | 0.0 | 0.0 | 0.4 | 0.4 | |
| Isobutyric acid | | | | | | | |
| Control | nd | nd | nd | nd | nd | — | — |
| Megasphaera | nd | nd | nd | nd | nd | | |
| Valeric acid | | | | | | | |
| Control | 0.0 | 2.5 | 2.9 | 3.6 | 3.3 | 1.2 | M, D |
| Megasphaera | 0.0 | 8.0 | 7.5 | 8.6 | 5.2 | | |
| Isovaleric acid | | | | | | | |
| Control | 0.0 | 0.9 | 0.8 | 1.9 | 1.5 | 0.9 | M, D |
| Megasphaera | 0 | 3.1 | 2.9 | 2.0 | 1.6 | | |
| Caproic acid | | | | | | | |
| Control | 0.0 | 0.9 | 0.8 | 1.0 | 1.0 | 0.6 | M, D |
| Megasphaera | 0.0 | 2.4 | 2.3 | 1.6 | 1.4 | | |
| Isocaproic acid | | | | | | | |
| Control | 0.0 | 0.0 | 0.0 | 0.3 | 0.0 | 0.4 | M |
| Megasphaera | 0.0 | 0.5 | 0.5 | 1.3 | 0.5 | | |
| Heptanoic acid | | | | | | | |
| Control | 5.3 | 1.4 | 1.8 | 2.0 | 2.1 | 0.5 | M, D |
| Megasphaera | 5.9 | 2.9 | 2.9 | 3.1 | 2.4 | | |

TABLE 7-continued

Organic acid concentrations of liquid extracts from reconstituted high moisture corn grain treated with *Megasphaera elsdenii* or untreated control group.

| Organic acid, mM | Days of ensiling | | | | | SEM[‡] | P-value[§] |
|---|---|---|---|---|---|---|---|
| | 0 | 7 | 14 | 21 | 28 | | |
| Control | 1.1 | 39.8 | 50.9 | 52.4 | 57.5 | 5.4 | D |
| Megasphaera | 1.1 | 42.2 | 49.7 | 48.4 | 51.7 | | |

[‡] = Standard error of the mean.
[§] = probability of a treatment effect (P < 0.05). M = Effect of treatment. D = Effect of days of ensiling. I = Interaction between treatment and days of ensiling.

In vitro dry matter content changes are summarized for *Megasphaera elsdenii*-treated corn and untreated corn in FIG. 27. Treatment of corn with *Megasphaera elsdenii* did not alter susceptibility of corn grain to microbial digestion compared to the untreated control grain. A decrease of dry matter from cultures generally increased in response to days of ensiling, but there was no apparent interaction between days of ensiling and *Megasphaera elsdenii* treatment to the corn.

This example shows that treating high-moisture grains with *Megasphaera elsdenii* alters fermentation characteristics of the ensiled grain compared to the control (untreated) grain. This method constitutes a way to accelerate fermentation activity in reconstituted high-moisture grain.

Example 8

Treating Corn Silage with *M. elsdenii* that is Fed to Cattle Improves Carcass Value Compared to Untreated Control A. Method of Feeding Cattle, Feed Composition, and Harvesting Carcasses Crossbred steers (336 head; 633±14.1 lb) were used in a backgrounding study to evaluate impact of *Megasphaera elsdenii* as a silage treatment on growth performance. Approximately 24 hours after arriving at the Beef Cattle Research Center, steers were vaccinated with Bovishield Gold 5 and Ultrabac 7/Somnubac (Zoetis Animal Health, Florham Park, NJ), treated with a pour-on ectoparasiticide (StandGuard, Elanco Animal Health, Greenfield, IN), identified with numbered eartags, implanted with Component TE-200 with Tylan (Elanco Animal Health), and weighed.

Steers were stratified by initial body weight and allocated, within strata, to 28 feedlot pens with 14 cattle per pen and 14 pens per treatment. Treatments consisted of backgrounding diets (Table 8) prepared from untreated corn silage (Control) or corn silage treated with 1 billion colony forming units of *Megasphaera elsdenii* (strain NCIMB 41125; MS Biotec, Wamego, KS) per ton of fresh forage material. Steers were fed ad libitum once daily for 112 days.

TABLE 8

Composition of backgrounding and finishing diets.

| | Backgrounding phase | | Finishing phase |
|---|---|---|---|
| | Control | Megasphaera | |
| Ingredient, % of dry matter | | | |
| Steam-flaked corn | — | — | 57.68 |
| Sweetbran[1] | — | — | 30.00 |
| Control corn silage (no inoculant) | 57.21 | — | — |
| Corn silage inoculated with *M. elsdenii*[2] | — | 57.21 | — |

TABLE 8-continued

Composition of backgrounding and finishing diets.

|  | Backgrounding phase | | Finishing phase |
|---|---|---|---|
|  | Control | Megasphaera |  |
| Alfalfa hay | 38.36 | 38.36 | 10.00 |
| Supplement[3] | 4.43 | 4.43 | — |
| Supplement[4] | — | — | 2.32 |
| Nutrient composition (DM basis) | | | |
| Crude protein, % | 12.50 | 12.50 | 13.30 |
| Net energy for maintenance, Mcal/cwt | 66 | 66 | 0.97 |
| Net energy for gain, Mcal/cwt | 40 | 40 | 0.66 |
| Neutral detergent fiber, % | 39.1 | 39.1 | 19.06 |
| Calcium, % | 0.65 | 0.65 | 0.66 |
| Phosphorous, % | 0.27 | 0.27 | 0.49 |

[1]Wet corn gluten feed, Cargill Starches & Sweeteners North America; Minneapolis, MN.
[2]Megasphaera elsdenii strain NCIMB 41125 was applied to forage at the harvester using an onboard aerosol applicator at the rate of 50 mL of fresh culture per ton of fresh-cut forage material. Inoculant provided 100 billion colony-forming units per ton of forage. No microbial inoculant was used in preparing the control corn silage.
[3]Contained soybean meal, limestone, salt, trace mineral, vitamin, and feed additive premixes, and provided (on a total diet DM basis) 0.25% salt, 0.15 ppm cobalt, 10 ppm copper, 0.50 ppm iodine, 20 ppm manganese, 0.10 ppm selenium, 30 ppm zinc, 1000 IU/lb vitamin A, 10 IU/lb vitamin E, and 30 grams/ton Rumensin (Elanco Animal Health).
[4]Contained limestone, salt, urea, trace mineral, vitamin, and feed additive premixes, and provided (on a total diet DM basis) 0.25% salt, 0.15 ppm cobalt, 10 ppm copper, 0.50 ppm iodine, 20 ppm manganese, 0.10 ppm selenium, 30 ppm zinc, 1000 IU/lb vitamin A, 10 IU/lb vitamin E, and 30 grams/ton Rumensin (Elanco Animal Health). Tylosin phosphate (Tylan, Elanco Animal Health) was fed at the rates of 0 or 8 grams/ton during the finishing phase (equally distributed across backgrounding phase treatments). Ractopamine hydrochloride (Optaflexx, Elanco Animal Health) was fed at the rate of 24 grams/ton for the final 34 days before harvest.

At the end of the backgrounding phase, cattle were weighed, re-implanted with Component TE-200 Tylan impants, and transitioned to a common finishing diet (Table 8). Cattle were fed ad libitum once daily for a total of 115 days during the finishing phase. At the end of the finishing phase, pens were weighed and steers were transported to a commercial abattoir, where hot carcass weight and liver abscess incidence were collected on day of harvest.

Ribeye area, 12$^{th}$-rib backfat thickness, marbling score, and USDA quality and yield grades were collected after 36 hours of refrigeration. Final live weight was computed as hot carcass weight divided by a common dressing percentage of 63%, and average daily gain and feed efficiency were computed using the carcass-adjusted live weight. Carcass value was determined using a standardized grid that was constructed using 10-year averages for base price and carcass premiums and discounts, as reported by USDA (January 2008 to January 2018).

Data were analyzed in SAS version 9.2 (SAS Inst. Inc., Cary, NC) using the MIXED procedure for continuous data and the GLIMMIX procedure for categorical data. Backgrounding treatment was the fixed effect, block was the random effect, and pen was the experimental unit.

B. Results of Cattle Growth and Feed Intake Anc Carcass Characteristics

Performance of cattle during the backgrounding and finishing phases is summarized in Table 9. Average daily gain, dry matter intake, and feed:gain during the growing and finishing phases were similar for cattle fed backgrounding diets containing corn silages with and without microbial inoculant ($P>0.10$).

TABLE 9

Backgrounding and finishing performance of steers that were fed corn silage, with or without Megasphaera elsdenii as a silage treatment, during the backgrounding phase (prior to feedlot finishing). Megasphaera elsdenii strain NCIMB 41125 was applied at the harvester using an onboard aerosol applicator at the rate of 50 mL of fresh culture per ton of fresh forage material. Inoculant provided 100 billion colony-forming units per ton of forage. Control silage treatment received no inoculant.

|  | Control | Megasphaera | SEM[¥] | P-value |
|---|---|---|---|---|
| Backgrounding performance | | | | |
| Initial weight, lb | 635 | 632 | 1.4 | 0.10 |
| Final weight, lb | 1010 | 1005 | 17.7 | 0.83 |
| Average daily gain, lb | 3.39 | 3.40 | 0.028 | 0.71 |
| Dry matter intake, lb/day | 19.14 | 19.51 | 0.411 | 0.28 |
| Feed:gain | 5.65 | 5.73 | 0.092 | 0.36 |
| Finishing performance | | | | |
| Carcass-adjusted final weight, lb[‡] | 1361 | 1377 | 16.9 | 0.35 |
| Carcass-adjusted average daily gain, lb[‡] | 3.05 | 3.24 | 0.132 | 0.16 |
| Dry matter intake, lb/day | 23.72 | 23.99 | 0.370 | 0.48 |
| Carcass-adjusted feed:gain[‡] | 8.03 | 7.50 | 0.359 | 0.16 |

[¥]Standard error of the mean.
[‡]Final weight calculated as hot carcass weight divided by a standardized dressed yield of 63%.

Carcass characteristics are presented in Table 10. Individual measures of carcass characteristics were similar for the two treatments ($P>0.10$); however, the cumulative impact of non-significant changes in carcass characteristics tended ($P<0.07$) to increase overall carcass value for cattle fed silage inoculated with Megasphaera elsdenii when compared to cattle fed untreated silage ($1628.68 vs. $1597.98) (FIG. 28). This difference was largely driven by non-significant but substantial increases in carcass weight for the Megasphaera elsdenii silage group, as well as smaller differences in carcass quality and yield grades. We believe that these differences actually manifested during the backgrounding phase, but were likely masked by differences in gastrointestinal tract fill. Thus, this experiment shows that feeding cattle silage treated with Megasphaera elsdenii increases overall carcass value.

TABLE 10

Carcass characteristics of steers that were fed corn silage, with or without Megasphaera elsdenii as silage inoculant, during the backgrounding phase (prior to feedlot finishing).

|  | Control | Megasphaera | SEM[¥] | P-value |
|---|---|---|---|---|
| Hot carcass weight, lb | 857 | 868 | 9.1 | 0.23 |
| 12$^{th}$ rib fat thickness, in | 0.53 | 0.53 | 0.019 | 0.94 |
| Ribeye area, in$^2$ | 14.28 | 14.36 | 0.200 | 0.69 |
| Marbling score[‡] | 407 | 409 | 7 | 0.78 |
| USDA quality grade, % | | | | |
| Choice | 50.6 | 57.3 | 5.43 | 0.21 |
| Select | 48.2 | 42.1 | 5.42 | 0.26 |
| Sub-select[§] | 1.2 | 0.6 | 0.85 | 0.15 |
| Overall USDA yield grade | 2.42 | 2.44 | 0.090 | 0.86 |
| Yield grade 1, % | 10.4 | 12.4 | 6.71 | 0.77 |
| Yield grade 2, % | 46.3 | 38.7 | 8.60 | 0.38 |
| Yield grade 3, % | 34.7 | 42.2 | 7.96 | 0.34 |

TABLE 10-continued

Carcass characteristics of steers that were fed corn silage, with or without *Megasphaera elsdenii* as silage inoculant, during the backgrounding phase (prior to feedlot finishing).

|  | Control | *Megasphaera* | SEM[¥] | P-value |
|---|---|---|---|---|
| Yield grade 4, % | 8.0 | 6.0 | 2.91 | 0.50 |
| Yield grade 5, % | 0.6 | 0.7 | 0.85 | 0.99 |
| Liver abscess, % | 12.7 | 16.7 | 5.20 | 0.44 |

[†]*Megasphaera elsdenii* strain NCIMB 41125 was applied at the harvester using an onboard aerosol applicator at the rate of 50 mL of fresh culture per ton of fresh forage material. Inoculant provided 100 billion colony-forming units per ton of forage. Control silage treatment received no inoculant.
[¥]Standard error of the mean.
[‡]Marbling score determined by computer imaging system (VBG 2000, E + V Technology GmbH & Co. KG, Oranienburg, Germany). Small (400-499).
[§]Consists of carcasses grading USDA Standard or Commercial.

What is claimed is:

1. A method of producing an ensiled plant material with improved aerobic stability, comprising:
    (a) applying an effective amount of *Megasphaera elsdenii* (*M elsdenii*) cells to a plant material, and
    (b) ensiling the plant material to produce an ensiled plant material,
    wherein the ensiled plant material comprises improved aerobic stability as compared to a control ensiled plant material produced in the absence of the *M. elsdenii* cells.

2. The method of claim 1, wherein the improved aerobic stability comprises a decreased pH.

3. The method of claim 1, further comprising applying an additive to the plant material.

4. The method of claim 3, wherein the additive is selected from the group consisting of: another microorganism, an enzyme, a fermentable substrate, an acid, a preservative, a nutrient, and combinations thereof.

5. The method of claim 1, wherein the applying is before harvesting of the plant material, after harvesting of the plant material, at the time of ensiling, or combinations thereof.

6. The method of claim 1, wherein the *M. elsdenii* cells are selected from the group consisting of: ATCC® 25940, ATCC® 17752, ATCC® 17753, NCIMB 702261, NCIMB 702262, NCIMB 702264, NCIMB 702331, NCIMB 702409, NCIMB 702410, NCIMB 41125, NCIMB 41787, NCIMB 41788 and combinations thereof.

7. The method of claim 1, wherein the *M. elsdenii* cells are *M. elsdenii* NCIMB 41125 cells.

8. The method of claim 1, wherein the plant material is selected from the group consisting of: a forage, crop, grass, legume, grain, fruit, vegetable, and combinations thereof.

9. The method of claim 1, wherein the plant material is corn, alfalfa, wheat, rye, barley, oats, triticale, millet, clover, sorghum, and combinations thereof.

10. The method of claim 1, comprising applying the *M. elsdenii* cells in a liquid.

11. The method of claim 1, wherein the method further comprises mixing freeze-dried *M. elsdenii* cells with a liquid prior to applying the cells.

12. The method of claim 1, comprising applying the *M. elsdenii* cells as freeze-dried cells.

13. The method of claim 12, wherein the freeze-dried cells are encapsulated.

14. The method of claim 12, wherein a dry carrier comprises the freeze-dried cells.

15. The method of claim 1, comprising applying at least about $10^6$ to about $10^{14}$ CFU of *M. elsdenii* cells per ton of plant material.

16. An ensiled plant material produced by the method of claim 1.

17. A method of producing an increased amount of an ensiled plant material, comprising:
    (a) applying an effective amount of *Megasphaera elsdenii* (*M elsdenii*) cells to a plant material, and
    (b) ensiling the plant material to produce an ensiled plant material,
    wherein the amount of the ensiled plant material produced is increased as compared to the amount of a control ensiled plant material produced in the absence of the *M. elsdenii* cells.

18. The method of claim 17, wherein the plant material is selected from the group consisting of: a forage, crop, grass, legume, grain, fruit, vegetable, and combinations thereof.

19. A method of producing an ensiled plant material, comprising:
    (a) applying *Megasphaera elsdenii* (*M. elsdenii*) cells to a plant material, wherein the cells are selected from the group consisting of: ATCC® 25940, ATCC® 17752, ATCC® 17753, NCIMB 702261, NCIMB 702262, NCIMB 702264, NCIMB 702331, NCIMB 702409, NCIMB 702410, NCIMB 41125, NCIMB 41787, NCIMB 41788 and combinations thereof, and
    (b) ensiling the plant material to produce an ensiled plant material.

20. The method of claim 19, wherein the plant material is selected from the group consisting of: a forage, crop, grass, legume, grain, fruit, vegetable, and combinations thereof.

* * * * *

UNITED STATES PATENT AND TRADEMARK OFFICE
CERTIFICATE OF CORRECTION

PATENT NO. : 11,814,617 B2
APPLICATION NO. : 16/756482
DATED : November 14, 2023
INVENTOR(S) : Drouillard et al.

It is certified that error appears in the above-identified patent and that said Letters Patent is hereby corrected as shown below:

In the Drawings

On Sheet 19 of 28, FIG. 19, delete "-80C" and insert -- -80°C -- at each occurrence throughout the Fig. 19.

On Sheet 23 of 28, FIG. 23, delete "25C" and insert -- 25°C -- at each occurrence throughout the Fig. 23.

On Sheet 23 of 28, FIG. 23, delete "4C" and insert -- 4°C -- at each occurrence throughout the Fig. 23.

On Sheet 23 of 28, FIG. 23, delete "-80C" and insert -- -80°C --, therefor.

On Sheet 26 of 28, FIG. 26, delete "Inoculationt" and insert -- Inoculation --, therefor.

On Sheet 27 of 28, FIG. 27, delete "Inoculationt" and insert -- Inoculation --, therefor.

In the Specification

In Column 9, Line 3, delete "alapacas," and insert -- alpacas, --, therefor.

In Column 10, Line 62, delete "cornyiformis," and insert -- coryniformis, --, therefor.

In Column 10, Line 63, delete "salivarus," and insert -- salivarius, --, therefor.

In Column 10, Line 65, delete "pentocaceus," and insert -- pentosaceus, --, therefor.

In Column 20, Line 17, delete "galatin," and insert -- gelatin, --, therefor.

In Column 28, Line 37, delete "p-hydroxydiphenol" and insert -- p-hydroxydiphenyl --, therefor.
In Column 29, Line 35, delete "Characterisitcs" and insert -- Characteristics --, therefor.

Signed and Sealed this
Nineteenth Day of March, 2024

Katherine Kelly Vidal
*Director of the United States Patent and Trademark Office*

CERTIFICATE OF CORRECTION (continued)
U.S. Pat. No. 11,814,617 B2

In Column 33, Line 36, delete "impants," and insert -- implants, --, therefor.

In Column 33, Line 59, delete "Anc" and insert -- and --, therefor.

In Column 34, Line 4, delete "com" and insert -- corn --, therefor.

In Column 35, Line 8, delete "yieid" and insert -- yield --, therefor.

In the Claims

In Claim 1, Column 35, Line 22, delete "(*M*" and insert -- (*M.* --, therefor.

In Claim 17, Column 36, Line 24, delete "(*M*" and insert -- (*M.* --, therefor.